(12) United States Patent
Lipkens et al.

(10) Patent No.: US 9,796,956 B2
(45) Date of Patent: Oct. 24, 2017

(54) MULTI-STAGE ACOUSTOPHORESIS DEVICE

(71) Applicant: FloDesign Sonics, Inc., Wilbraham, MA (US)

(72) Inventors: Bart Lipkens, Hampden, MA (US); Thomas J. Kennedy, III, Wilbraham, MA (US); Jeffrey King, Coventry, CT (US); Jason Barnes, Westfield, MA (US); Brian McCarthy, East Longmeadow, MA (US); Dane Mealey, Springfield, MA (US); Erik Miller, Belchertown, MA (US); Walter M. Presz, Jr., Wilbraham, MA (US); Benjamin Ross-Johnsrud, Wilbraham, MA (US); John Rozembersky, Boxborough, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 15/284,529

(22) Filed: Oct. 3, 2016

(65) Prior Publication Data

US 2017/0088809 A1    Mar. 30, 2017

Related U.S. Application Data

(63) Continuation-in-part of application No. 14/533,753, filed on Nov. 5, 2014, now Pat. No. 9,512,395.
(Continued)

(51) Int. Cl.
*C12M 1/26* (2006.01)
*C12N 13/00* (2006.01)
(Continued)

(52) U.S. Cl.
CPC .......... *C12M 33/08* (2013.01); *B06B 1/0223* (2013.01); *B06B 1/06* (2013.01); *C12M 47/02* (2013.01); *C12N 13/00* (2013.01)

(58) Field of Classification Search
CPC ... C02F 1/34; C02F 1/36; B01J 19/008; B01J 19/26; B01J 19/10; B01D 21/283;
(Continued)

(56) References Cited

U.S. PATENT DOCUMENTS 2,473,971 A    6/1949 Ross
2,667,944 A    2/1954 Crites
(Continued)

FOREIGN PATENT DOCUMENTS

DE    30 27 433 A1    2/1982
DE    32 18 488 A1    11/1983
(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron Allen
(74) *Attorney, Agent, or Firm* — Rick Klein, Esq.; Fay Sharpe, LLP

(57) ABSTRACT

An acoustophoresis device made up of modular components is disclosed. Several modules are disclosed herein, including ultrasonic transducer modules, input/output modules, collection well modules, and various connector modules. These permit different systems to be constructed that have appropriate fluid dynamics for separation of particles, such as biological cells, from a fluid.

20 Claims, 61 Drawing Sheets

Related U.S. Application Data

(60) Provisional application No. 62/322,262, filed on Apr. 14, 2016, provisional application No. 62/307,489, filed on Mar. 12, 2016, provisional application No. 62/235,614, filed on Oct. 1, 2015, provisional application No. 62/020,088, filed on Jul. 2, 2014, provisional application No. 61/900,635, filed on Nov. 6, 2013.

(51) Int. Cl.
  *C12M 1/00* (2006.01)
  *B06B 1/06* (2006.01)
  *B06B 1/02* (2006.01)

(58) Field of Classification Search
  CPC ........... B01D 2021/0081; B01D 43/00; C12M 33/08; C12M 47/02; C12N 13/00; B06B 1/06; B06B 1/0223
  See application file for complete search history.

(56) References Cited

U.S. PATENT DOCUMENTS

| | | | |
|---|---|---|---|
| 3,372,370 | A | 3/1968 | Cyr |
| 3,555,311 | A | 1/1971 | Weber |
| 4,055,491 | A | 10/1977 | Porath-Furedi |
| 4,065,875 | A | 1/1978 | Srna |
| 4,118,649 | A | 10/1978 | Schwartzman et al. |
| 4,158,629 | A | 6/1979 | Sawyer |
| 4,165,273 | A | 8/1979 | Azarov et al. |
| 4,173,725 | A | 11/1979 | Asai et al. |
| 4,204,096 | A | 5/1980 | Barcus et al. |
| 4,254,661 | A | 3/1981 | Kossoff et al. |
| 4,320,659 | A | 3/1982 | Lynnworth et al. |
| 4,344,448 | A | 8/1982 | Potts |
| 4,398,325 | A | 8/1983 | Piaget et al. |
| 4,552,669 | A | 11/1985 | Sekellick |
| 4,666,595 | A | 5/1987 | Graham |
| 4,673,512 | A | 6/1987 | Schram |
| 4,699,588 | A | 10/1987 | Zinn et al. |
| 4,743,361 | A | 5/1988 | Schram |
| 4,759,775 | A | 7/1988 | Peterson et al. |
| 4,800,316 | A | 1/1989 | Ju-Zhen |
| 4,821,838 | A | 4/1989 | Chen |
| 4,836,684 | A | 6/1989 | Javorik et al. |
| 4,860,993 | A | 8/1989 | Goode |
| 4,878,210 | A | 10/1989 | Mitome |
| 4,983,189 | A | 1/1991 | Peterson et al. |
| 5,059,811 | A | 10/1991 | King et al. |
| 5,062,965 | A | 11/1991 | Bernou et al. |
| 5,085,783 | A | 2/1992 | Feke et al. |
| 5,164,094 | A | 11/1992 | Stuckart |
| 5,225,089 | A | 7/1993 | Benes et al. |
| 5,371,429 | A | 12/1994 | Manna |
| 5,395,592 | A | 3/1995 | Bolleman et al. |
| 5,431,817 | A | 7/1995 | Braatz et al. |
| 5,443,985 | A | 8/1995 | Lu et al. |
| 5,452,267 | A | 9/1995 | Spevak |
| 5,475,486 | A | 12/1995 | Paoli |
| 5,484,537 | A | 1/1996 | Whitworth |
| 5,527,460 | A | 6/1996 | Trampler et al. |
| 5,560,362 | A | 10/1996 | Sliwa, Jr. et al. |
| 5,594,165 | A | 1/1997 | Madanshetty |
| 5,604,301 | A | 2/1997 | Mountford et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,831,166 | A | 11/1998 | Kozuka et al. |
| 5,834,871 | A | 11/1998 | Puskas |
| 5,902,489 | A | 5/1999 | Yasuda et al. |
| 5,912,182 | A | 6/1999 | Coakley et al. |
| 5,947,299 | A | 9/1999 | Vazquez et al. |
| 5,951,456 | A | 9/1999 | Scott |
| 6,090,295 | A | 7/2000 | Raghavarao et al. |
| 6,166,231 | A | 12/2000 | Hoeksema |
| 6,205,848 | B1 | 3/2001 | Faber et al. |
| 6,216,538 | B1 | 4/2001 | Yasuda et al. |
| 6,273,262 | B1 | 8/2001 | Yasuda et al. |
| 6,332,541 | B1 | 12/2001 | Coakley et al. |
| 6,391,653 | B1 | 5/2002 | Letcher et al. |
| 6,475,151 | B2 | 11/2002 | Koger et al. |
| 6,482,327 | B1 | 11/2002 | Mori et al. |
| 6,487,095 | B1 | 11/2002 | Malik et al. |
| 6,592,821 | B1 | 7/2003 | Wada et al. |
| 6,641,708 | B1 | 11/2003 | Becker et al. |
| 6,649,069 | B2 | 11/2003 | DeAngelis |
| 6,699,711 | B1 | 3/2004 | Hahn et al. |
| 6,727,451 | B1 | 4/2004 | Fuhr et al. |
| 6,763,722 | B2 | 7/2004 | Fjield et al. |
| 6,881,314 | B1 | 4/2005 | Wang et al. |
| 6,929,750 | B2 | 8/2005 | Laurell et al. |
| 6,936,151 | B1 | 8/2005 | Lock et al. |
| 7,008,540 | B1 | 3/2006 | Weavers et al. |
| 7,010,979 | B2 | 3/2006 | Scott |
| 7,061,163 | B2 | 6/2006 | Nagahara et al. |
| 7,081,192 | B1 | 7/2006 | Wang et al. |
| 7,093,482 | B2 | 8/2006 | Berndt |
| 7,108,137 | B2 | 9/2006 | Lal et al. |
| 7,150,779 | B2 | 12/2006 | Meegan, Jr. |
| 7,186,502 | B2 | 3/2007 | Vesey |
| 7,191,787 | B1 | 3/2007 | Redeker et al. |
| 7,322,431 | B2 | 1/2008 | Ratcliff |
| 7,331,233 | B2 | 2/2008 | Scott |
| 7,340,957 | B2 | 3/2008 | Kaduchak et al. |
| 7,373,805 | B2 | 5/2008 | Hawkes et al. |
| 7,541,166 | B2 | 6/2009 | Belgrader et al. |
| 7,601,267 | B2 | 10/2009 | Haake et al. |
| 7,673,516 | B2 | 3/2010 | Janssen et al. |
| 7,837,040 | B2 | 11/2010 | Ward et al. |
| 7,846,382 | B2 | 12/2010 | Strand et al. |
| 7,968,049 | B2 | 6/2011 | Takahashi et al. |
| 8,075,786 | B2 | 12/2011 | Bagajewicz |
| 8,080,202 | B2 | 12/2011 | Takahashi et al. |
| 8,134,705 | B2 | 3/2012 | Kaduchak et al. |
| 8,256,076 | B1 | 9/2012 | Feller |
| 8,266,950 | B2 | 9/2012 | Kaduchak et al. |
| 8,273,253 | B2 | 9/2012 | Curran |
| 8,273,302 | B2 | 9/2012 | Takahashi et al. |
| 8,309,408 | B2 | 11/2012 | Ward et al. |
| 8,319,398 | B2 | 11/2012 | Vivek et al. |
| 8,334,133 | B2 | 12/2012 | Fedorov et al. |
| 8,387,803 | B2 | 3/2013 | Thorslund et al. |
| 8,592,204 | B2 | 11/2013 | Lipkens et al. |
| 8,679,338 | B2 | 3/2014 | Rietman et al. |
| 8,691,145 | B2 | 4/2014 | Dionne et al. |
| 8,873,051 | B2 | 10/2014 | Kaduchak et al. |
| 8,889,388 | B2 | 11/2014 | Wang et al. |
| 9,272,234 | B2 | 3/2016 | Lipkens et al. |
| 9,357,293 | B2 | 5/2016 | Claussen |
| 9,365,815 | B2 | 6/2016 | Miyazaki et al. |
| 9,368,110 | B1 | 6/2016 | Hershey et al. |
| 9,388,363 | B2 | 7/2016 | Goodson et al. |
| 9,391,542 | B2 | 7/2016 | Wischnewskiy |
| 9,403,114 | B2 | 8/2016 | Kusuura |
| 9,410,256 | B2 | 8/2016 | Dionne et al. |
| 9,416,344 | B2 | 8/2016 | Lipkens et al. |
| 9,421,553 | B2 | 8/2016 | Dionne et al. |
| 9,422,328 | B2 | 8/2016 | Kennedy, III et al. |
| 9,457,139 | B2 | 10/2016 | Ward et al. |
| 9,457,302 | B2 | 10/2016 | Lipkens et al. |
| 9,458,450 | B2 | 10/2016 | Lipkens et al. |
| 9,464,303 | B2 | 10/2016 | Burke |
| 9,476,855 | B2 | 10/2016 | Ward et al. |
| 9,480,375 | B2 | 11/2016 | Marshall et al. |
| 9,480,935 | B2 | 11/2016 | Mariella, Jr. et al. |
| 9,488,621 | B2 | 11/2016 | Kaduchak et al. |
| 9,504,780 | B2 | 11/2016 | Spain et al. |
| 9,512,395 | B2 | 12/2016 | Lipkens et al. |
| 9,513,205 | B2 | 12/2016 | Yu et al. |
| 9,514,924 | B2 | 12/2016 | Morris et al. |
| 9,517,474 | B2 | 12/2016 | Mao et al. |
| 2002/0038662 | A1 | 4/2002 | Schuler et al. |
| 2002/0134734 | A1 | 9/2002 | Campbell et al. |

(56) References Cited

U.S. PATENT DOCUMENTS

| | | |
|---|---|---|
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181828 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1* | 1/2014 | Lipkens ................ B01D 21/28 435/71.1 |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0193381 A1* | 7/2014 | Warner ................ A61M 5/1407 424/93.7 |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 87/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 98/17373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |

(56) References Cited

FOREIGN PATENT DOCUMENTS

| | | |
|---|---|---|
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |
| WO | WO 2016/004398 A2 | 1/2016 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et a.; An Industrial-Prototype Acoustic Array for Real-Time Emulsion Layer Detection in Oil Storage Tanks; IEEE Sensors Journal, vol. 9, No. 12, Dec. 2009.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Ponomarenko et al.; Density of states and zero Landau level probed through capacitance of graphene; Nature Nanotechnology Letters, Jul. 5, 2009; DOI: 10.1038/NNANO.2009.177.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report, dated Jul. 18, 2013.

European Search Report of European Application No. 11769474.5, dated Sep. 5, 2013.

European Search Report of European Application No. 13760840.2, dated Feb. 4, 2016.

European Search Report of European Application No. 13721179.3 dated Feb. 23, 2016.

International Search Report and Written Opinion dated Dec. 20, 2011, for corresponding PCT application No. PCT/US2011/032181.

International Search Report and Written Opinion dated Feb. 27, 2012, for PCT application No. PCT/US2011/040787.

International Search Report and Written Opinion of International Application No. PCT/US2012/051804 dated Nov. 16, 2012.

International Search Report and Written Opinion of International Application No. PCT/US2013/037404 dated Jun. 21, 2013.

International Search Report and Written Opinion of International Application No. PCT/US2013/032705 dated Jul. 26, 2013.

International Search Report and Written Opinion of International Application No. PCT/US2013/050729 dated Sep. 25, 2013.

International Search Report dated Feb. 18, 2014 in corresponding PCT Application No. PCT/US2013/059640.

International Search Report for corresponding PCT Application Serial No. PCT/US2014/015382 dated May 6, 2014.

International Search Report for PCT/US2014/035557 dated Aug. 27, 2014.

International Search Report for PCT/US2014/043930 dated Oct. 22, 2014.

International Search Report for PCT/US2014/046412 dated Oct. 27, 2014.

International Search Report for PCT/US2014/064088 dated Jan. 30, 2015.

Extended European Search Report for Application No. EP 12833859.7 dated Mar. 20, 2015.

International Search Report and Written Opinion for International Application No. PCT/US2015/010595 dated Apr. 15, 2015.

International Search Report for PCT/US2015/019755 dated May 4, 2015.

International Search Report dated Jul. 30, 2015 for International Application No. PCT/US2015/030009.

International Search Report for PCT/US2015/039125 dated Sep. 30, 2015.

International Search Report and Written Opinion for PCT Application Serial No. PCT/US2015/053200 dated Dec. 28, 2015.

European Search Report of European Application No. 11796470.0 dated Jan. 5, 2016.

(56) References Cited

OTHER PUBLICATIONS

International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.
International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
PHYS. ORG. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
International Search Report and Written Opinion for International Application No. PCT/US2017/025108 dated Jul. 20, 2017.

\* cited by examiner

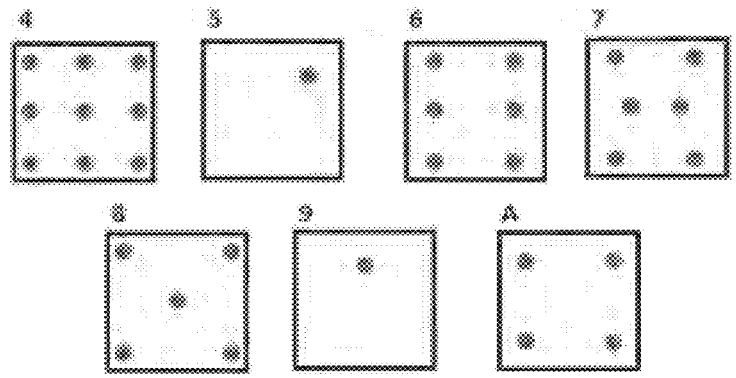
FIG. 34A
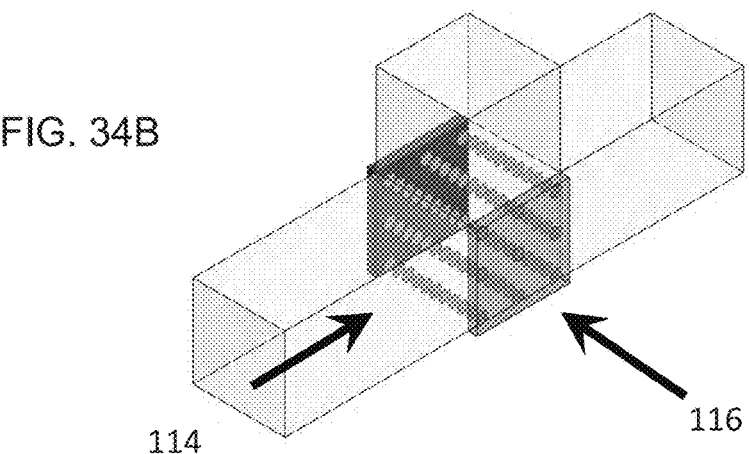
FIG. 34B
114   116
FIG. 34C
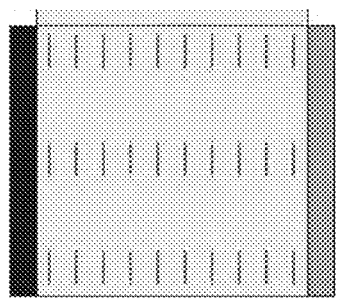
FIG. 34D
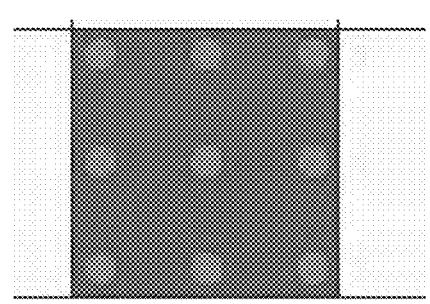

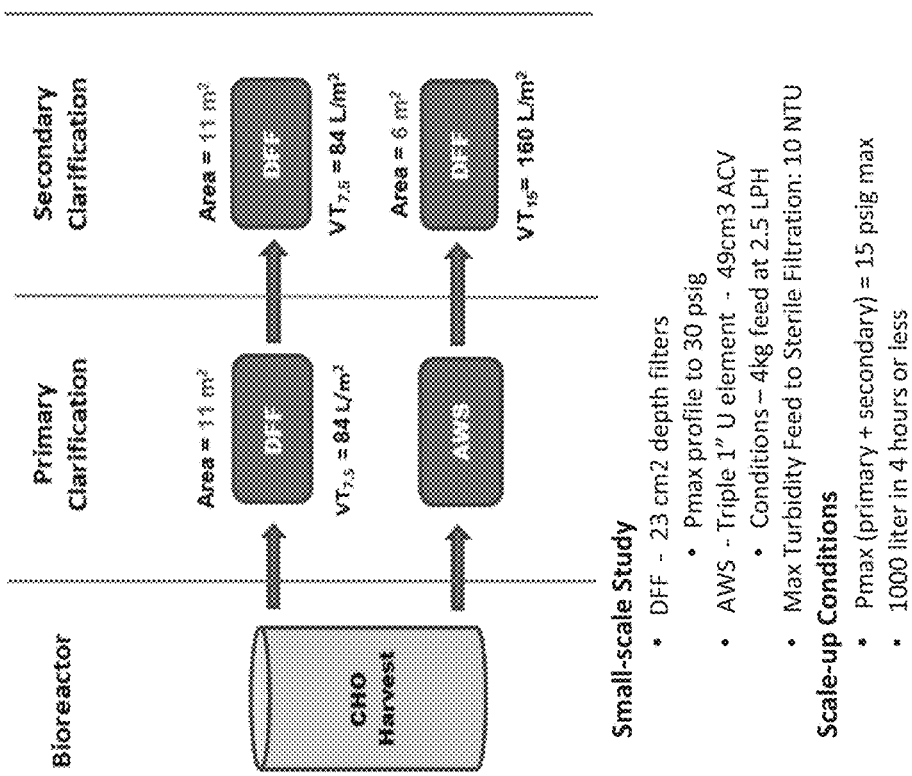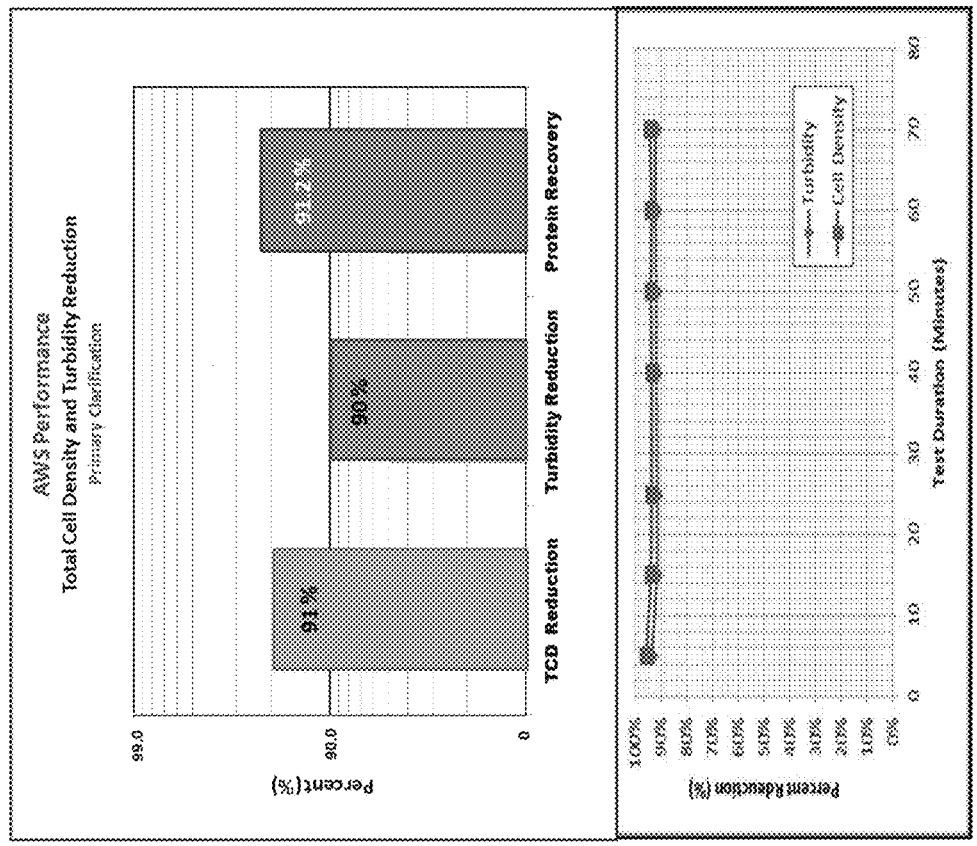
FIG. 39

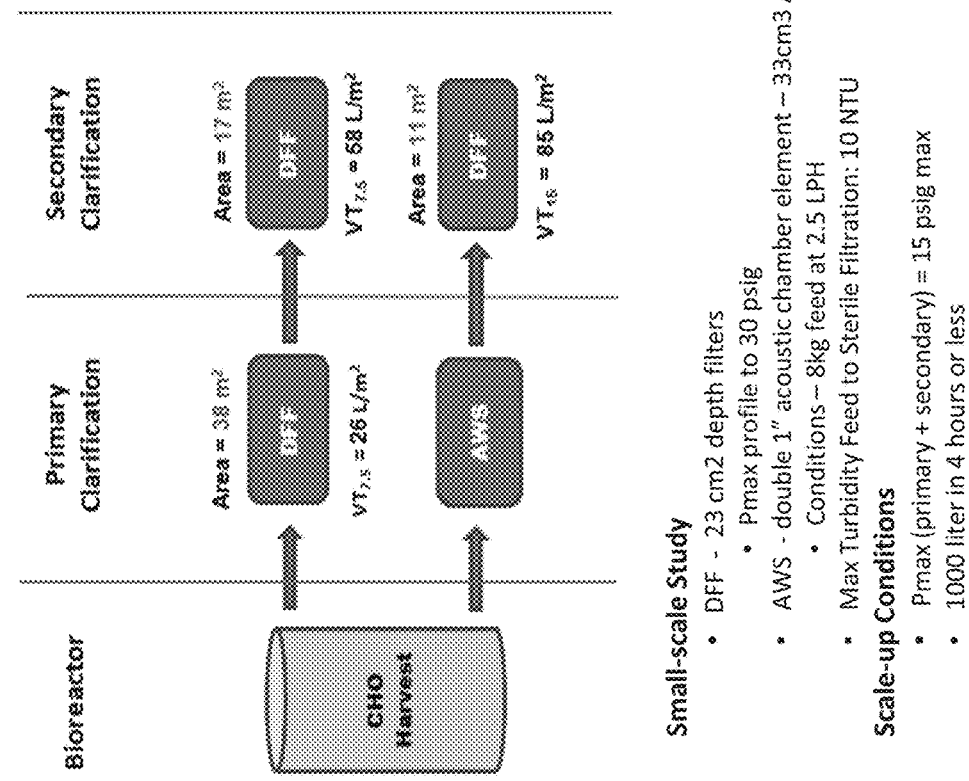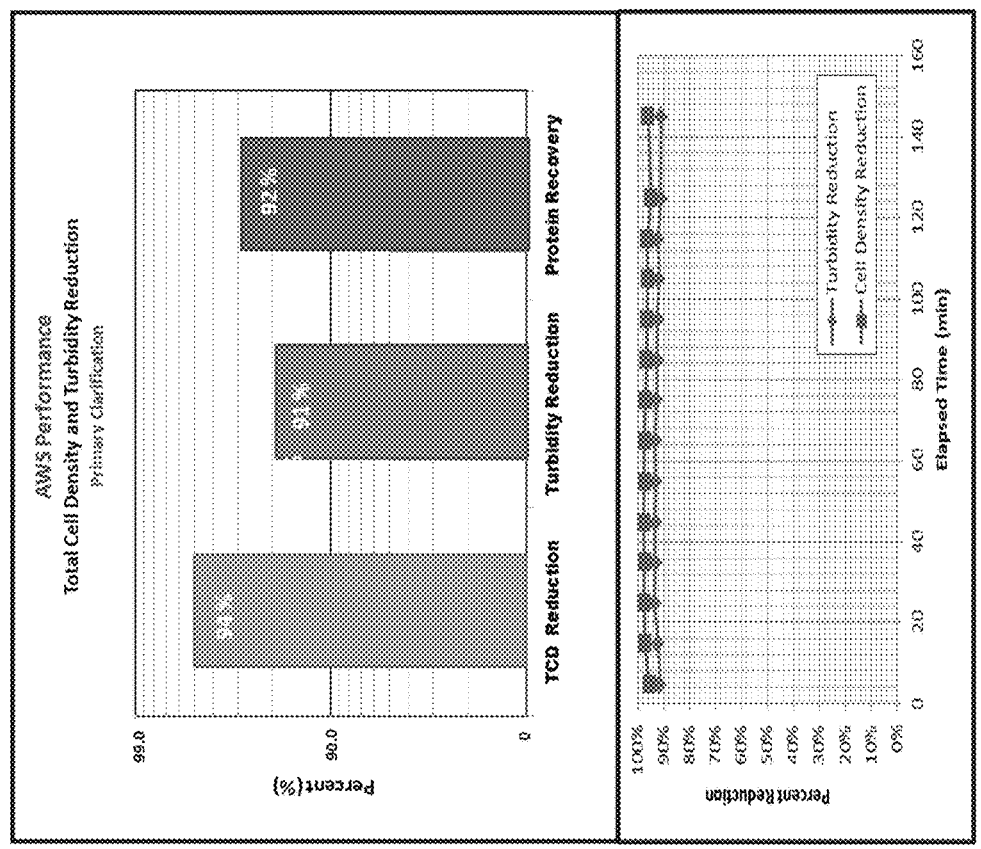
FIG. 40

MULTI-STAGE ACOUSTOPHORESIS DEVICE

CROSS-REFERENCE TO RELATED APPLICATIONS

This application is a continuation-in-part of U.S. patent application Ser. No. 14/533,753, filed on Nov. 5, 2014. U.S. patent application Ser. No. 14/533,753 claimed priority to U.S. Provisional Patent Application Ser. No. 61/900,635, filed Nov. 5, 2013, and to U.S. Provisional Patent Application Ser. No. 62/020,088, filed on Jul. 2, 2014. This application also claims priority to U.S. Provisional Patent Application Ser. No. 62/322,262, filed on Apr. 14, 2016, and to U.S. Provisional Patent Application Ser. No. 62/307,489, filed on Mar. 12, 2016, and to U.S. Provisional Patent Application Ser. No. 62/235,614, filed on Oct. 1, 2015. The disclosures of these applications are hereby fully incorporated by reference in their entirety.

BACKGROUND

The ability to separate a particle/fluid mixture into its separate components is desirable in many applications. Physical size exclusion filters can be used for this purpose, where the particles are trapped on the filter and the fluid flows through the filter. Examples of physical filters include those that operate by tangential flow filtration, depth flow filtration, hollow fiber filtration, and centrifugation. However, physical filters can be complicated to work with. For instance, as the physical filter fills up, filtration capacity is reduced. Also, using such filters requires periodic stopping to remove the filter and obtain or clear the particles trapped thereon.

Acoustophoresis is the separation of particles using high intensity sound waves, and without the use of membranes or physical size exclusion filters. It has been known that high intensity standing waves of sound can exert forces on particles. A standing wave has a pressure profile which appears to "stand" still in time. The pressure profile in a standing wave contains areas of net zero pressure at its nodes and anti-nodes. Depending on the density and compressibility of the particles, they will be trapped at the nodes or anti-nodes of the standing wave. However, conventional acoustophoresis devices have had limited efficacy due to several factors including heat generation, limits on fluid flow, and the inability to capture different types of materials. Improved acoustophoresis devices using improved fluid dynamics would be desirable.

BRIEF SUMMARY

The present disclosure relates to modular components that can be used to build acoustophoretic systems with improved fluid dynamics that can be used to improve separation of particles from a particle/fluid mixture. Either a new mixture with an increased concentration of particles is obtained, or the particles themselves can be obtained or a clarified fluid containing biomolecules, such as recombinant proteins or monoclonal antibodies, may be produces. In more specific embodiments, the particles are biological cells, such as Chinese hamster ovary (CHO) cells, NS0 hybridoma cells, baby hamster kidney (BHK) cells, or human cells; lymphocytes such as T cells (e.g., regulatory T-cells (Tregs), Jurkat T-cells), B cells, or NK cells; their precursors, such as peripheral blood mononuclear cells (PBMCs); algae or other plant cells, bacteria, viruses, or microcarriers. Several different types of modules and overall systems are described herein.

Disclosed in various embodiments herein are modular acoustophoresis devices, comprising an ultrasonic transducer module. The ultrasonic transducer module comprises: a housing defining a primary flow channel between a first end and a second end of the housing; at least one ultrasonic transducer located on a side of the housing; at least one reflector located on the side of the housing opposite the at least one ultrasonic transducer; an first attachment member at the first end of the housing; and a second attachment member at the second end of the housing which may be complementary to the first attachment member.

The first attachment member and the second attachment member of the ultrasonic transducer module may operate by press-fitting or screwing. The attachment members are used to cooperatively fix or fit together the various modules and construct the overall acoustophoretic device.

Some embodiments of the ultrasonic transducer module further include a port on a side of the housing between the transducer and the reflector.

Also disclosed are collection well modules comprising: a housing having a well that tapers downwards in cross-sectional area from a single inlet to a vertex, and a drain line connecting the vertex to a port on a side of the housing; and an attachment member at the inlet, the attachment member adapted to connect the collection well module to the ultrasonic transducer module.

In particular embodiments, the attachment member of the collection well module is complementary to the second attachment member of the ultrasonic transducer module.

Also disclosed are angled collection well modules comprising: a housing having a first opening and a second opening that lead into a common well that taper downwards in cross-sectional area to a vertex, and a drain line connecting the vertex to a port on a side of the housing; a first attachment member at the first opening adapted to connect the collection well module to the ultrasonic transducer module; and a second attachment member at the second opening adapted to connect the collection well module to the ultrasonic transducer module; wherein the first opening is located at an acute angle relative to a base of the housing.

The second opening may be located on the housing opposite the base of the housing. The first attachment member can be complementary to the second attachment member.

Alternative embodiments of a U-turn inlet/outlet module are also disclosed herein, comprising: a housing having an upper end and a lower end; a flow channel having a first end and a second end; an inlet port and an outlet port at the first end of the flow channel; an opening defining the second end of the flow channel and located at the lower end of the housing; and an attachment member at the lower end of the housing, the attachment member adapted to connect the inlet/outlet module to the ultrasonic transducer module; wherein the flow channel is shaped such that fluid flows from the inlet port through the opening and then to the outlet port.

In particular embodiments, the inlet port and the outlet port are spaced from each other on a common side of the housing.

The U-turn inlet/outlet module can further comprise a wall located in the flow channel between the inlet port and the outlet port. The wall can be placed so that a cross-sectional area of the flow channel for the inlet port is smaller than a cross-sectional area of the flow channel for the outlet port. Sometimes, the wall extends out of the opening at the lower end of the housing. In other embodiments, the wall is spaced apart from the upper end of the housing so as to form a pressure relief passage between the inlet port and the outlet port.

In some embodiments, the inlet port and the outlet port are spaced apart from the upper end of the housing such that fluid must flow from the inlet port towards the upper end over a primary retainer wall before exiting through the opening at the lower end of the housing.

In other embodiments, the inlet port and the second port are located at the upper end of the housing, and the flow channel is in the shape of two tubes, one tube leading to the inlet port and the other tube leading to the outlet port.

Also disclosed herein are port modules comprising: a housing defining a single flow channel between an upper end and a lower end of the housing; and an attachment member at the lower end of the housing, the attachment member adapted to connect the port module to the ultrasonic transducer module.

Certain connector modules are also disclosed which comprise: a housing having an upper end, a lower end, and a side; a first opening on the upper end of the housing; a second opening on the side of the housing, a flow channel being defined between the first opening and the second opening; a first attachment member at the upper end of the housing; and a second attachment member at the side of the housing which may be complementary to the first attachment member.

In some particular embodiments, the connector module further comprises: a third opening on the lower end of the housing, the flow channel also joining the first opening and the second opening to the third opening; and a third attachment member at the lower end of the housing which is complementary to the first attachment member.

Also disclosed are other connector modules comprising: a housing having an upper end, a lower end, and a side; a first opening on the upper end of the housing; a second opening on the lower end of the housing, a straight flow channel being defined between the first opening and the second opening; a first attachment member at the upper end of the housing; and a second attachment member at the lower end of the housing, wherein the first attachment member is the same as the second attachment member. These particular connector modules are intended to permit the orientation of a given opening on a different module to be reversed, if needed.

In some embodiments, the first attachment member and the second attachment member are both female members. In other embodiments, the first attachment member and the second attachment member are both male members.

Also disclosed is a variable-volume collection well module comprising: a housing having a well with a constant cross-section, an inlet at an upper end, and a bottom end; and a plunger that provides a floor to the well, the plunger adapted to move through the well from the bottom end towards the upper end. In some further embodiments, this module further includes a port that is on a side of the housing proximate the upper end and fluidly connected to the well.

Also disclosed herein are multi-stage acoustophoretic systems, such as three- and four-stage acoustophoretic systems. These multi-stage acoustophoretic systems can incorporate a filter "train" comprising depth filters, sterile filters, centrifuges, and affinity chromatography columns to purify a cell culture by separating recombinant proteins therefrom. In such systems, the frequency/power of the multi-dimensional acoustic standing wave(s) generated in the system may be varied to send different concentrations or different size materials to subsequent filtration steps in the filter "train," thereby improving the efficiency of the clarification process by effectively managing the material that is processed in each step in the filter "train."

A multi-stage acoustophoretic system according to the present disclosure includes three or more acoustophoretic devices fluidly connected to one another, each acoustophoretic device comprising: a flow chamber having at least one inlet and at least one outlet; at least one ultrasonic transducer located on a wall of the flow chamber, the transducer including a piezoelectric material driven by a voltage signal to create a multi-dimensional standing wave in the flow chamber; and a reflector located on the wall on the opposite side of the flow chamber from the at least one ultrasonic transducer.

The acoustophoretic devices of the multi-stage acoustophoretic system can be fluidly connected to one another by tubing. The acoustophoretic devices of the multi-stage acoustophoretic system can be physically connected directly to one another, either one stage atop another, or side-by-side. The multi-stage acoustophoretic system can include a total of four acoustophoretic devices.

Methods for continuously separating a second fluid or a particulate from a host fluid using a multi-stage acoustophoretic system are also disclosed. All of the multi-dimensional standing wave(s) created in each acoustophoretic device of the multi-stage acoustophoretic system can have different frequencies, or the same frequency, or can have frequencies within the same order of magnitude.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 34A illustrates the trapping line configurations for seven of the peak amplitudes of FIG. 33 from the direction orthogonal to fluid flow.

FIG. 34B is a perspective view illustrating the separator. The fluid flow direction and the trapping lines are shown.

FIG. 34C is a view from the fluid inlet along the fluid flow direction (arrow 114) of FIG. 34B, showing the trapping nodes of the standing wave where particles would be captured.

FIG. 34D is a view taken through the transducers face at the trapping line configurations, along arrow 116 as shown in FIG. 34B.

FIG. 39 is a set of two graphs showing the performance of a second experimental system. The bottom graph has a y-axis of percent reduction, and runs from 0% to 100% in intervals of 10%. The x-axis is test duration in minutes, and runs from 0 to 80 in intervals of 10. The top graph has a y-axis of percent reduction, and is logarithmic, with values of 0, 90%, and 99.0%.

FIG. 40 is a set of graphs showing the performance of a third experimental system. The bottom graph has a y-axis of percent reduction, and runs from 0% to 100% in intervals of 10%. The x-axis is test duration in minutes, and runs from 0 to 80 in intervals of 10. The top graph has a y-axis of percent reduction, and is logarithmic, with values of 0, 90%, and 99.0%.

DETAILED DESCRIPTION

Figure 1:
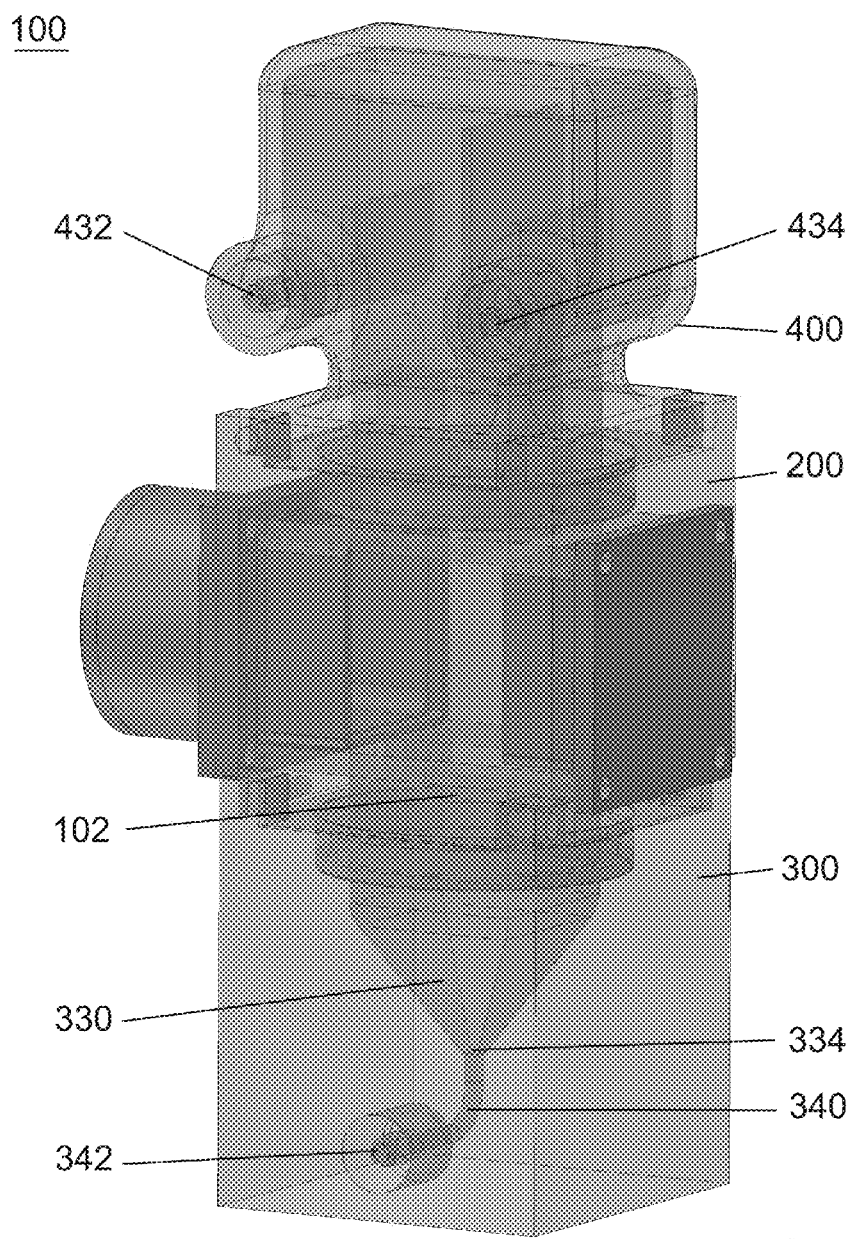
FIG. 1 is an exterior perspective view of a basic acoustophoresis device made from three different modules: an ultrasonic transducer module, a collection well module, and an inlet/outlet module.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

In the figures, interior surfaces are designated by dashed lines in cross-sectional views, unless otherwise noted.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least 1 and less than 10.

The present application also refers to an "acute" angle. For purposes of the present disclosure, the term "acute" refers to an angle between 0° and 90°, exclusive of 0° and 90°.

The acoustophoretic separation technology of the present disclosure employs ultrasonic standing waves to trap, i.e., hold stationary, secondary phase particles in a host fluid stream. This is an important distinction from previous approaches where particle trajectories were merely altered by the effect of the acoustic radiation force. The scattering of the acoustic field off the particles results in a three-dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy and gravitational force, the particle is trapped within the acoustic standing wave field. This results in concentration, agglomeration and/or coalescence of the trapped particles. Additionally, secondary inter-particle forces, such as Bjerkness forces, aid in particle agglomeration. Heavier-than-the-host-fluid (i.e. denser than the host fluid) particles are separated through enhanced gravitational settling.

One specific application for the acoustophoresis device is in the processing of bioreactor materials. It is important to be able to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell cultures including Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the bioreactor.

In this regard, the contrast factor is the difference between the compressibility and density of the particles and the fluid itself. These properties are characteristic of the particles and the fluid themselves. Most cell types present a higher density and lower compressibility than the medium in which they are suspended, so that the acoustic contrast factor between the cells and the medium has a positive value. As a result, the axial acoustic radiation force (ARF) drives the cells, with a positive contrast factor, to the pressure nodal planes, whereas cells or other particles with a negative contrast factor are driven to the pressure anti-nodal planes. The radial or lateral component of the acoustic radiation force helps trap the cells. The radial or lateral component of the ARF is larger than the combined effect of fluid drag force and gravitational force.

As the cells agglomerate at the nodes of the standing wave, there is also a physical scrubbing of the cell culture media that occurs whereby more cells are trapped as they come in contact with the cells that are already held within the standing wave. This generally separates the cells from the cell culture media. The expressed biomolecules remain in the nutrient fluid stream (i.e. cell culture medium).

Desirably, the ultrasonic transducer(s) generate a three-dimensional or multi-dimensional acoustic standing wave in the fluid that exerts a lateral force on the suspended particles to accompany the axial force so as to increase the particle trapping capabilities of the standing wave. Typical results published in literature state that the lateral force is two orders of magnitude smaller than the axial force. In contrast, the technology disclosed in this application provides for a lateral force to be of the same order of magnitude as the axial force.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Three-dimensional (3-D) or multi-dimensional acoustic standing waves are generated from one or more piezoelectric transducers, where the transducers are electrically or mechanically excited such that they move in a multi-excitation mode. The types of waves thus generated can be characterized as composite waves, with displacement profiles that are similar to leaky symmetric (also referred to as compressional or extensional) Lamb waves. The waves are leaky because they radiate into the water layer, which result in the generation of the acoustic standing waves in the water layer. Symmetric Lamb waves have displacement profiles that are symmetric with respect to the neutral axis of the piezoelectric element, which causes multiple standing waves to be generated in a 3-D space. Through this manner of wave generation, a higher lateral trapping force is generated than if the piezoelectric transducer is excited in a "piston" mode where only a single, planar standing wave is generated. Thus, with the same input power to a piezoelectric transducer, the 3-D or multi-dimensional acoustic standing waves can have a higher lateral trapping force which may be up to and beyond 10 times stronger than a single acoustic standing wave generated in piston mode.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

The present disclosure relates to acoustophoresis devices that are made of modular components, and to kits of such modules. The modules include attachment members that are used to cooperatively engage or fit with other modules and can then be reversibly separated. The kits and modules permit the user to make different configurations of acoustophoresis devices as needed to provide for improved settling and improved separation of particles from fluid. Briefly, particles that are suspended in a host fluid can be subjected to multiple transducers generating multiple standing waves in different areas of the separation device to induce separation from the fluid itself. Improved fluid dynamics can also be provided using the modular components, increasing separation of particles from fluid. For example, the fluid stream can be channeled into two or more streams, or the fluid flow can proceed at various angles from 1° up to 90° normal to a base plane.

The use of multiple standing waves from multiple ultrasonic transducers allows for multiple separation stages. For example, in a flow path that runs past two ultrasonic transducers, the first transducer (and its standing wave) will collect a certain amount of the particles, and the second transducer (and its standing wave) will collect additional particles that the first transducer was not able to hold. This construction can be useful where the particle/fluid ratio is high (i.e. large volume of particles), and the separation capacity of the first transducer is reached. This construction can also be useful for particles that have a bimodal or greater size distribution, where each transducer can be optimized to capture particles within a certain size range.

FIG. 1 is an exterior perspective view of a basic acoustophoresis device that can be used for the purposes described above. This basic acoustophoresis device 100 is formed from a kit that includes an ultrasonic transducer module 200, a collection well module 300, and an inlet/outlet module 400. As seen here, the three modules are reversibly interlocked together to form one or more flow paths 102 into which a fluid/particle mixture can be processed to separate the particles from the fluids or to further concentrate the particles within the mixture, and to recover the particles/concentrated mixture.

Briefly, in FIG. 1 the inlet/outlet module 400 contains an inlet port 432 and an outlet port 434 for the flow path. A fluid/particle mixture is pumped in through the inlet port 432. The mixture flows downwards via gravity through the ultrasonic transducer module 200, where the particles are trapped and held by the ultrasonic standing wave. As fluid continues to be pumped into the flow path, eventually the collection well module 300 and the ultrasonic transducer module 200 are filled with fluid, and the fluid pressure rises high enough that fluid will flow out through the outlet port 434 at the top of the device. The particles within the ultrasonic standing wave collect or agglomerate, and eventually grow to a size where gravity overcomes the acoustic force of the standing wave, and the particle aggregates then fall/sink into the collection well module 300. The collection well module includes a well 330 that tapers downwards in cross-sectional size to a vertex 334. A drain line 340 connects the vertex 334 to a port 342 where the concentrated particles can be drawn out of the well.

Figure 2:
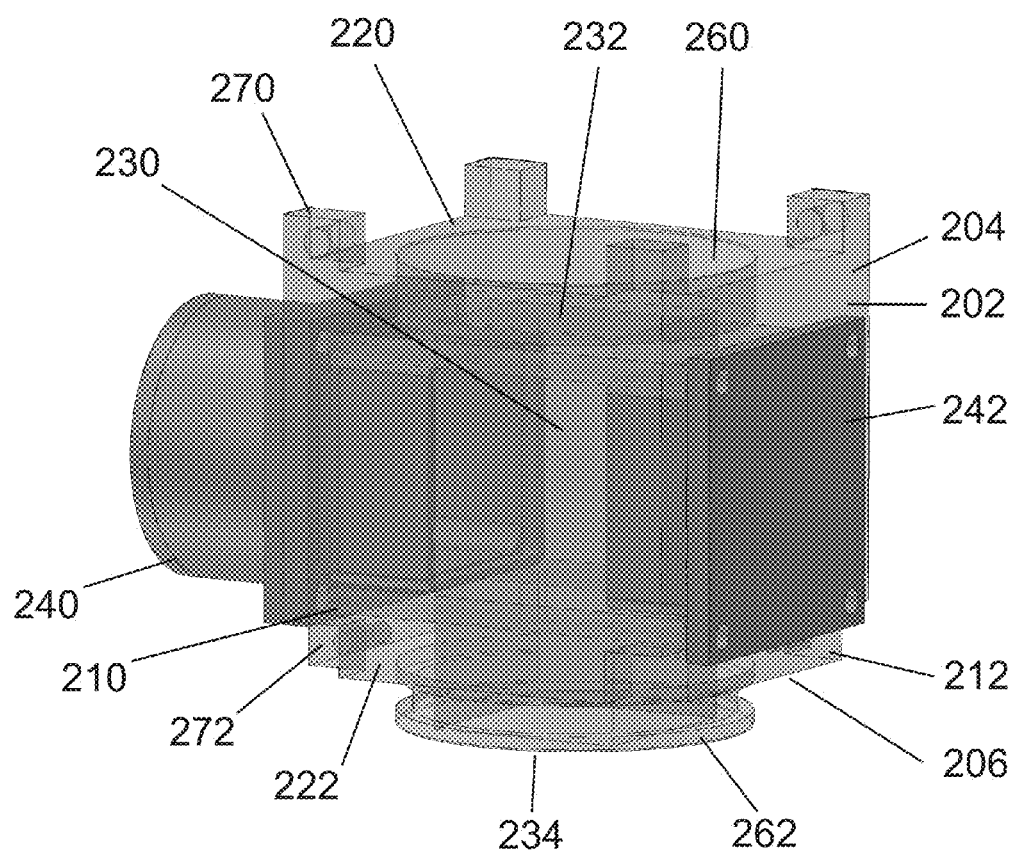
FIG. 2 is a perspective view of the ultrasonic transducer module of FIG. 1.

FIG. 2 is a perspective view of the ultrasonic transducer module of FIG. 1. The ultrasonic transducer module 200 includes a housing 202 having a first end 204 and a second end 206 which are located at opposite ends of the housing. Here, the housing is in the shape of a cube having four side walls 210, 212 (third and fourth walls not visible), 216, a first wall 220, and a second wall 222. However, the exterior shape of the module is not particularly relevant, and could be for example cylindrical. The first end and the second end of the housing can be considered as defining a z-axis. The four opposing side walls can be considered as corresponding to opposite directions along the x-y axes of the housing.

A flow channel 230 is defined between the first end 204 and the second end 206 of the housing. Put another way, an opening 232, 234 is present in both the first wall and the second wall, and a bore joins the two openings together, such that fluid can flow through the housing from between the first end and the second end. As illustrated here, the bore has a rectangular (e.g. square) cross-section. An ultrasonic transducer 240 is located on one side of the housing, and the reflector 242 is located on the side of the housing opposite the ultrasonic transducer. It should be noted that the ultrasonic transducer is directly adjacent to the flow channel, and would be directly exposed to any fluid passing through the flow channel. The reflector is solid or flexible, and can be made of a high acoustic impedance material such as steel or tungsten, providing good reflection.

A first attachment member 260 is disposed at the first end 204 of the housing, i.e. on the first wall 220 of the housing. A second attachment member 262 is disposed at the second end 206 of the housing, i.e. on the second wall 222 of the housing. These attachment members are intended to permit the module to be reversibly joined with other modules and form a water-tight seal. As illustrated here, the second attachment member is complementary to the first attachment member. The second attachment member is a male member (e.g. a tongue), and the first attachment member is a female member (e.g. a hole). An o-ring (not shown) is present on the second attachment member to ensure the seal. The first end 204 of the housing also includes four tenons 270, one located at each corner, and the second end 206 includes four mortises 272, again located at each corner. The depicted attachment members are intended to be press-fitted together. Of course, other reversible attachment means are contemplated, for example attachment members that include internal or external threads, so that modules are screwed together. The attachment members could also be reversed in location (e.g. the first attachment member is male, and the second attachment member is female). These attachment members can also be described as surrounding the openings in the first wall and second wall.

Figure 3:
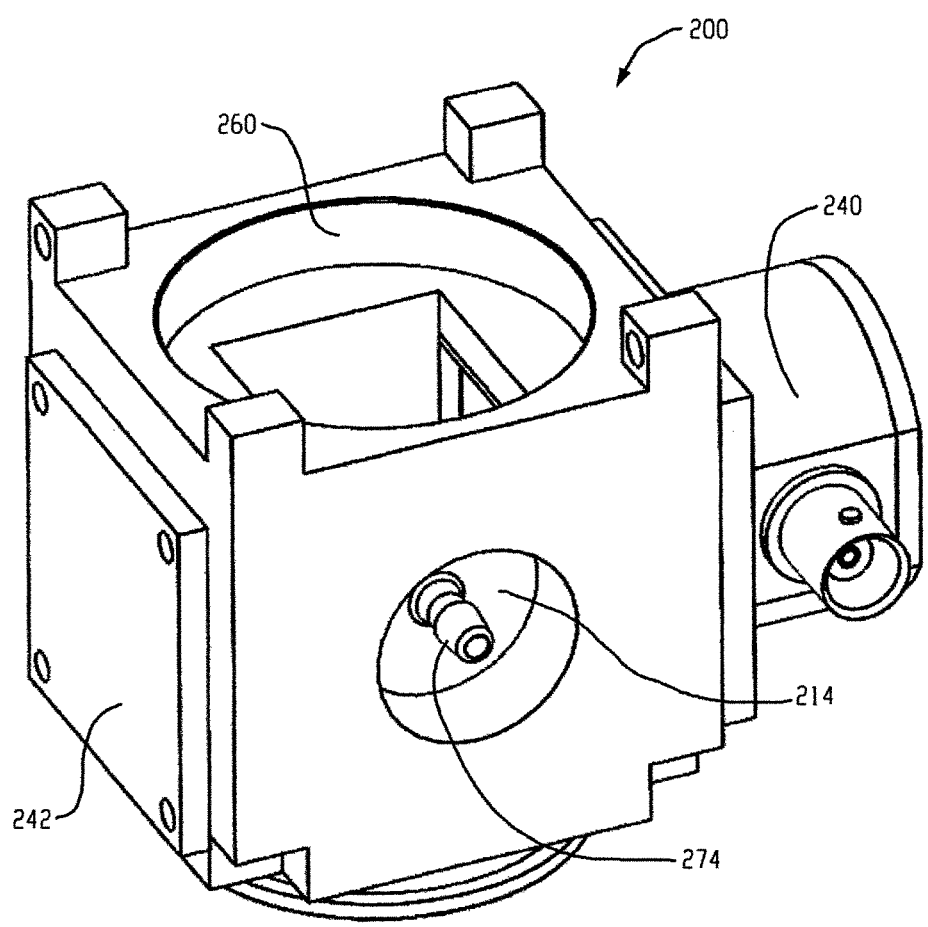
FIG. 3 is a perspective view of an exemplary ultrasonic transducer module in which an additional port is included between the ultrasonic transducer and the reflector.

In some embodiments of the ultrasonic transducer module, as seen in FIG. 3, an additional port 274 can be included on a side 214 of the housing between the transducer 240 and the reflector 242. This may be useful for injecting fluid into the particles trapped by the acoustic standing wave, or for collecting particles directly from the acoustic standing wave.

Figure 4:
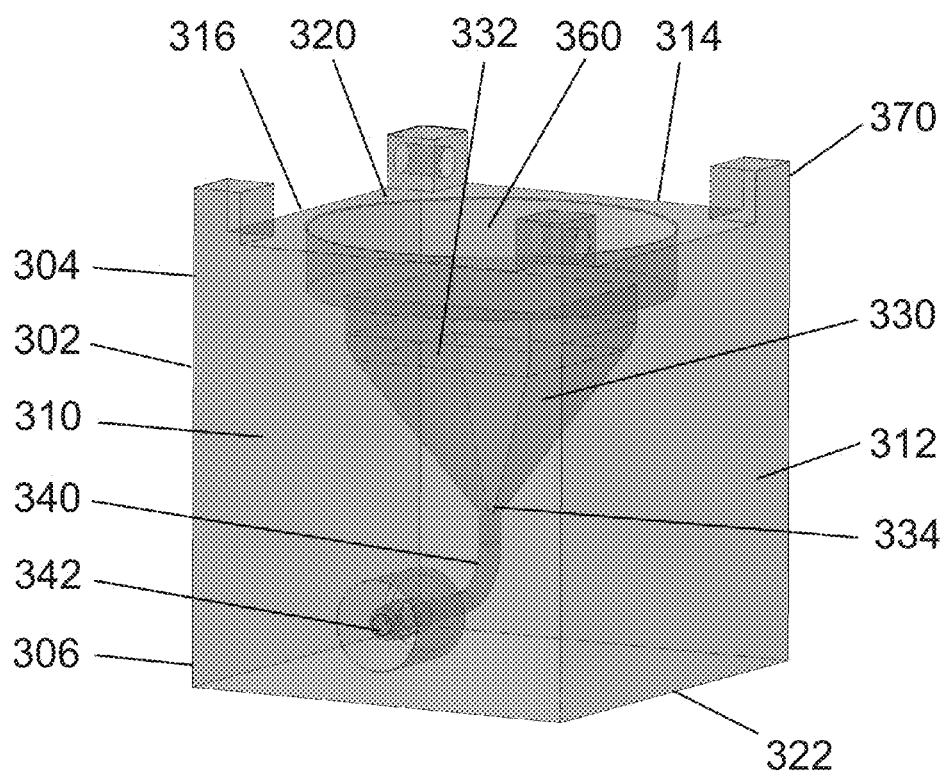
FIG. 4 is a perspective view of the collection well module of FIG. 1.

FIG. 4 is a perspective view of the collection well module of FIG. 1. The collection well module 300 includes a housing 302 having an upper end 304 and a lower end 306. As illustrated, the housing is in the shape of a cube having four sides, an upper wall 320, and a lower wall 322. More generally, the upper end and the lower end of the housing are located at opposite ends of the housing, and can be considered as defining a z-axis. The housing also has four opposing sides 310, 312, 314, 316, which can be considered as corresponding to opposite directions along the x-y axes of the housing. Again, the exterior shape of the module is not particularly relevant. However, it is noted that the collection well module is usually located at the bottom of the overall acoustophoretic device, and so the lower wall usually provides a base for the device and should be flat.

An inlet 332 is present in the upper end/upper wall of the housing, and is intended to receive particles and fluid. As illustrated here, the inlet has a rectangular (e.g. square) cross-section. A well 330 is present in the housing, which tapers downwards in cross-sectional area from the inlet 332 to a vertex 334. The inlet forms one end of the well, and the vertex forms the other end of the well. A drain line 340 connects the vertex 334 to a port 342 on a side of the housing, from which a concentrated particle/fluid mixture can flow out of the well 330 to the port. It is noted that because the lower wall acts as a base, the port is located on one of the four opposing sides of the housing. It should be noted that this collection well module has only one inlet 332, i.e. does not have two or more inlets. Also, the well is depicted here with the inlet 332 and the vertex 334 being concentric, i.e. when viewed from the top, the vertex is in the center of the inlet. However, this concentricity is not required. For example, the vertex could be skewed to the side to minimize the length of the drain line.

An attachment member 360 is disposed at the upper end 304 of the housing, i.e. on the upper wall of the housing, and again is intended to permit the module to be reversibly joined with other modules and form a water-tight seal. As illustrated here, the attachment member is a female member (e.g. a hole). In addition, the upper end of the housing also includes four tenons 370 at each corner. Here, the attachment member of the collection well module is complementary to the lower attachment member of the ultrasonic transducer module. Again, the attachment member can also be described as surrounding the inlet.

Figure 5:
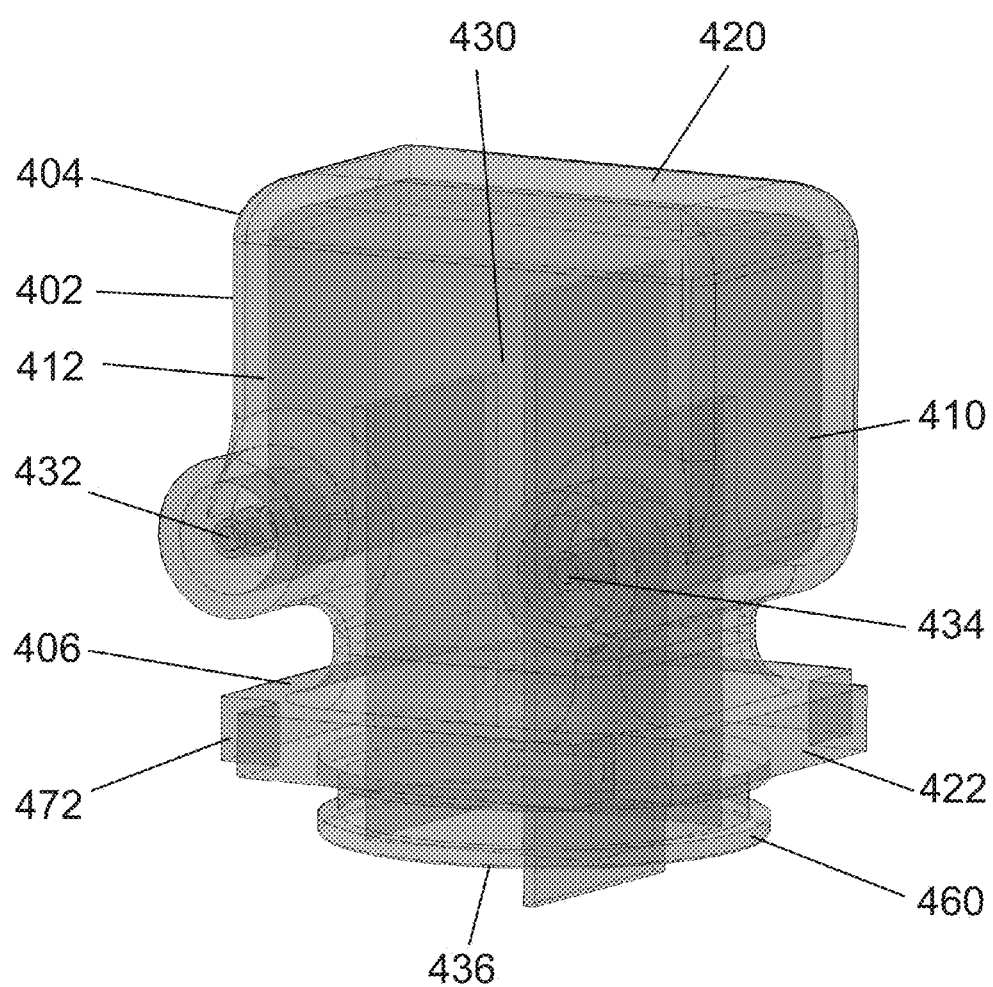
FIG. 5 is a perspective view of the inlet/outlet module of FIG. 1. Here, the inlet port and the outlet port are located on a front wall of the module.
Figure 6:
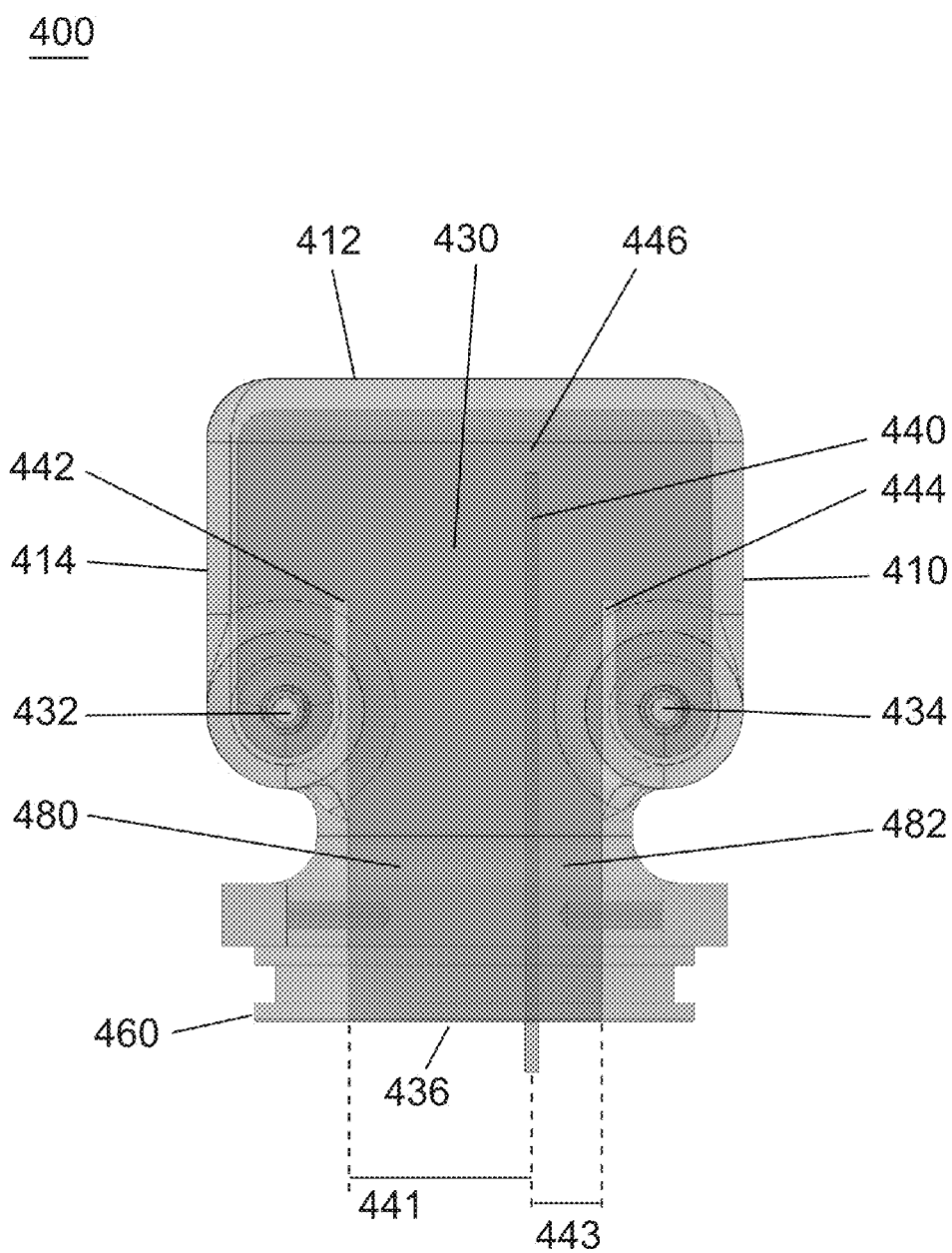
FIG. 6 is a front view of the inlet/outlet module of FIG. 5.

FIG. 5 is a perspective view of the inlet/outlet module of FIG. 1. FIG. 6 is a front view of the inlet/outlet module. In this regard, the inlet/outlet module 400 is adapted to both introduce a particle/fluid mixture into the flow path, as well as to expel/remove fluid from the flow path. The inlet/outlet module 400 includes a housing 402 having an upper end 404 and a lower end 406. As illustrated, the housing generally has an upper wall 420, a lower wall 422, and at least one side wall 410 extending between them. The upper end and the lower end of the housing are located at opposite ends of the housing, and can be considered as defining a z-axis. The housing also has four opposing sides 410, 412, 414 (fourth wall not visible), which can be considered as corresponding to opposite directions along the x-y axes of the housing. Again, the exterior shape of the module is not particularly relevant.

The inlet/outlet module includes an inlet port 432 and an outlet port 434, which are illustrated here as being spaced apart from each other on a common side of the housing (i.e. front wall 412). An opening 436 is present at the lower end 406 of the housing (i.e. in the lower wall). A flow channel 430 is defined by the inlet port 432, the outlet port 434, and the opening 436. The inlet port and the outlet port are located at a first end of the flow channel, and the opening is located at the second end of the flow channel.

As best seen in FIG. 6, a wall 440 is located in the flow channel 430 between the inlet port 432 and the outlet port 434. Due to the presence of the wall, as explained above in the discussion of FIG. 1, fluid flows from the inlet port through the opening and then to the outlet port. The wall essentially divides the flow channel into two separate sub-channels, the ends of one sub-channel 480 being identified by the inlet port 432 and the opening 436, and the ends of the other sub-channel 482 being identified by the outlet port 434 and the opening 436. The cross-sectional area of the flow channel for the inlet port can be smaller than, equal to, or greater than the cross-sectional area of the flow channel for the outlet port. As illustrated in FIG. 6, the wall is placed so that the cross-sectional area 441 of the flow channel for the inlet port is smaller than the cross-sectional area 443 of the flow channel for the outlet port.

Also visible in FIG. 6 is a first retainer wall 442 adjacent the inlet port and a second retainer wall 444 adjacent the outlet port. As seen here, the inlet port 432 and the outlet port 434 are located relatively close to the middle of the front wall, and are spaced apart from the upper end 404 of the housing. Incoming fluid must flow towards the upper end 404 and then over the first retainer wall 442 before exiting through the opening 436. Similarly, fluid coming back from the ultrasonic transducer module must flow from the opening 436 over the second retainer wall 444 before exiting through the outlet port 434. This construction provides a means by which the turbulence of incoming fluid can be reduced, so that the particles trapped in the acoustic standing wave in the ultrasonic transducer module are not disrupted or washed out of the standing wave before aggregating to a sufficient size.

In some embodiments such as the one depicted here, the wall 440 extends out of the opening 436 at the lower end of the housing. This helps ensure that the incoming particle/fluid mixture passes through the ultrasonic transducer module before fluid exits the flow path (of the overall acoustophoresis device) through the outlet port.

As also depicted here, in some embodiments, the wall 440 is spaced apart from the upper end 404/upper wall 420 of the housing. This gap 446 forms and acts as a pressure relief passage between the inlet port 432 and the outlet port 434, for example in case the flow path is inadvertently blocked.

Continuing with FIG. 6, an attachment member 460 is disposed at the lower end 406 of the housing, i.e. on the lower wall of the housing, and again is intended to permit the module to be reversibly joined with other modules and form a water-tight seal. As illustrated here, the attachment member is a male member (e.g. a tongue). An o-ring (not shown) is used on the attachment member to ensure the seal. Four mortises 472 are also present, one at each corner on the lower end of the housing.

Besides the three modules described above, additional modules are contemplated that can be used to form an acoustophoretic system as described above. These modules include an angled collection well module 500, another inlet/outlet module 600, a port module 700, various connector modules 800, and transducer modules combined with an improved separation system 900. These various modules will now be described.

Figure 7:
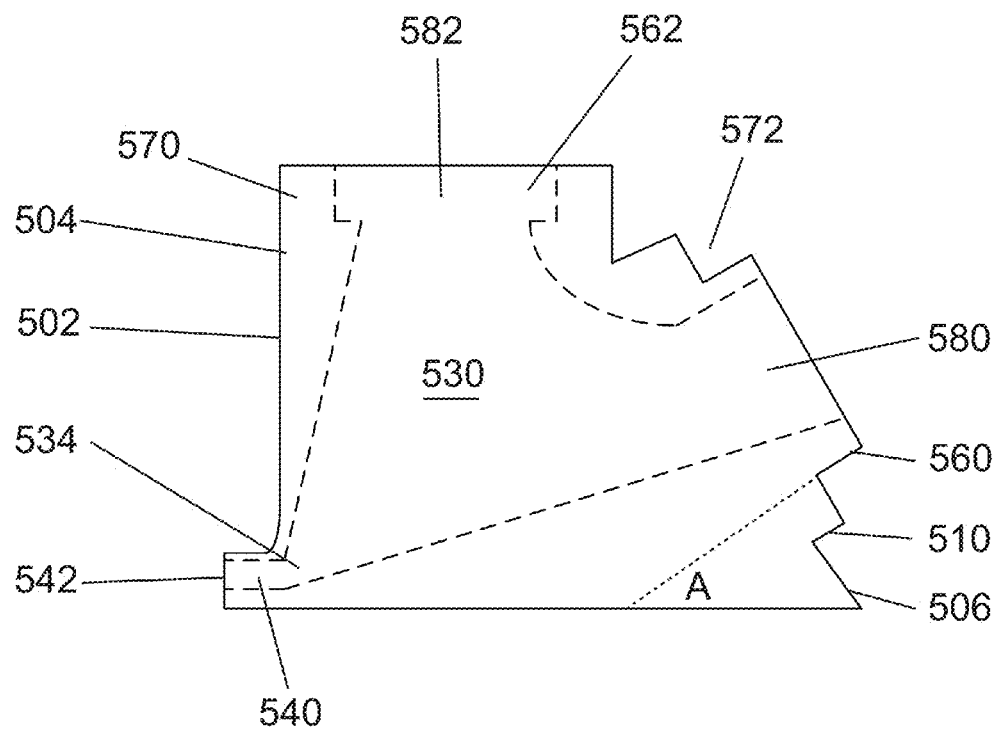
FIG. 7 is a front view of an angled collection well module.

FIG. 7 is a front view of an angled collection well module 500. The angled collection well module includes a housing 502 having an upper end 504 and a lower end 506. The exterior shape of the module is not particularly relevant. More generally, the upper end and the lower end of the housing are located at opposite ends of the housing, and can be considered as defining a z-axis. The lower end 506 defines a base of the housing.

This module has a first opening 580 and a second opening 582. At least one of the openings is located at an acute angle relative to the base of the housing. This is indicated on FIG. 7 with the first opening having an angle A (dotted line). The first opening 580 can be described as being located on a side 510 of the housing. Here, the second opening 582 is located opposite the base of the housing, i.e. on the upper end 504 of the housing. However, it is also contemplated that the second opening could also be located at an acute angle relative to the base of the housing.

The first opening 580 and the second opening 582 both lead into a common well 530 that tapers downwards in cross-sectional area from the openings to a vertex 534 (interior surface shown in dashed lines). A drain line 540 connects the vertex 534 to a port 542 on a side of the housing, from which a concentrated particle/fluid mixture can drain from the well 530 to the port 542 and out of the collection module. Because the lower wall acts as a base, the port is located on a side of the housing. In particular embodiments, the angled collection well module has only two openings 580, 582. In other embodiments, the angled collection well module has at least two openings located at an acute angle relative to the base of the housing, with all openings leading into the common well 530.

A first attachment member 560 is located at the first opening 580. A second attachment member 562 is located at the second opening 582. Each attachment member can also be described as surrounding the opening. The attachment members are intended to permit the module to be reversibly joined with other modules and form a water-tight seal. As illustrated here, the first attachment member is a male member (e.g. a tongue), and the second attachment member is a female member (e.g. a hole). An o-ring (not shown) is present on the first attachment member to ensure the seal. In addition, the second opening 582 also includes four tenons 570, one located at each corner. The first opening 580 also includes four mortises 572, again located at each corner. In particular embodiments, the first attachment member is complementary to the second attachment member, and they are also adapted to engage and interlock with the ultrasonic transducer module.

Figure 8:
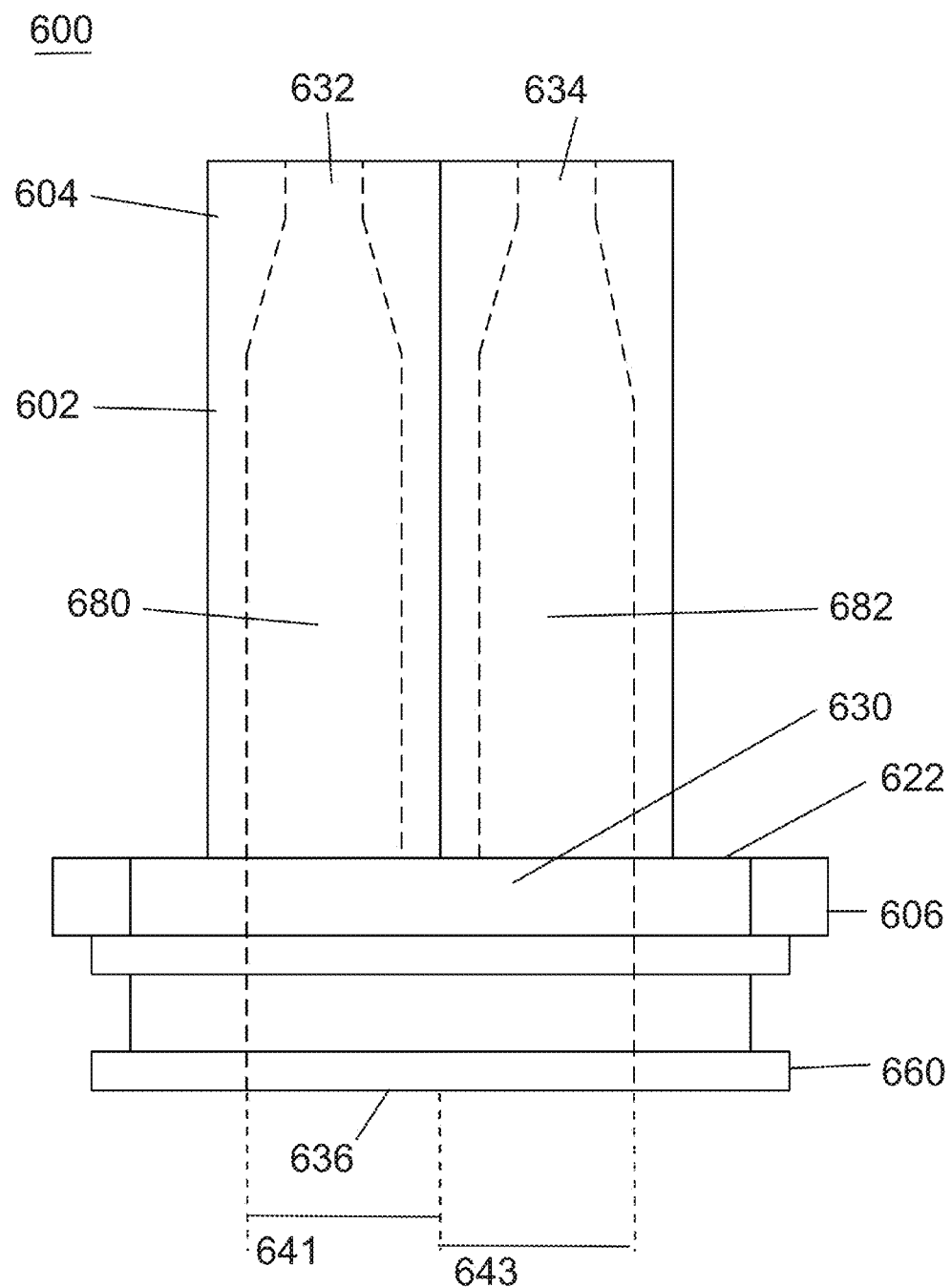
FIG. 8 is a front view of a second exemplary inlet/outlet module. Here, the inlet port and the outlet port are located at the upper end of the housing.

FIG. 8 is a front view of an alternative embodiment of the inlet/outlet module. Similar to the module of FIG. 5, the inlet/outlet module 600 includes a housing 602 having an upper end 604 and a lower end 606 which are located at opposite ends of the housing. The housing generally has a lower wall 622. An opening 636 is present at the lower end of the housing (i.e. in the lower wall, interior surface denoted by dashed lines). The inlet/outlet module also includes an inlet port 632 and an outlet port 634. A flow channel 630 is defined by the inlet port 632, the outlet port 634, and the opening 636. In this embodiment, the inlet port 632 and the outlet port 634 are located at the upper end 604 of the housing. The inlet port and the outlet port are located at a first end of the flow channel, and the opening is located at the second end of the flow channel. The flow channel here is in the shape of two tubes 680, 682, each tube acting as a sub-channel. One tube 680 runs between the inlet port 632 and the opening 636. The other tube 682 runs between the outlet port 634 and the opening 636. Again, the cross-sectional area 641 of the tube for the inlet port can be smaller than, equal to, or greater than the cross-sectional area 643 of the tube for the outlet port. As illustrated here, the cross-sectional areas of the two tubes are equal. An attachment member 660 is present at the lower end 606, here illustrated as a male member (e.g. tongue).

Figure 9:
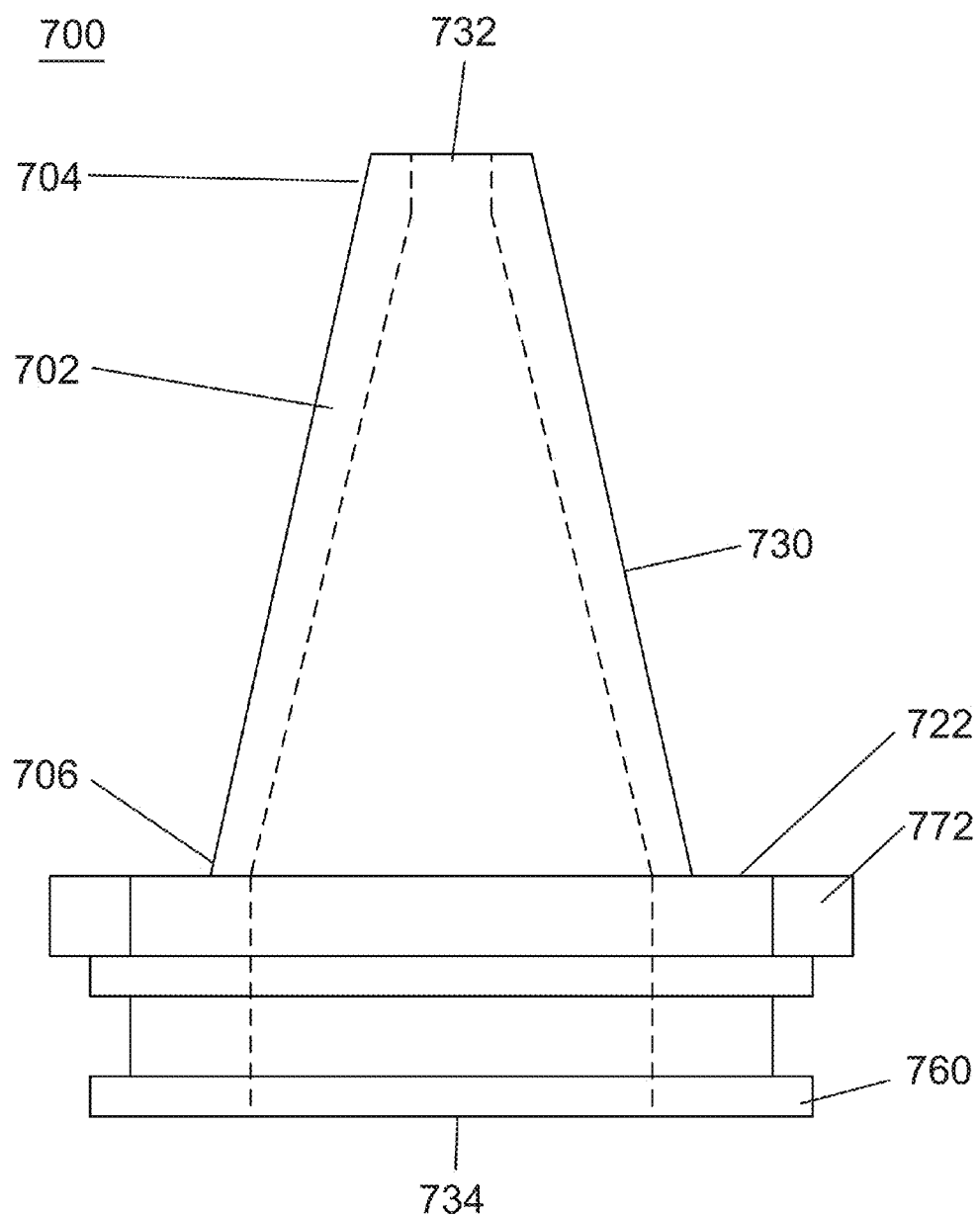
FIG. 9 is a front view of an exemplary port module that functions as an inlet or an outlet, but not both at the same time. Put another way, fluid only flows in one direction through the port module.

FIG. 9 is a front view of a port module 700 that can be combined with the other modules of the present disclosure. The port module 700 includes a housing 702 having an upper end 704 and a lower end 706 which are located at opposite ends of the housing. As illustrated here, the port module is in the shape of a cone with a plate 722 on the lower end. Again, though, the exterior shape is not particularly relevant. A flow channel 730 is defined between the upper end 704 and the lower end 706 of the housing (indicated by dashed lines). Put another way, an opening 732, 734 is present at both the upper end and the lower end, and a bore joins the two openings together, such that fluid can flow through the housing from between the upper end and the lower end. Here, the flow channel is in the shape of a cone, which acts as a diffuser. In contrast to the inlet/outlet module of FIG. 5 and FIG. 8, the flow channel of the port module allows fluid flow in only one direction. The port module can function as an inlet or an outlet, but not both at the same time. Put another way, the flow channel is not made of sub-channels.

The port module 700 also includes an attachment member 760 at the lower end of the housing for joining the port module to other modules and forming a water-tight seal. As illustrated here, the attachment member is a male member (e.g. a tongue), with an o-ring (not shown) on the attachment member to ensure the seal. In addition, four mortises 772 are present, one at each corner on the lower end of the housing.

Figure 10:
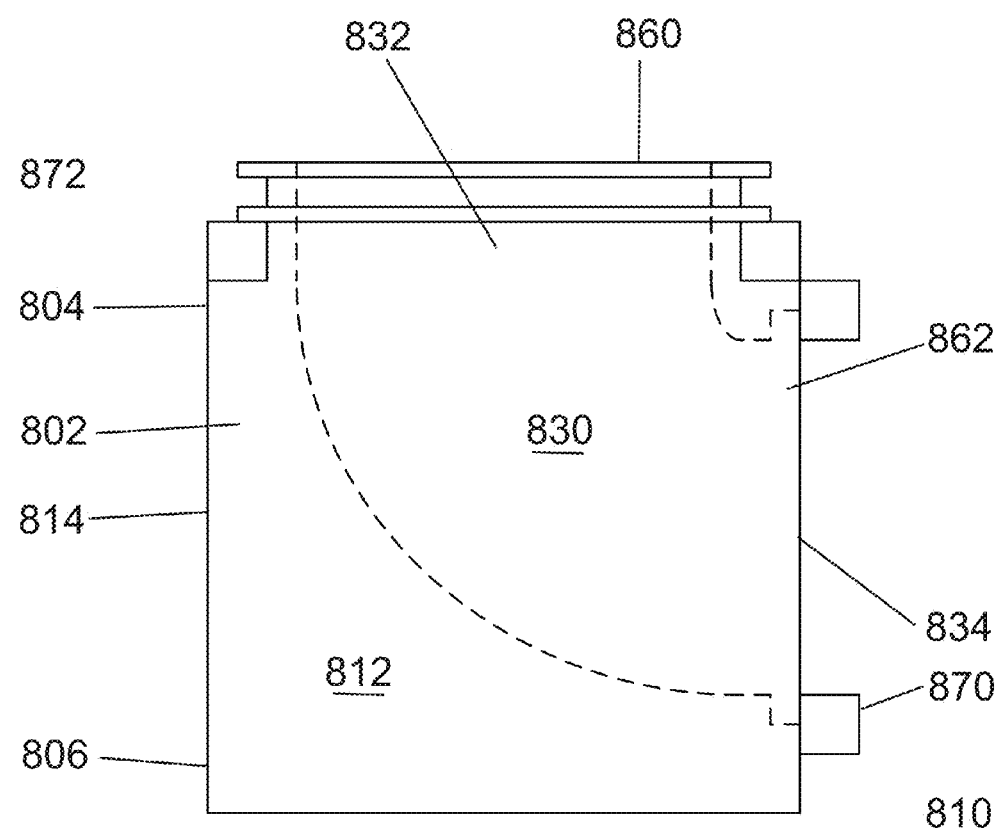
FIG. 10 is a front view of a first exemplary two-way connector module. The flow channel in this connector module makes a 90° curve.

FIG. 10 is a front view of an exemplary two-way connector module 800. The connector module 800 includes a housing 802 having an upper end 804 and a lower end 806 which are located at opposite ends of the housing. Again, generally, the upper end and the lower end of the housing can be considered as defining a z-axis. The housing also has four opposing sides 810, 812, 814 (fourth side not visible), which can be considered as corresponding to opposite directions along the x-y axes of the housing.

This module has a first opening 832 and a second opening 834. One opening is present in the upper end 804 of the housing, and the other opening is present in a side 810 of the housing. A flow channel 830 is defined between the two openings, with a bore joining the two openings together to permit fluid to flow through the housing between the two openings (indicated by dashed lines). As seen here, the flow channel is curved about 90°.

A first attachment member 860 is located at the first opening 832. A second attachment member 862 is located at the second opening 834. Each attachment member can also be described as surrounding the opening. The attachment members are intended to permit the connector module to be reversibly joined with other modules and form a water-tight seal. As illustrated here, the first attachment member 860 is a male member (e.g. a tongue), and the second attachment member 862 is a female member (e.g. a hole). An o-ring (not shown) is present on the first attachment member to ensure the seal. In addition, the second opening 834 also includes four tenons 870, one located at each corner. The first opening 832 also includes four mortises 872, again located at each corner. In particular embodiments, the first attachment member 860 is complementary to the second attachment member 862, and they are also adapted to engage and interlock with the ultrasonic transducer module 200.

Figure 11:
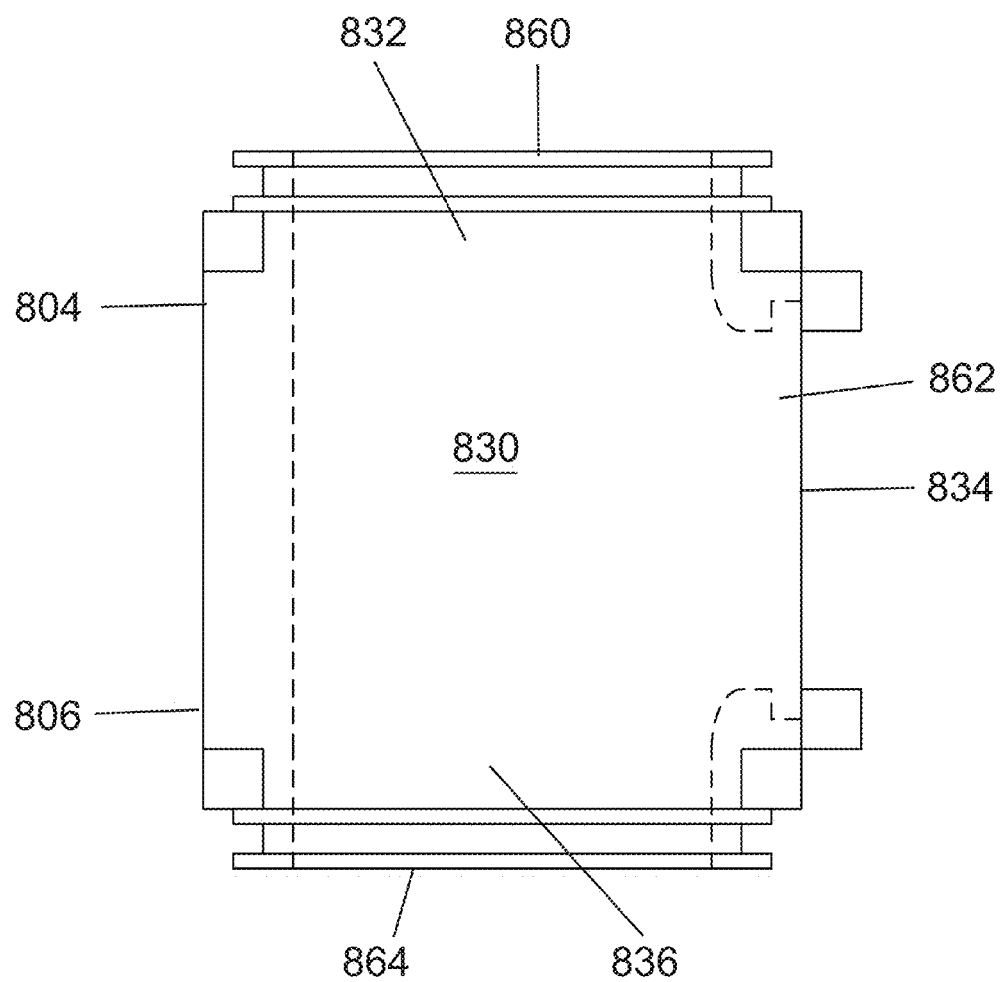
FIG. 11 is a front view of an exemplary three-way connector module. This connector module has a total of three openings. Two openings are on opposite ends of the connector module. The third opening is located on a side of the connector module between the two ends.

The connector 800 of FIG. 10 has only two openings. FIG. 11 is a front view of a three-way connector module 892. This connector module has a total of three openings. The structure of this connector module is very similar to the structure 800 of FIG. 10. The only addition is the inclusion of the third opening 836 in the lower end 806 of the housing 802. A third attachment member 864 is also present at the lower end 806 of the housing. As a result, the flow channel 830 is T-shaped, permitting flow between any combination of the three openings 832, 834, 836. In specific embodiments, the third attachment member 864 is complementary to the first attachment member 860, and is not complementary to the second attachment member 862. In other embodiments, the third attachment member 864 is complementary to the second attachment member 862, and is not complementary to the first attachment member 860.

Figure 12:
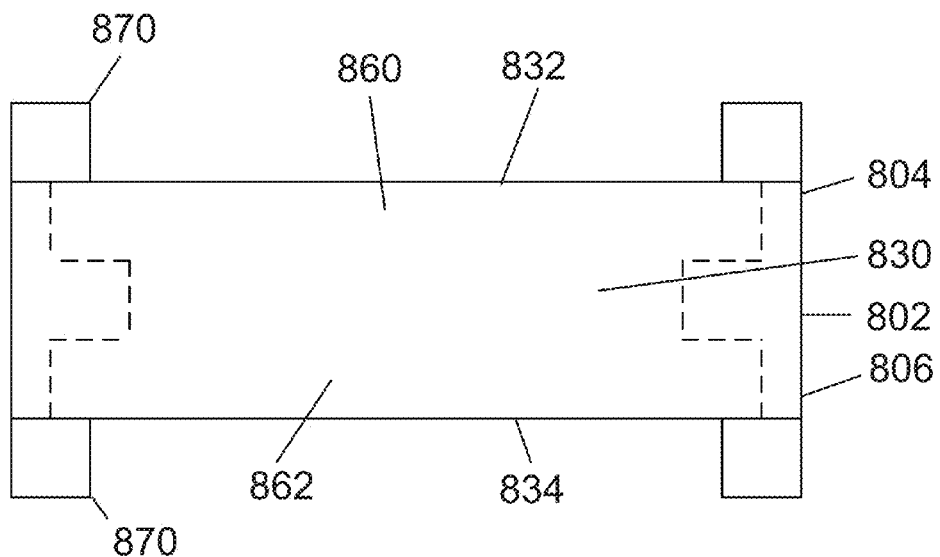
FIG. 12 is a front view of a second exemplary two-way connector module. The flow channel in this connector module is straight. Two attachment members are present, and both are of the same structure. Here, both are female members.

FIG. 12 is a front view of another two-way connector module 894. This connector module includes a housing 802 having an upper end 804 and a lower end 806 which are located at opposite ends of the housing. The module also has a first opening 832 and a second opening 834. One opening 832 is present in the upper end 804 of the housing, and the other opening 834 is present in the lower end 806 of the housing. A flow channel 830 is defined between the two openings (indicated with dashed lines), with a bore joining the two openings together to permit fluid to flow through the housing between the two openings.

A first attachment member 860 is located at the first opening 832. A second attachment member 862 is located at the second opening 834. Each attachment member can also be described as surrounding the opening. The two attachment members are of the same type and structure. Here, the two attachment members 860, 862 are female (e.g. a hole). In addition, each opening also includes four tenons 870, one located at each corner.

Figure 13:
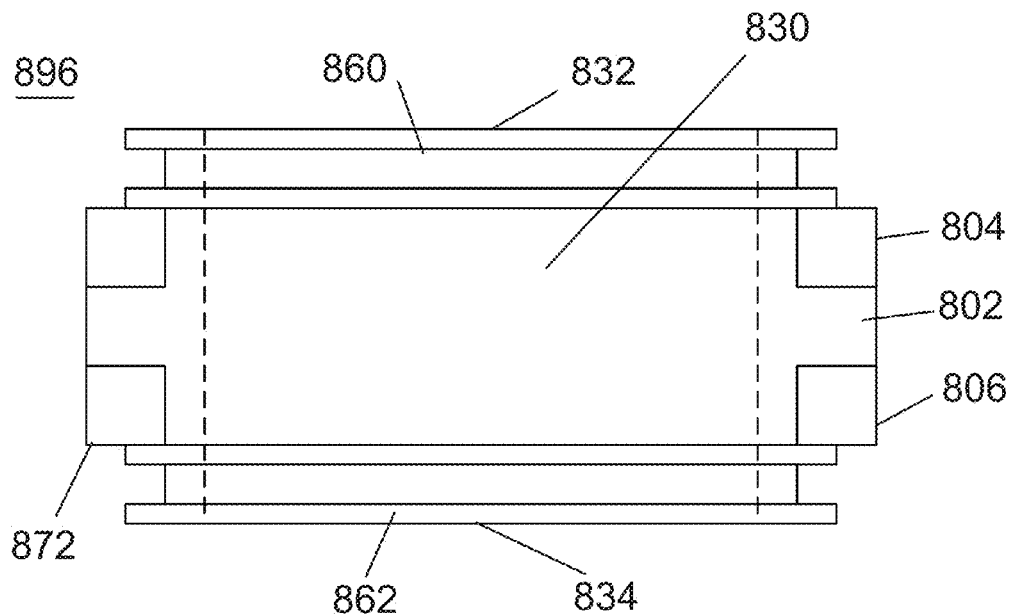
FIG. 13 is a front view of another exemplary two-way connector module similar to FIG. 12, except that the attachment members are male members.

FIG. 13 is a perspective view of a third two-way connector module 896. This embodiment is similar to the connector module 894 of FIG. 12, except the two attachment members 860, 862 are male (e.g. a tongue). In addition, each opening also includes four mortises 872, again located at each corner.

The connector modules of FIG. 12 and FIG. 13 are intended to permit the orientation of a given opening on a different module to be reversed. The utility of such connectors will be shown later.

Figure 14:
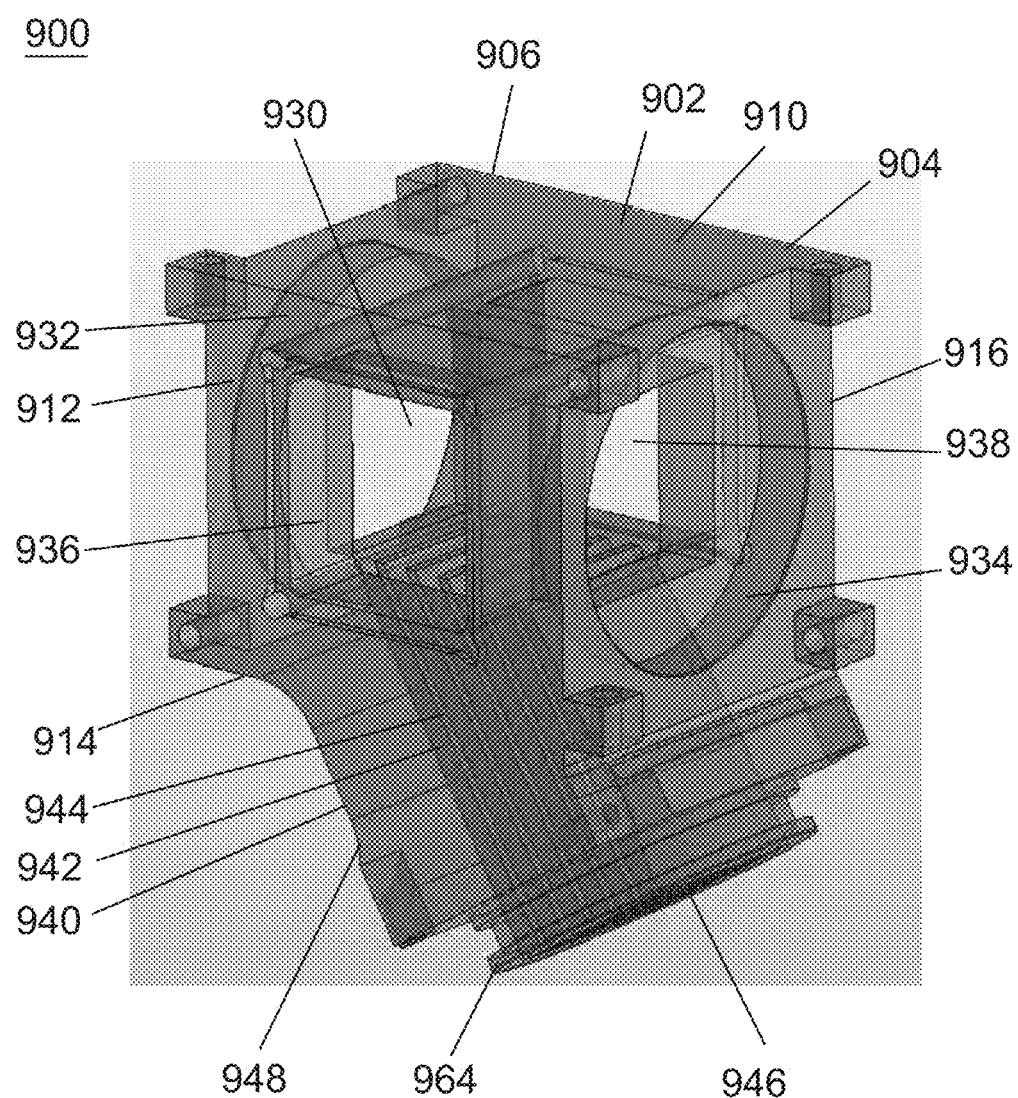
FIG. 14 is a perspective view of an ultrasonic transducer module that incorporates a separation system formed from baffles.
Figure 15:
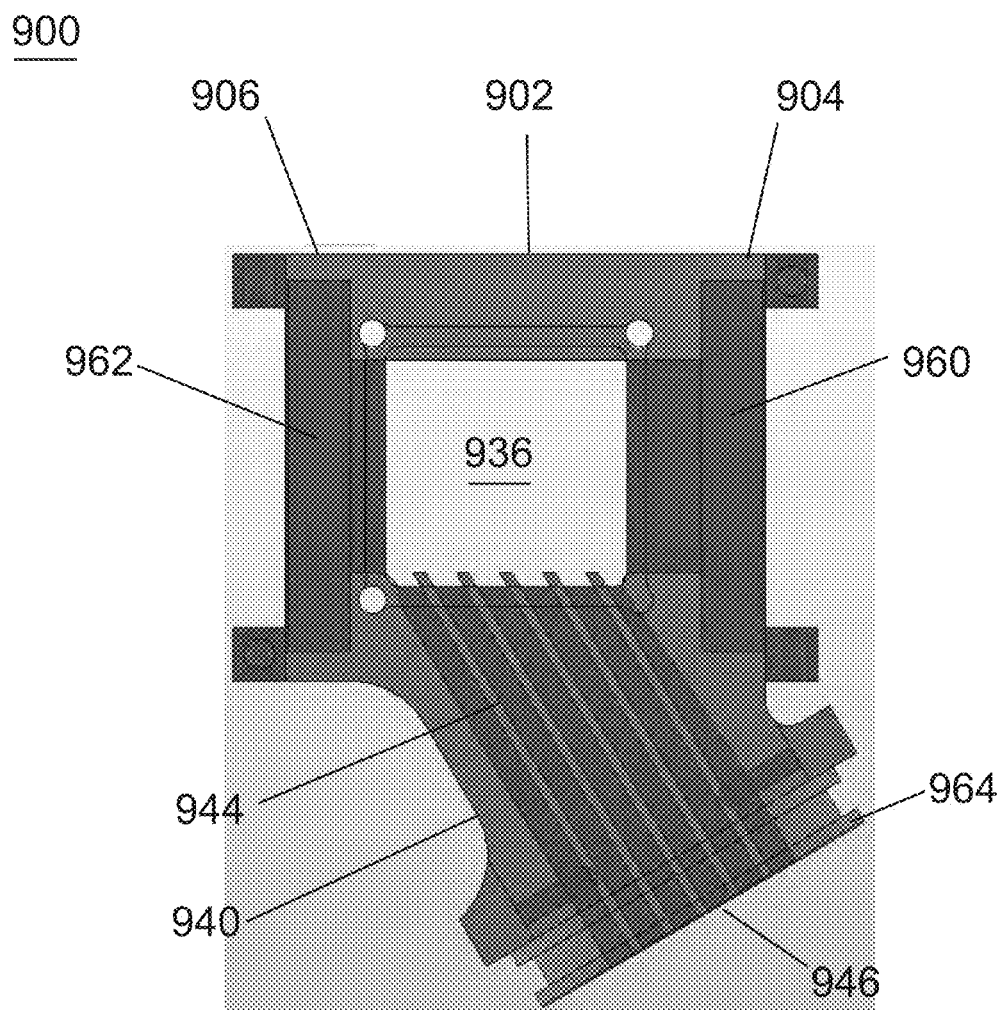
FIG. 15 is a side view of the ultrasonic transducer module of FIG. 14.

FIG. 14 is a perspective view of an ultrasonic transducer module 900 that incorporates a separation system formed from baffles. FIG. 15 is a side view (y-z plane) of the ultrasonic transducer module of FIG. 14.

This ultrasonic transducer module 900 has many of the same components as the ultrasonic transducer module of FIG. 2, including the housing 902 with the first end 904, second end 906, and four side walls 910, 912, 914, 916. A primary flow channel 930 is defined between the first end and the second end of the housing, as represented by circular openings 932, 934. The first end 904 and the second end 906 of the housing can be considered as defining a z-axis. The sides of the housing on which the ultrasonic transducer (not shown) and the reflector (not shown) would be located are represented by square openings 936, 938, and can be considered as defining a y-axis.

In the ultrasonic transducer of FIG. 14, an angled extension 940 extends from one of the sides 910 between the ultrasonic transducer 936 and the reflector 938. A secondary flow channel 942 is present within the angled extension 940, the secondary flow channel connecting to the primary flow channel 930 between the first end 904 and the second end 906 of the module. A set of baffles 944 is located within the secondary flow channel 942. The baffles are flat plates. The baffles 944 lead to a third opening 946 at the distal end 948 of the angled extension 940/secondary flow channel 942. A third attachment member 964 is disposed at the distal end 948 of the angled extension 940. As illustrated here, the first attachment member 960 and the second attachment member 962 are both female members (e.g. a hole), and the third attachment member 964 is a male member (e.g. a tongue).

Figure 16:
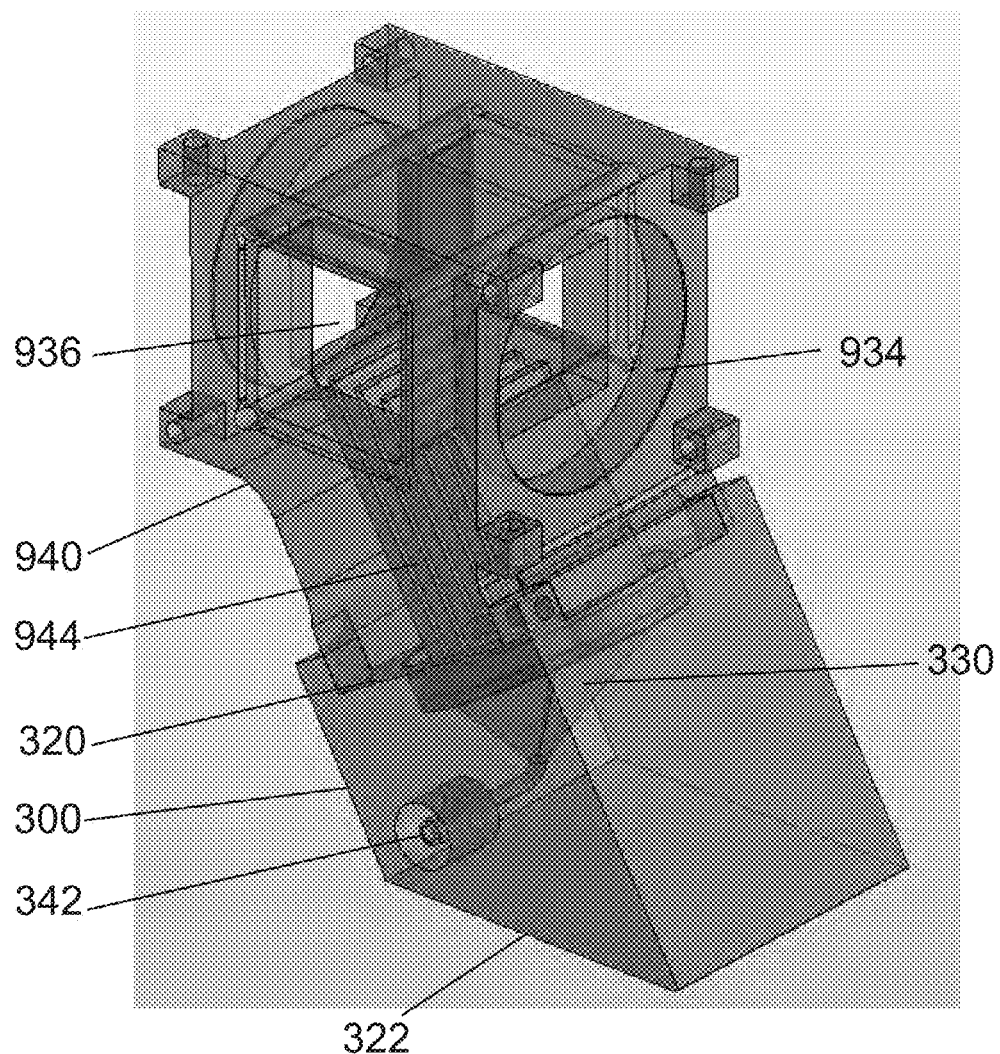
FIG. 16 is a perspective view of the ultrasonic transducer module of FIG. 14 joined to a collection well module having an angled lower end.

In one mode of operation illustrated in FIG. 16, it is contemplated that the ultrasonic transducer module of FIG. 14 will be oriented such that the angled extension 940 acts as a base. The acoustic standing wave field will trap particles and cause aggregation until the particle aggregate is heavy enough for gravity to cause the aggregate to fall downwards and out of the acoustic standing wave field. The aggregate then falls down onto the baffles 944, which acts as a collection surface to guide the aggregate to the collection well module.

In another mode of operation, it is contemplated that the ultrasonic transducer module of FIG. 14 will be oriented such that the angled extension 940 points upwards, i.e. against the flow of gravity (the upwards direction indicated by arrow 905 in FIG. 15). Fluid flows past the ultrasonic transducer 936, then upwards through the angled extension 940. As the fluid flows upwards over and through the baffles, particles that escape the ultrasonic transducer will contact the baffles 944. The baffles will retard the particles, and can cause them to fall downwards back towards the acoustic standing wave field generated by the ultrasonic transducer 936, or towards a collection well device (not depicted).

FIG. 16 is a perspective view of the ultrasonic transducer module 900 of FIG. 13 joined to a collection well module 300. This collection well module is another variation of the collection well module 300 previously described in FIG. 4. This module also has four side walls, an upper wall 320, a lower wall 322, a well 330, and a port 342. Notably, the lower wall 322 is angled, rather than parallel to the upper wall as in FIG. 4. The angle of the lower wall is the same as the angle of the angled extension. This provides a flat base for supporting the ultrasonic transducer module.

The various modules discussed above can be made from any suitable material. Such suitable materials include medical grade plastics, such as polycarbonates or polymethyl methacrylates, or other acrylates. It is generally desirable for the material to be somewhat transparent, so that a clear window can be produced and the internal flow channels and flow paths can be seen during operation of the acoustophoresis device/system.

Various coatings may be used on the internal flow channels of the modules. Such coatings include epoxies, for example epichlorohydrin bisphenol crosslinked with an amine or a polyamide; or polyurethane coatings, for example a polyester polyol crosslinked with aliphatic isocyanates. Such coatings are useful for producing a smooth surface and/or reducing surface tension, permitting cells to slide better under the influence of gravity along the flow channel surface and into desired locations (such as collection well modules).

The flow rate of the acoustophoretic device must be controlled so that gravity can act on particle aggregates. In this regard, it is contemplated that the particle/fluid mixture passing in/out of the flow path in the acoustophoretic device through the inlet/outlet modules or the port module can flow at rates of up to about 100 milliliters per minute (ml/min). By way of comparison, the flow rate out of the collection well modules through the ports is much less, from about 3 ml/min up to about 10 ml/min.

The present disclosure contemplates kits formed from any combination of the modules described above. In particular embodiments, the kits include at least an ultrasonic transducer module 200, a collection well module 300/500, and an inlet/outlet module 400/600. In other embodiments, the kits include at least an ultrasonic transducer module 200, a collection well module 300/500, two port modules 700, and a three-way connector module 892. In yet additional embodiments, the kits include at least two ultrasonic transducer modules 200, at least two collection well modules 300/500, a three-way connector module 892, and either (i) an inlet/outlet module 400/600 or two port modules 700.

Various acoustophoretic systems can be made using the different modular components described above. FIGS. 17-29 illustrate different systems. It is noted that the three-way connector modules used herein have two male attachment members and one female attachment member, with the side attachment member being a male member.

Figure 17:
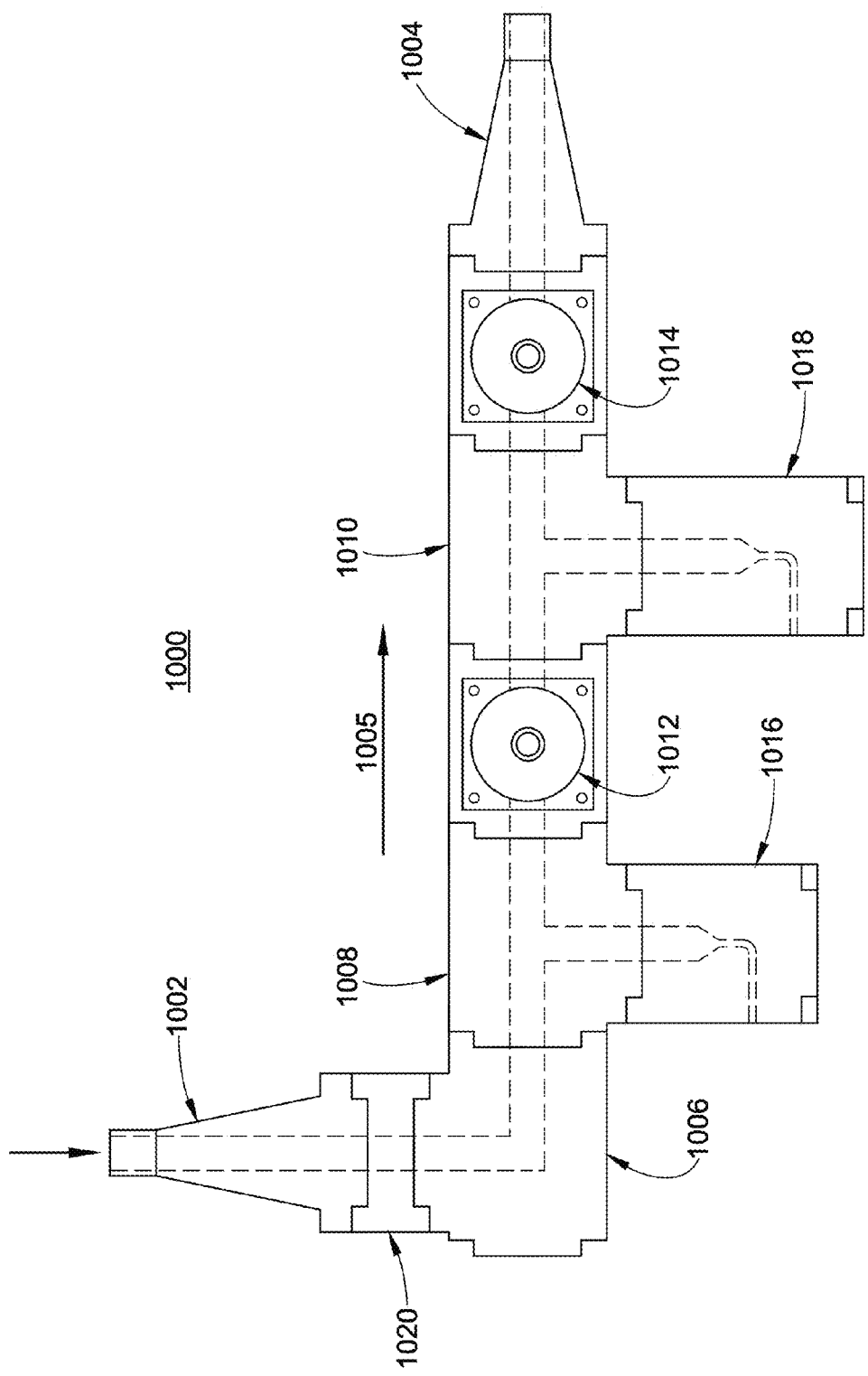
FIG. 17 is a side view of a first modular acoustophoretic system.

The system 1000 of FIG. 17 is built from two port modules 1002, 1004, a two-way curved connector module 1006, two three-way connector modules 1008, 1010, two ultrasonic transducer modules 1012, 1014, two collection well modules 1016, 1018, and a female/female two-way connector module 1020. Starting at the left, a port module 1002 acts as the inlet, and is connected to the female/female two-way connector module 1020, which is in turn connected to the two-way curved connector module 1006, which joins a three-way connector module 1008. The first collection well module 1016 connects to the three-way connector module 1008, and acts as a base for the system. An ultrasonic transducer module 1012 is then connected, then the other three-way connector module 1010. The second collection well module 1018 connects to this three-way connector module 1010, and also acts as a base. Note the second collection well module 1018 is taller than the first collection well module 1016, so that the overall system is tilted at an acute angle. The second ultrasonic transducer module 1014 is connected, and then the second port module 1004 acts as an outlet. Fluid flow is in the direction of the arrow 1005. In operation, as particle aggregates grow in each ultrasonic transducer module 1012, 1014 and fall out of the acoustic standing wave field, they follow gravity downwards and countercurrent to the fluid flow into their respective collection well module 1016, 1018. Any particles that escape the first ultrasonic transducer module 1012 should be trapped by the second ultrasonic transducer module 1014. It is contemplated that as a result, the size of the particle aggregates in the first ultrasonic transducer module should generally be different from the aggregates in the second ultrasonic transducer module, as the aggregates in the second ultrasonic transducer module should grow at a slower rate due to the lower number of particles in the fluid passing through.

Figure 18:
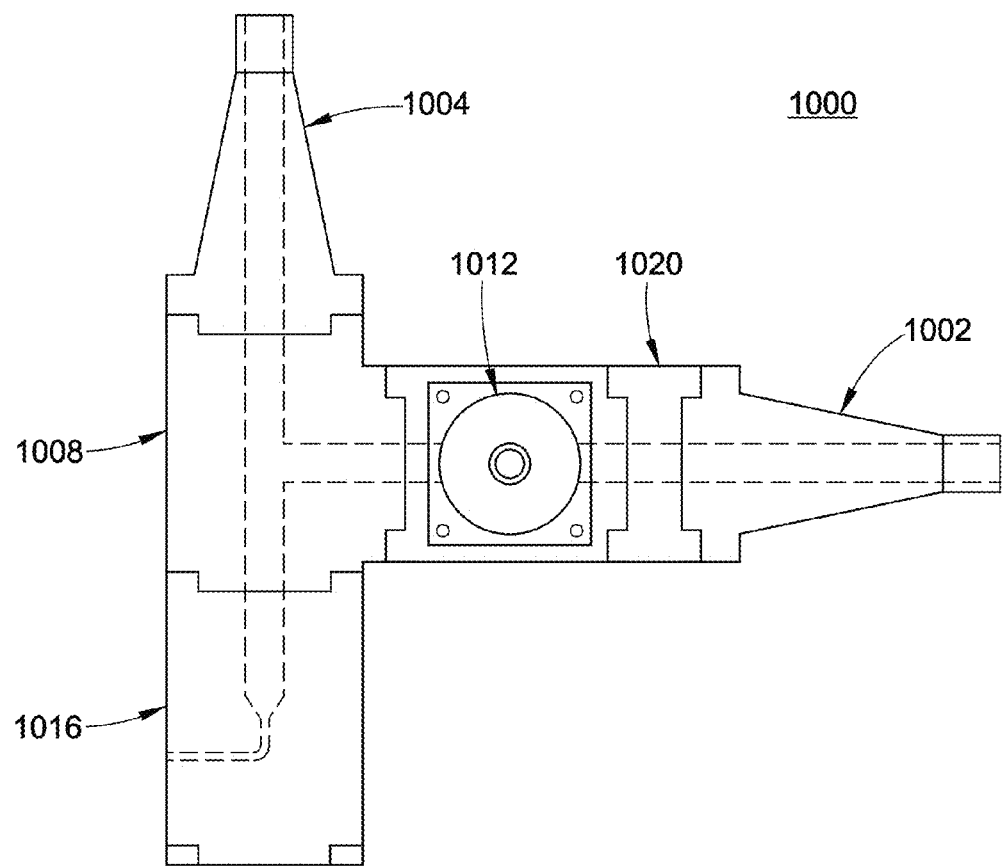
FIG. 18 is a side view of a second modular acoustophoretic system.

FIG. 18 is a relatively simple system 1000 built from two port modules 1002, 1004, a three-way connector module 1008, an ultrasonic transducer module 1012, a collection well module 1016, and a female/female two-way connector module 1020. The particle/fluid mixture flows into the system through port module 1002, which acts as an inlet, and the female/female two-way connector module 1020. Particle aggregates can be swept by the current into the three-way connector module 1008, where they then fall into the collection well module 1016. Fluid flows up and out of the system through port module 1004, which acts as an outlet.

Figure 19:
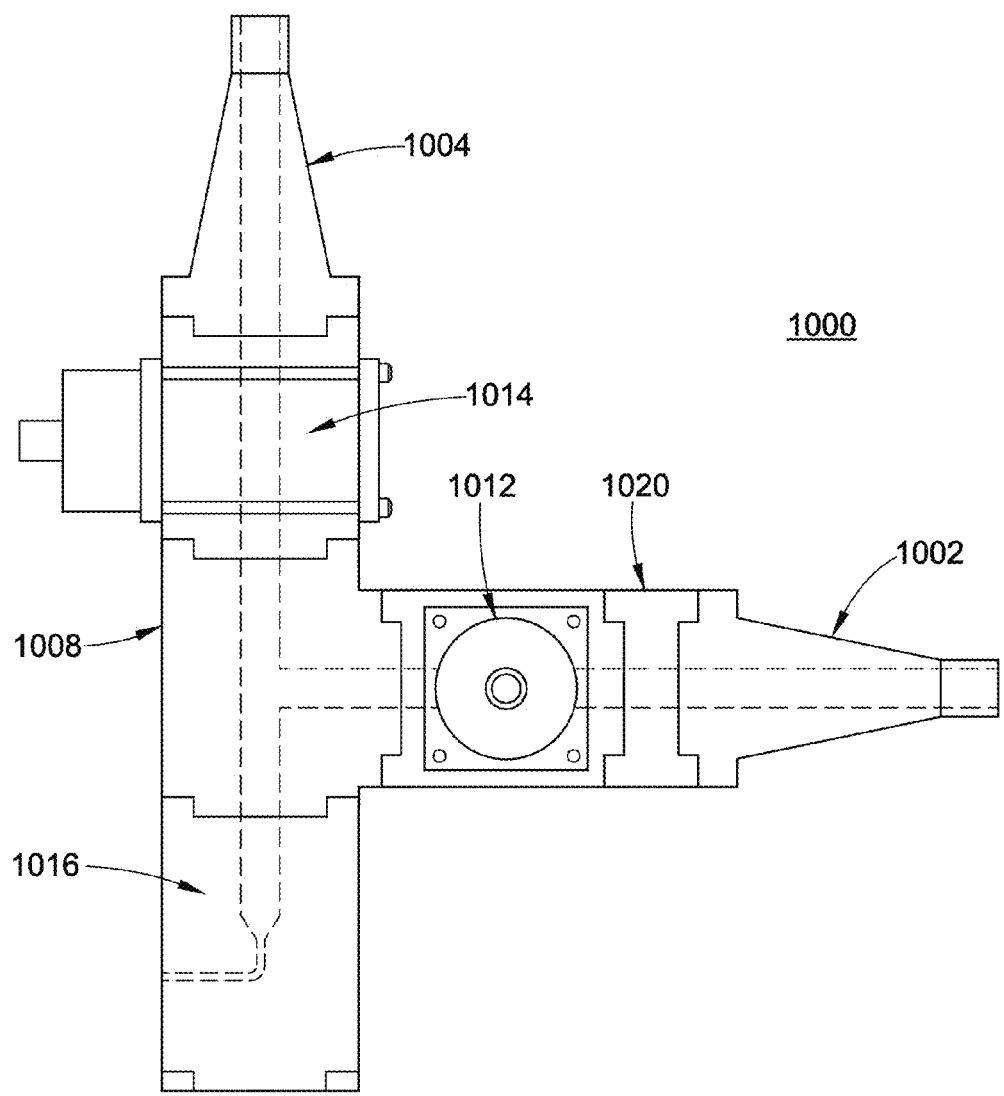
FIG. 19 is a side view of a third modular acoustophoretic system.

FIG. 19 is a variation on the system of FIG. 18. Here, a second ultrasonic transducer module 1014 is added before the port module 1004. Aggregates formed in the second ultrasonic transducer module 1014 can fall directly into the collection well device 1016.

Figure 20:
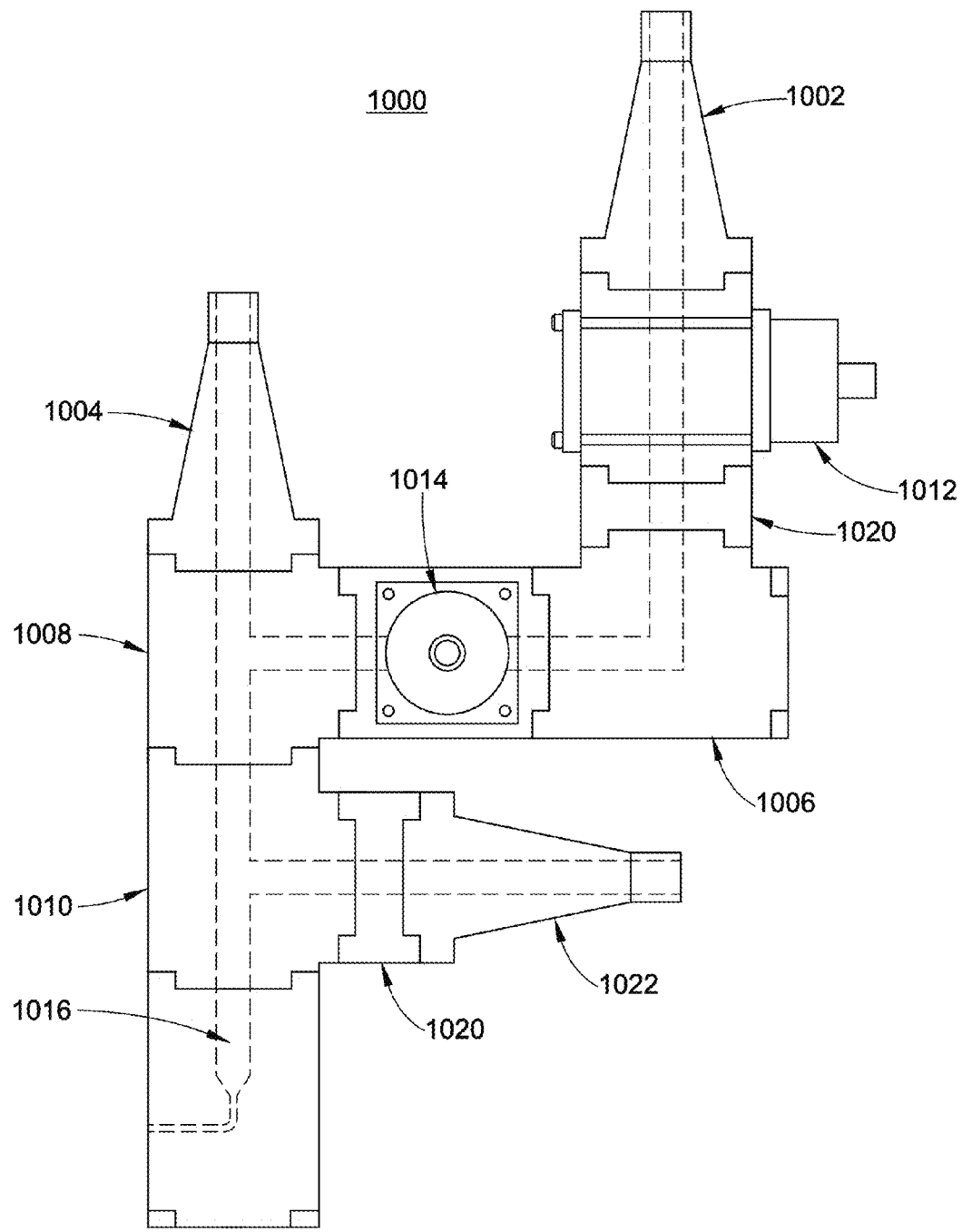
FIG. 20 is a side view of a fourth modular acoustophoretic system.

The system of FIG. 20 uses 11 different modules. Here, the particle/fluid mixture enters the system through port module 1002. Particles are trapped by the first ultrasonic transducer module 1012. Any particles that escape the first ultrasonic transducer module should be trapped by the second ultrasonic transducer module 1014. In contrast to the system of FIG. 17, though, the aggregates from the first ultrasonic transducer module will also pass through the second ultrasonic transducer module. This should sweep all aggregates out and into the collection well module. Fluid can exit the system at the top through port module 1004. A third port module 1022 is provided between the ultrasonic transducers 1012, 1014 and the collection well module 1016. This third port module 1022 also acts as an outlet, and can be used for draining fluid if desired, or for handling overflow from the collection well module (e.g. if particles build up too quickly to be completely drained through the port).

Figure 21:
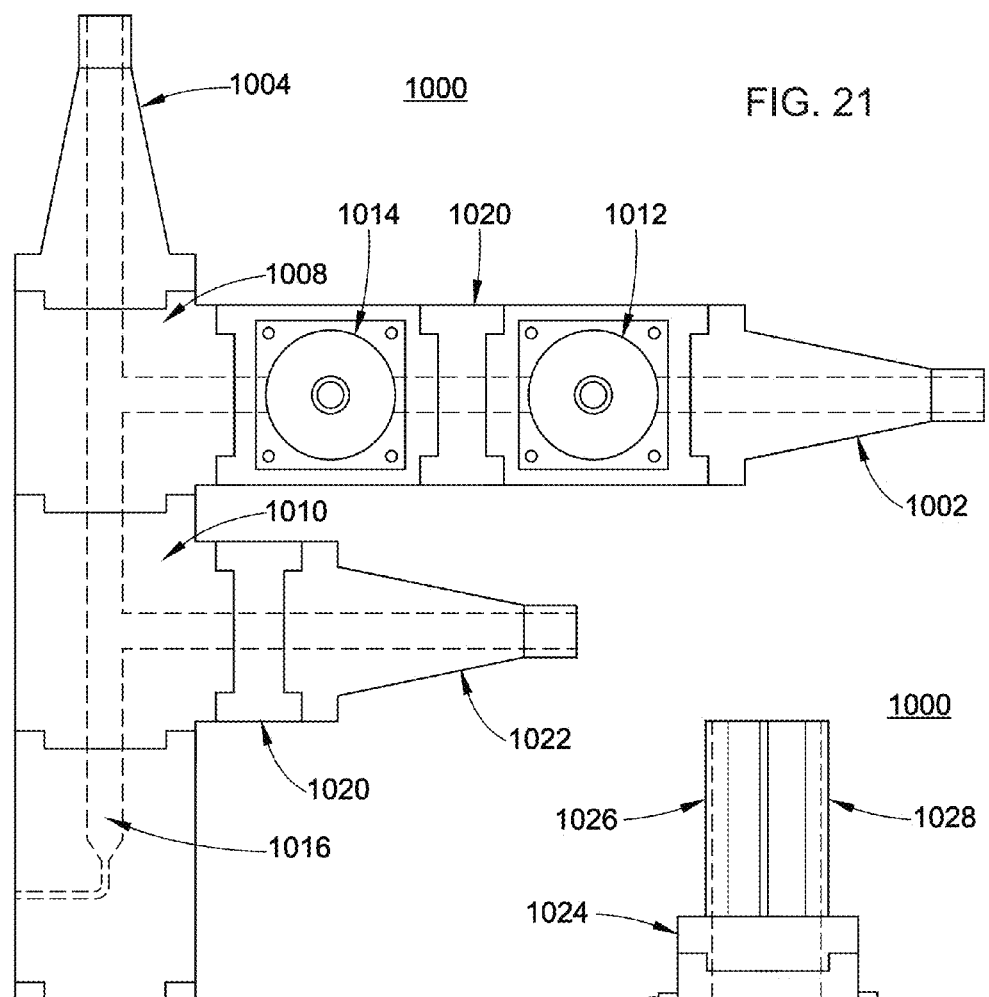
FIG. 21 is a side view of a fifth modular acoustophoretic system.

FIG. 21 is similar to FIG. 20, except that there is no curved two-way connector module 1006 between the two ultrasonic transducer modules 1012, 1014. Only 10 modules are used.

Figure 22:
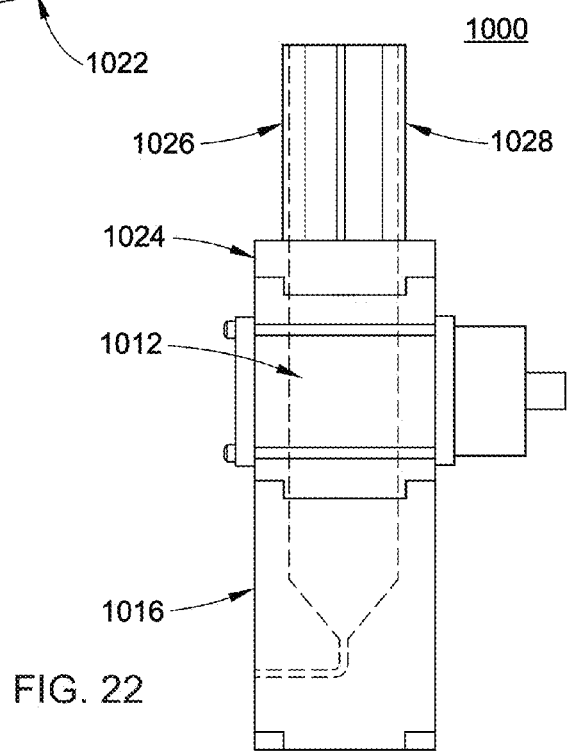
FIG. 22 is a side view of a sixth modular acoustophoretic system.

FIG. 22 is a simple system that uses an ultrasonic transducer module 1012, a collection well module 1016, and an inlet/outlet module 1024. The particle/fluid mixture flows through one sub-channel 1026 into the ultrasonic transducer module 1012, and pressure pushes fluid out the other sub-channel 1028. Particle aggregates fall directly into the collection well module 1016.

Figure 23:
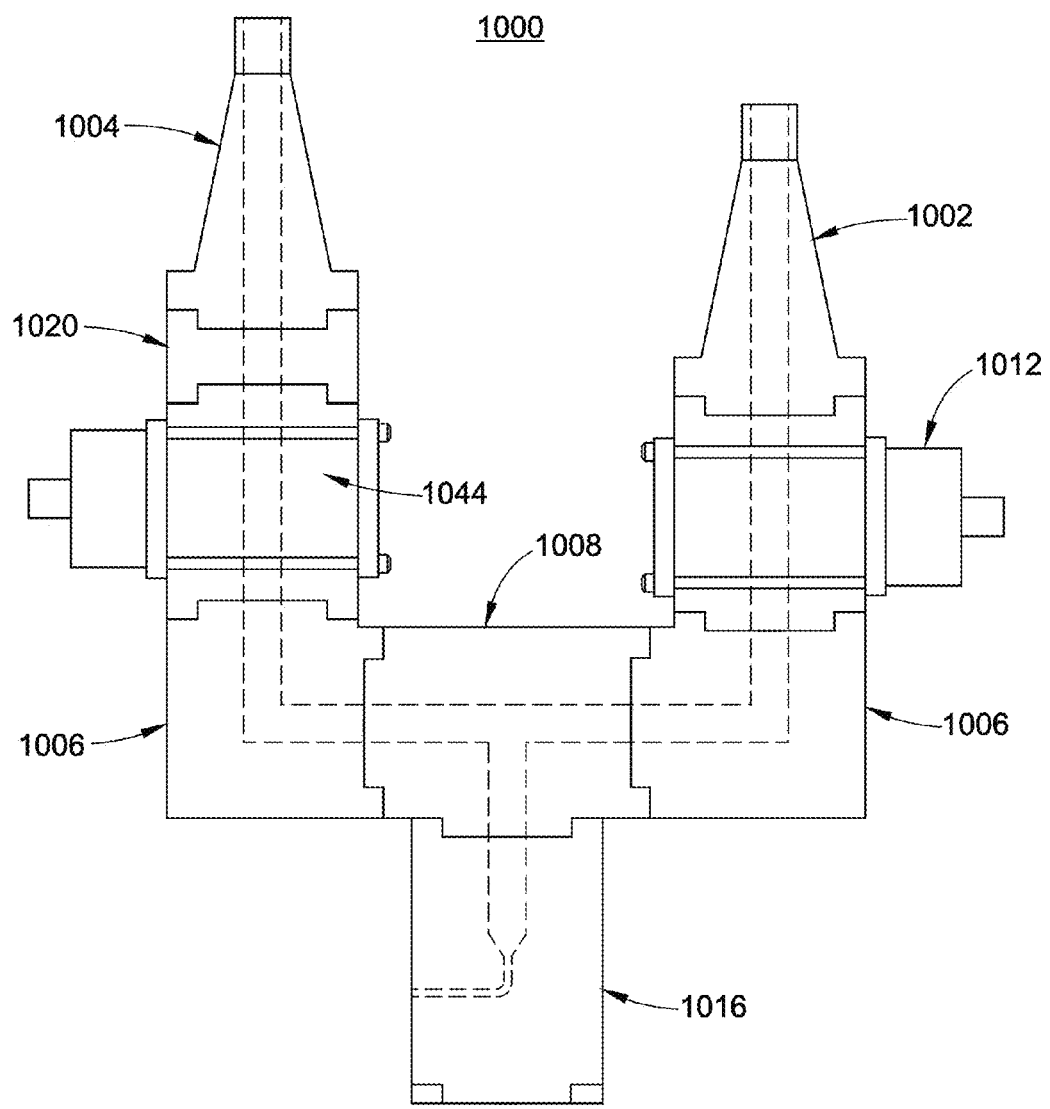
FIG. 23 is a side view of a seventh modular acoustophoretic system.

In FIG. 23, the particle/fluid mixture enters through port module 1002 and fluid exits the system through port module 1004. Here, the particle aggregates from both ultrasonic transducers 1012, 1014 is collected in the same (and only) collection well module 1016.

Figure 24:
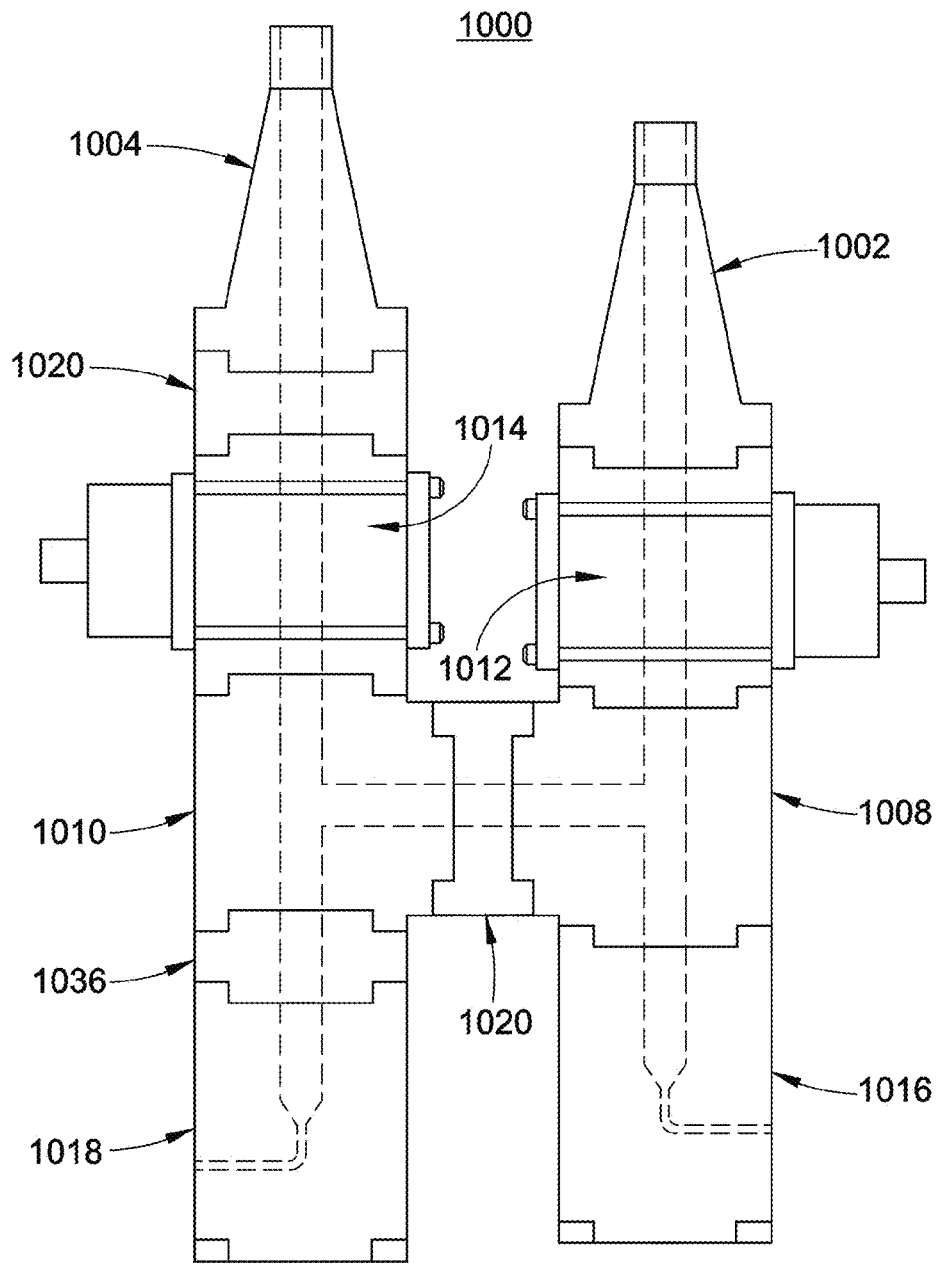
FIG. 24 is a side view of an eighth modular acoustophoretic system.

In FIG. 24, the particle/fluid mixture enters through port module 1002 and fluid exits the system through port module 1004. Fluid flow is in a U-shape. The particle aggregates from each ultrasonic transducer 1012, 1014 fall directly downwards into a collection well module 1016, 1018. Also, a male/male two-way connector module 1036 is used between modules 1010, 1018.

Figure 25:
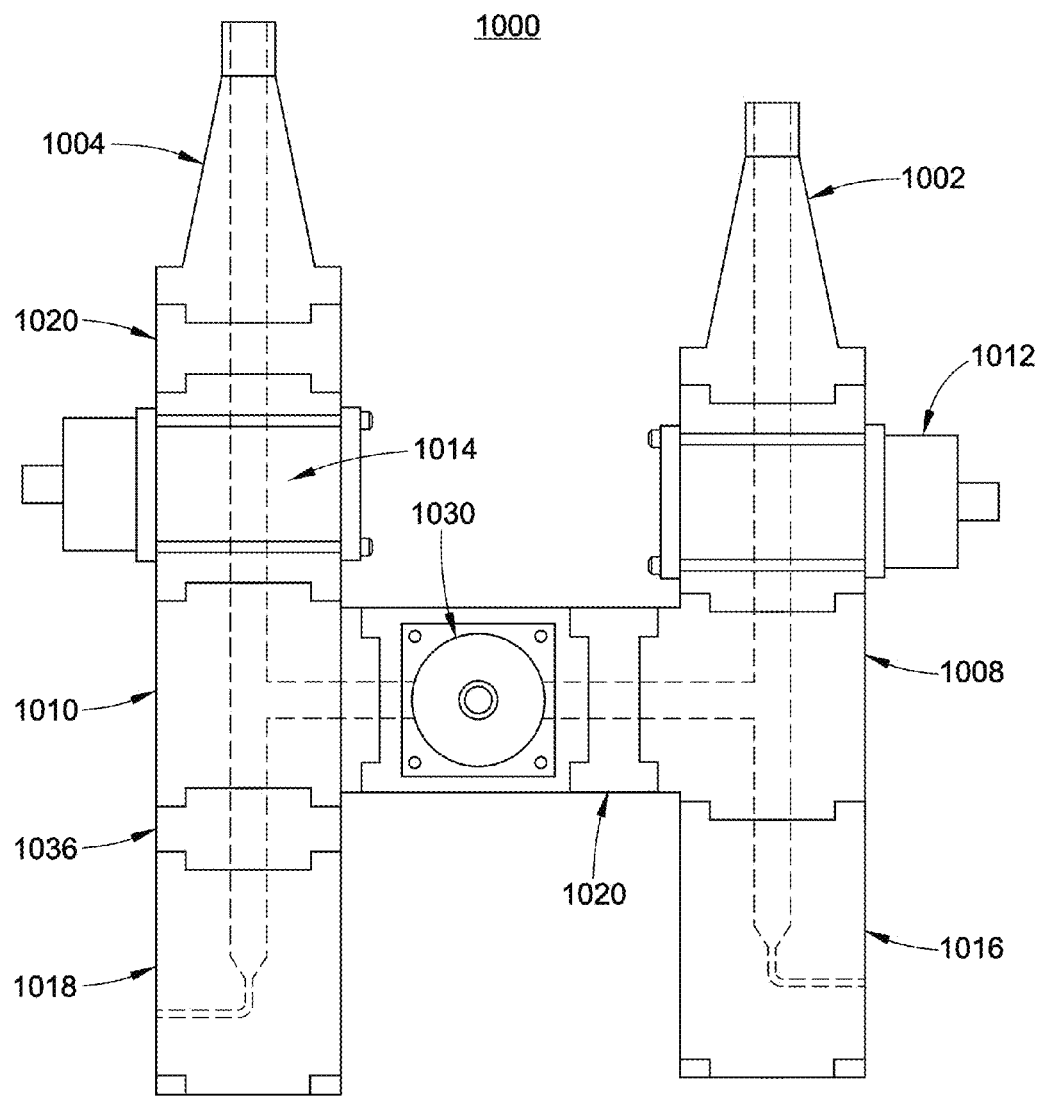
FIG. 25 is a side view of a ninth modular acoustophoretic system.

The system of FIG. 25 is similar to the system of FIG. 24, but adds a third ultrasonic transducer 1030. A male/male two-way connector module 1036 is used between the modules 1010, 1018.

Figure 26:
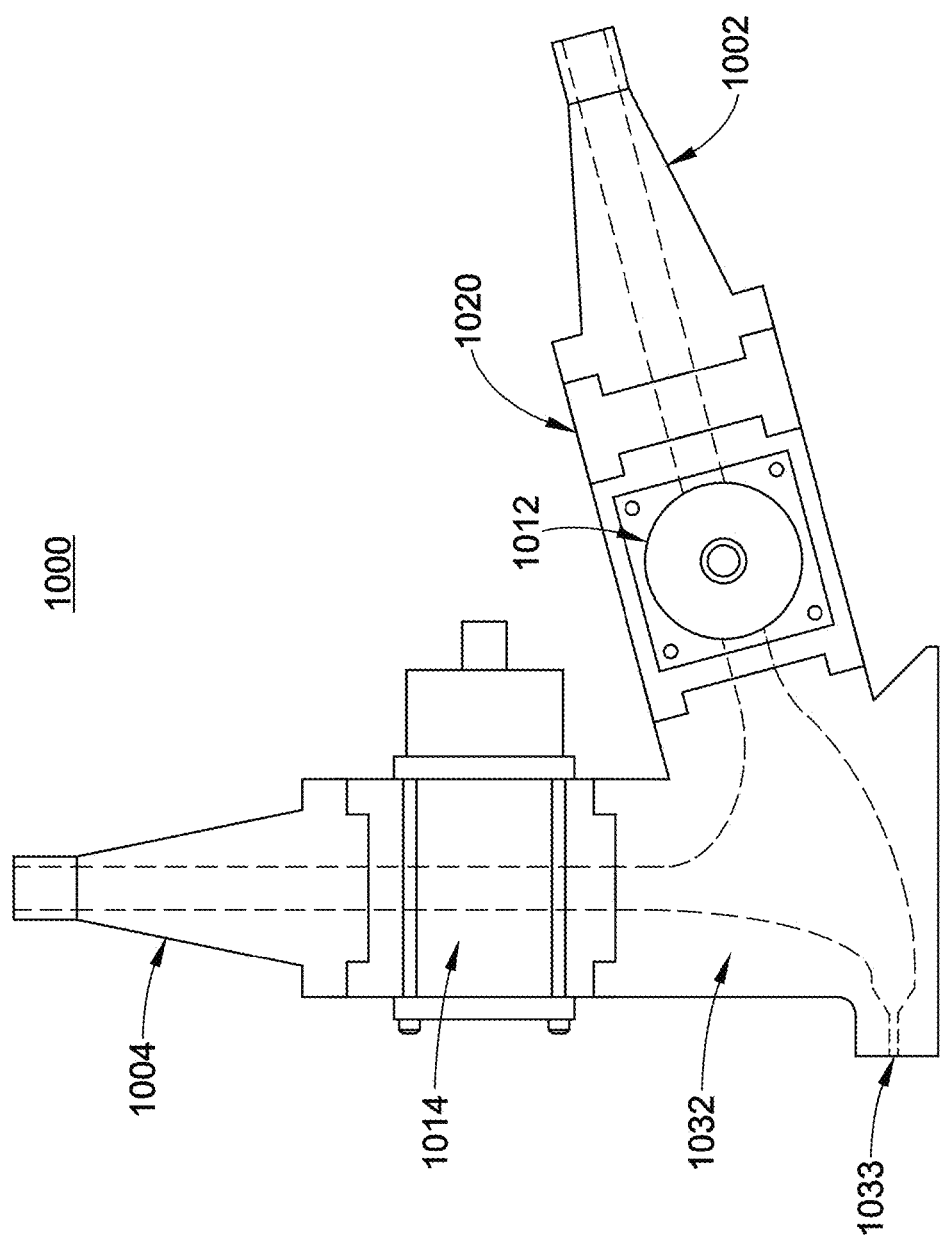
FIG. 26 is a side view of a tenth modular acoustophoretic system.

The system of FIG. 26 illustrates the use of the angled collection well module 1032. The particle/fluid mixture enters through port module 1002 and fluid exits the system through port module 1004. The particle aggregates from both ultrasonic transducer modules 1012, 1014 settle by gravity into the angled collection well module 1032 and move down to the port 1033.

Figure 27:
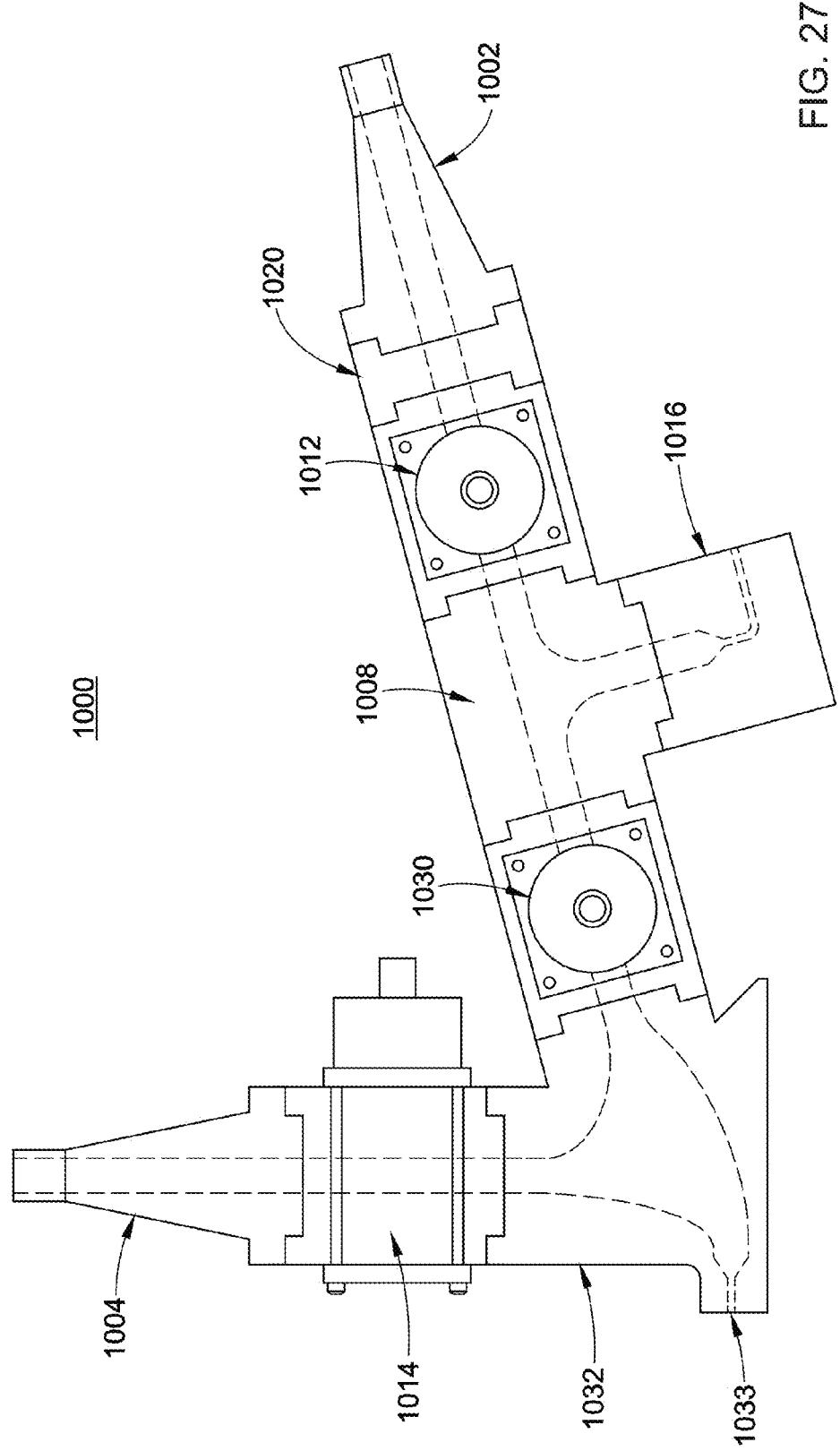
FIG. 27 is a side view of an eleventh modular acoustophoretic system.

FIG. 27 illustrates a system with another collection well module 1016 and a third ultrasonic transducer module 1030 added to the system of FIG. 26, but otherwise operates in the same manner. The particle aggregates from the ultrasonic transducer modules 1012, 1014 still settle by gravity into the angled collection well module 1032.

Figure 28:
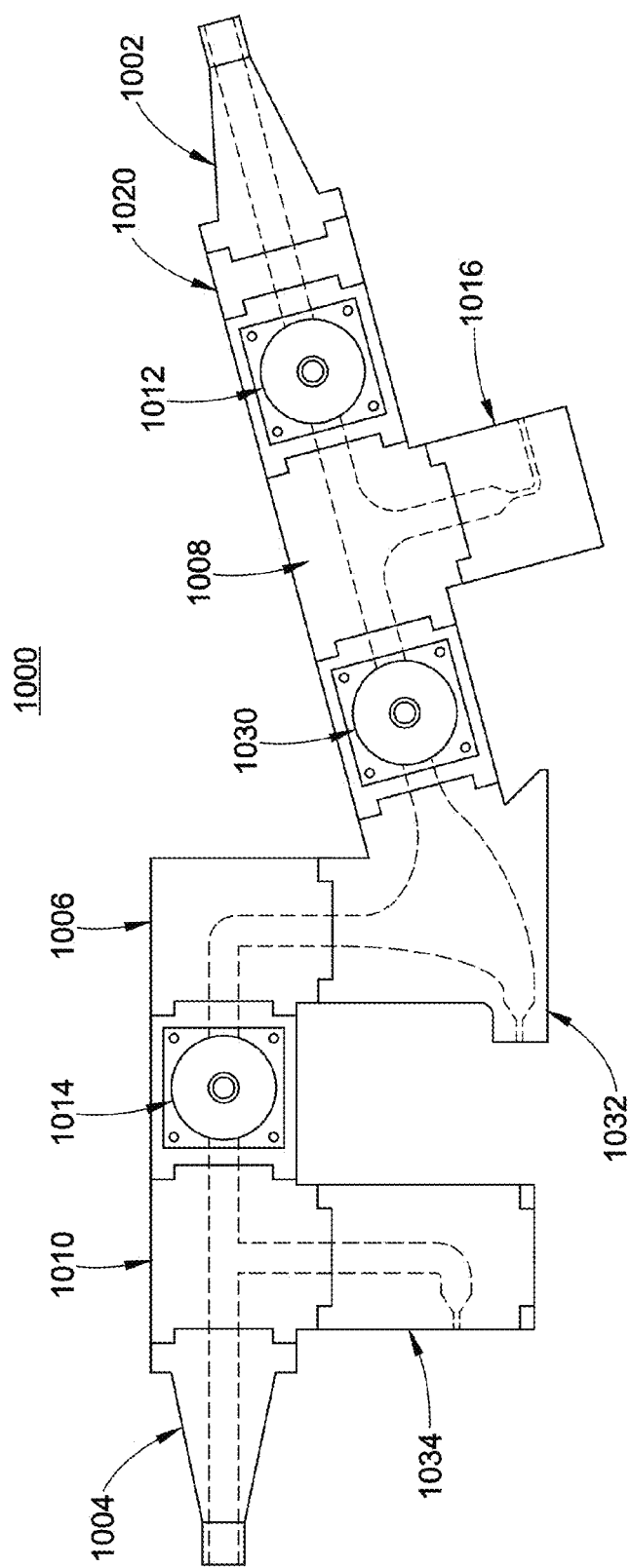
FIG. 28 is a side view of a twelfth modular acoustophoretic system.

In FIG. 28, a curved two-way connector module 1006 turns the fluid flow path of FIG. 27 into a horizontal orientation. Here, the particle aggregates from ultrasonic transducer module 1012 still settle by gravity into the angled collection well module. The particle aggregates from ultrasonic transducer module 1018 are now captured in a third collection well module 1034.

Figure 29:
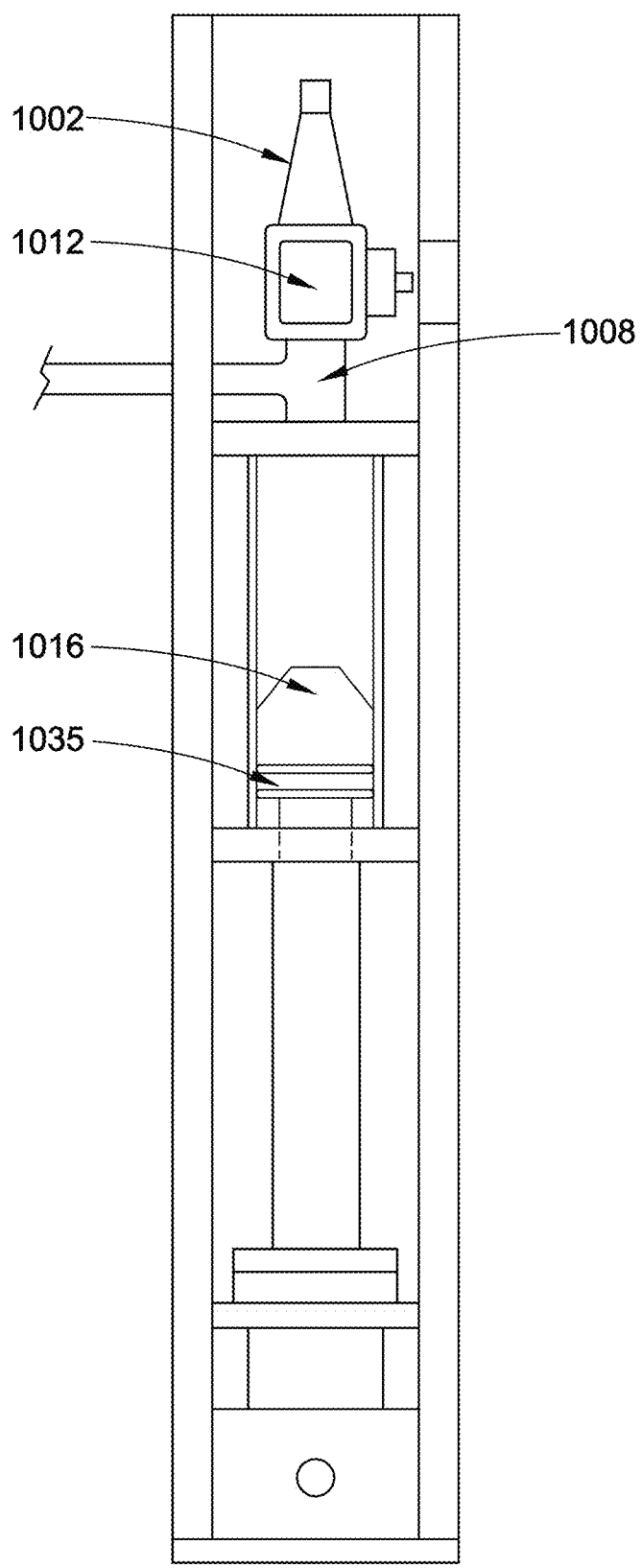
FIG. 29 is a side view of a thirteenth modular acoustophoretic system.

In FIG. 29, the particle/fluid mixture flows into a three-way connector 1008 and then travels upwards into ultrasonic transducer module 1012 and out through port module 1002. Particle aggregates fall downwards into a variable-volume collection module 1016.

This collection module is formed from a housing having an upper end and an opposing lower end. An inlet is located at the upper end of the housing, and leads to a well. The well has a constant cross-section. A plunger provides a floor to the well, with the plunger adapted to move through the well from the bottom end towards the upper end. Here, the collection module is in the form of a large cylinder. A plunger 1035 is present at the bottom of the collection module. This can be used to compact the particle aggregates by moving the plunger upwards, reducing the volume of the well. The particle aggregates remain against the plunger. Any particles still suspended in the fluid will either join the aggregates against the plunger, or be pushed into the acoustic standing wave field in the ultrasonic transducer module, and so are not lost through the outlet 1002. The particles can then be collected. It is contemplated that this module can be used for batch processing. Alternatively, a port (not illustrated) can located on a side of the housing proximate the upper end, which is fluidly connected to the well. The particles can be collected through the port.

Some explanation of the ultrasonic transducers used in the devices of the present disclosure may be useful as well. In this regard, the transducers use a piezoelectric crystal, usually made of PZT-8 (lead zirconate titanate). Such crystals may have a 1 inch diameter and a nominal 2 MHz resonance frequency. Each ultrasonic transducer module can have only one crystal, or can have multiple crystals that each act as a separate ultrasonic transducer and are either controlled by one or multiple amplifiers.

Figure 30:
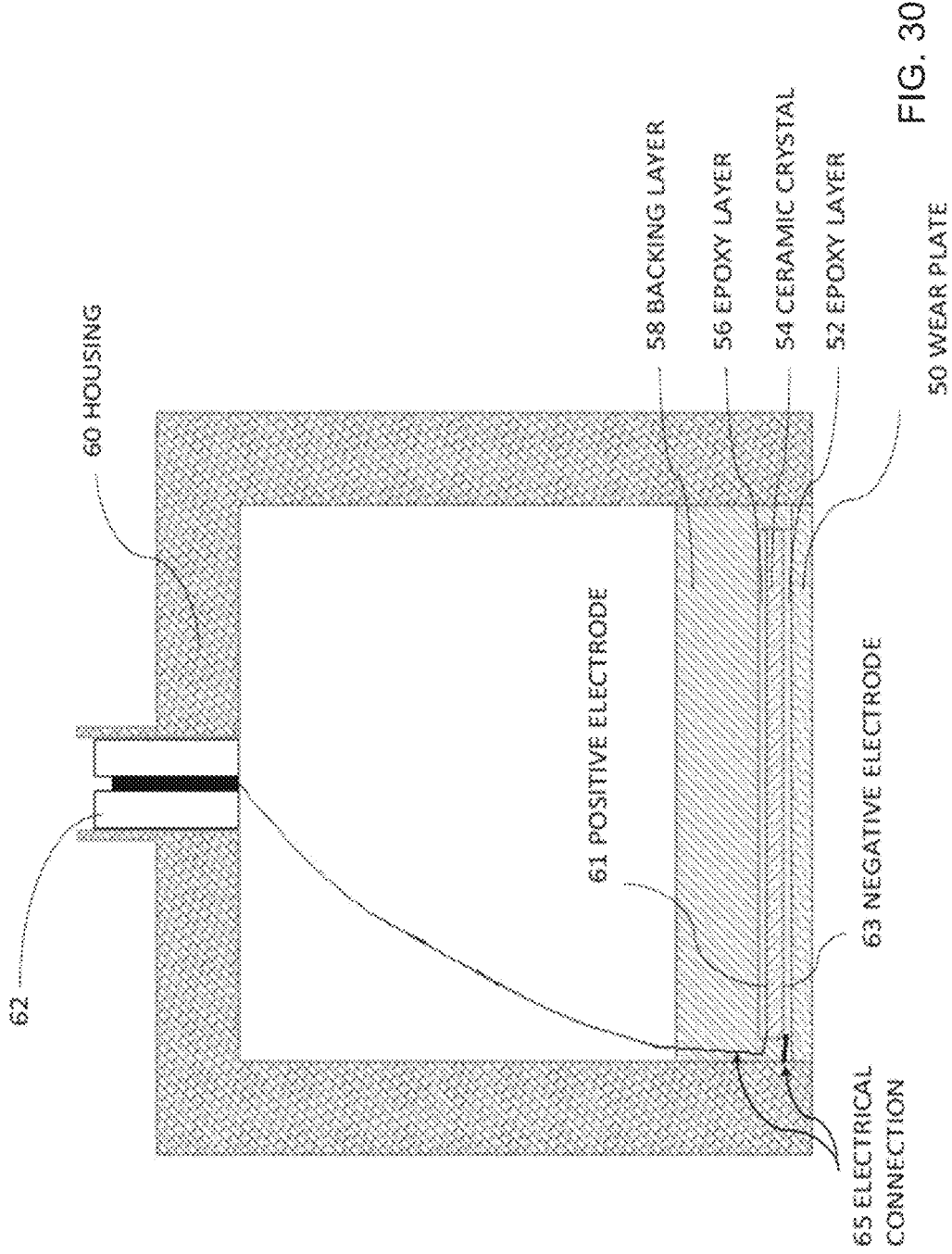
FIG. 30 is a cross-sectional diagram of a conventional ultrasonic transducer.

FIG. 30 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 31:
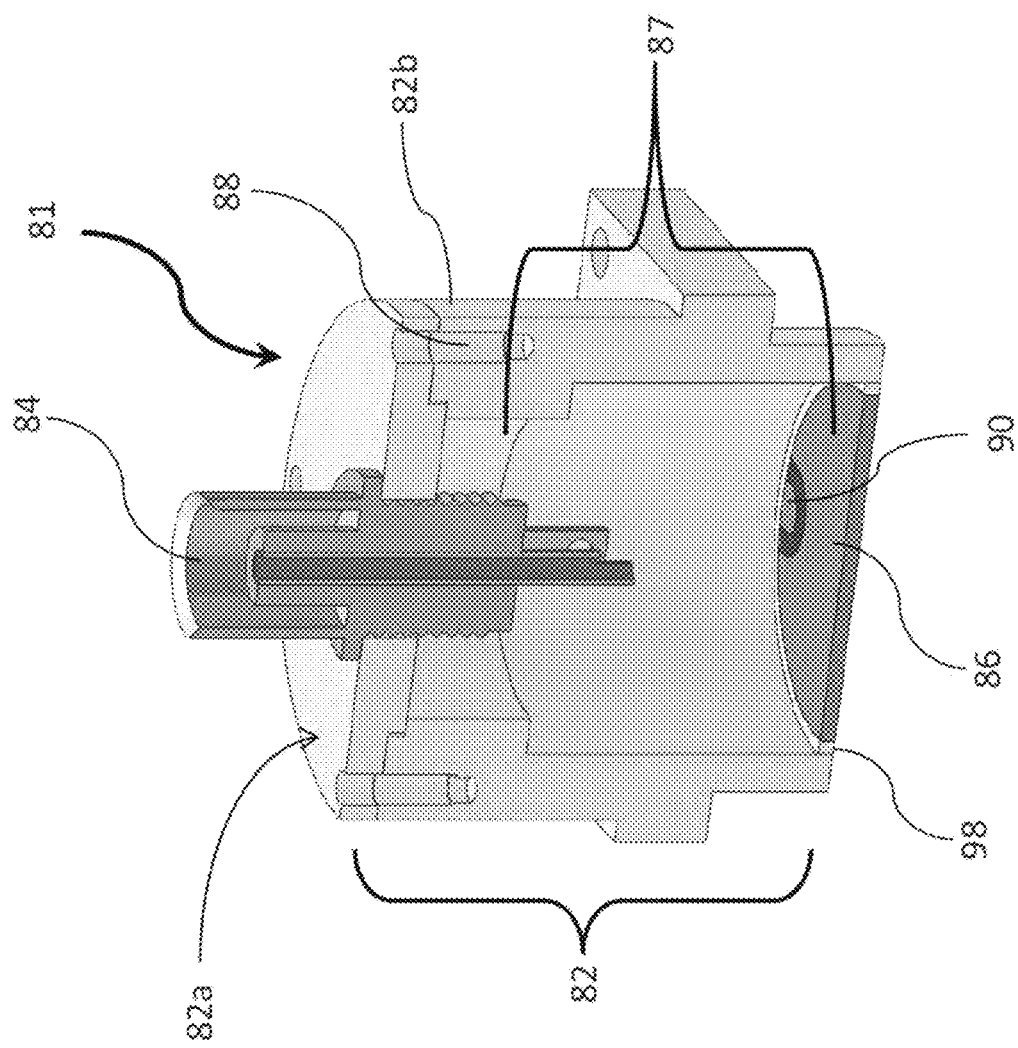
FIG. 31 is a cross-sectional diagram of an ultrasonic transducer of the present disclosure. An air gap is present within the transducer, and no backing layer or wear plate is present.

FIG. 31 is a cross-sectional view of an ultrasonic transducer 81 of the present disclosure. Transducer 81 has an aluminum housing 82. A PZT crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Figure 32:
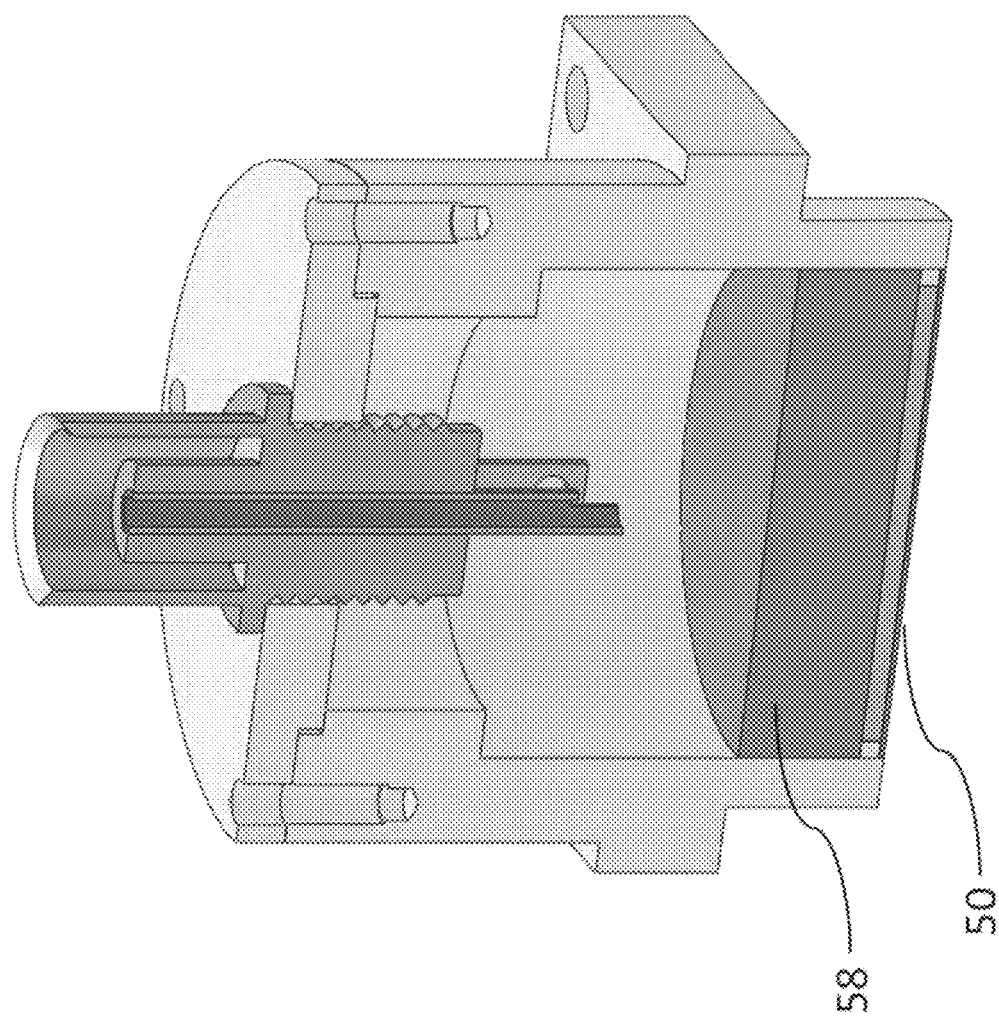
FIG. 32 is a cross-sectional diagram of an ultrasonic transducer of the present disclosure. An air gap is present within the transducer, and a backing layer and wear plate are present.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 are each connected to an electrode (positive and negative), such as silver or nickel. A wrap-around electrode tab 90 connects to the bottom electrode and is isolated from the top electrode. Electrical power is provided to the PZT crystal 86 through the electrodes on the crystal, with the wrap-around tab 90 being the ground connection point. Note that the crystal 86 has no backing layer or epoxy layer as is present in FIG. 30. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 32.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

In the present systems, the system is operated at a voltage such that the particles are trapped in the ultrasonic standing wave, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. The radial or lateral component of the acoustic radiation force is on the same order of magnitude as the axial component of the acoustic radiation force. As discussed above, the lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more places for particles to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 33:
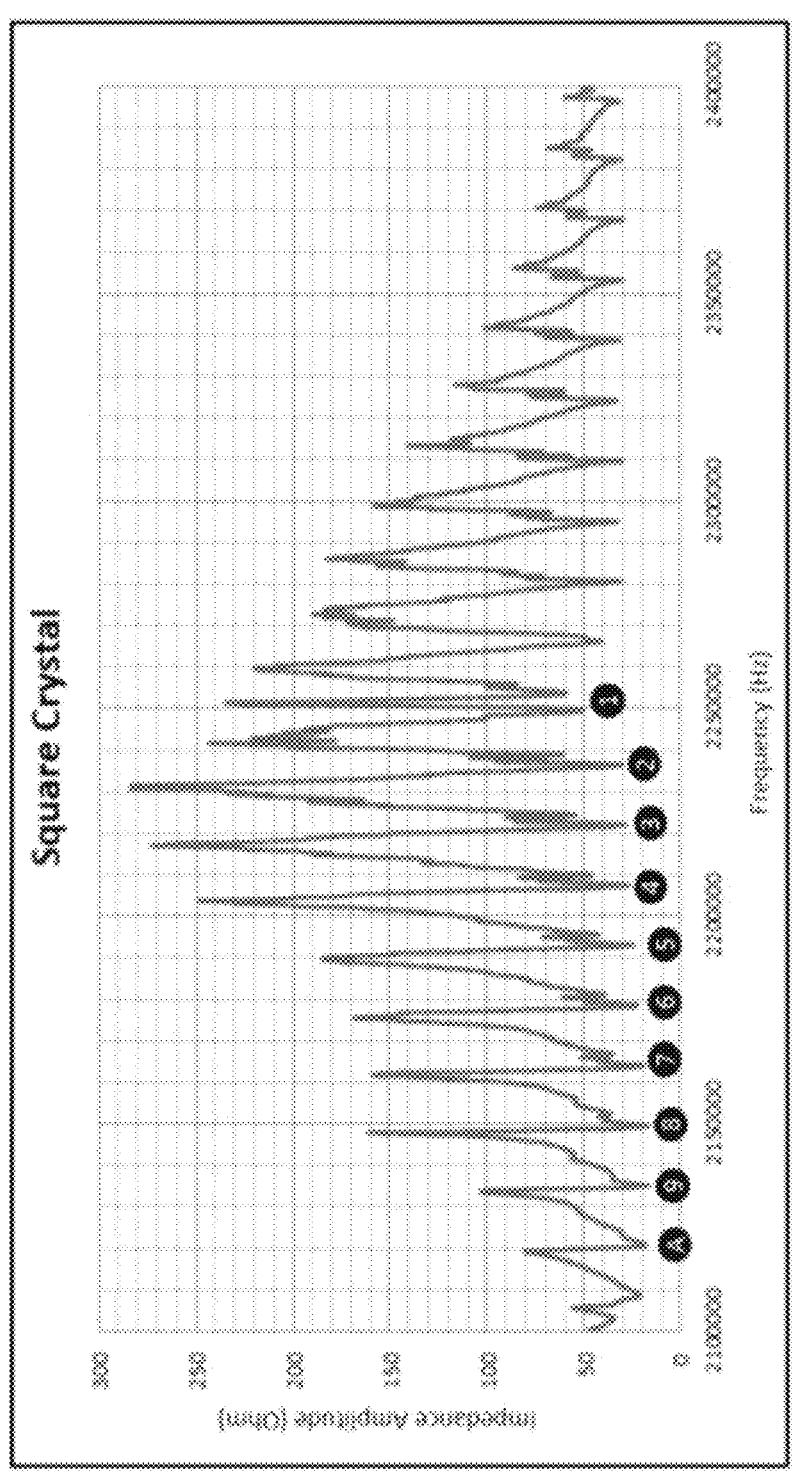
FIG. 33 is a graph of electrical impedance amplitude versus frequency for a square transducer driven at different frequencies.

FIG. 33 shows the measured electrical impedance amplitude of the transducer as a function of frequency in the vicinity of the 2.2 MHz transducer resonance when operated in a water column containing oil droplets. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 33, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 34A, for seven of the ten resonance frequencies identified in FIG. 33.

FIG. 34B shows an isometric view of the ultrasonic transducer volume in which the trapping line locations are being determined. FIG. 34C is a view of the ultrasonic transducer volume as it appears when looking down the inlet, along arrow 114. FIG. 34D is a view of the ultrasonic transducer volume as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines.

Figure 35:
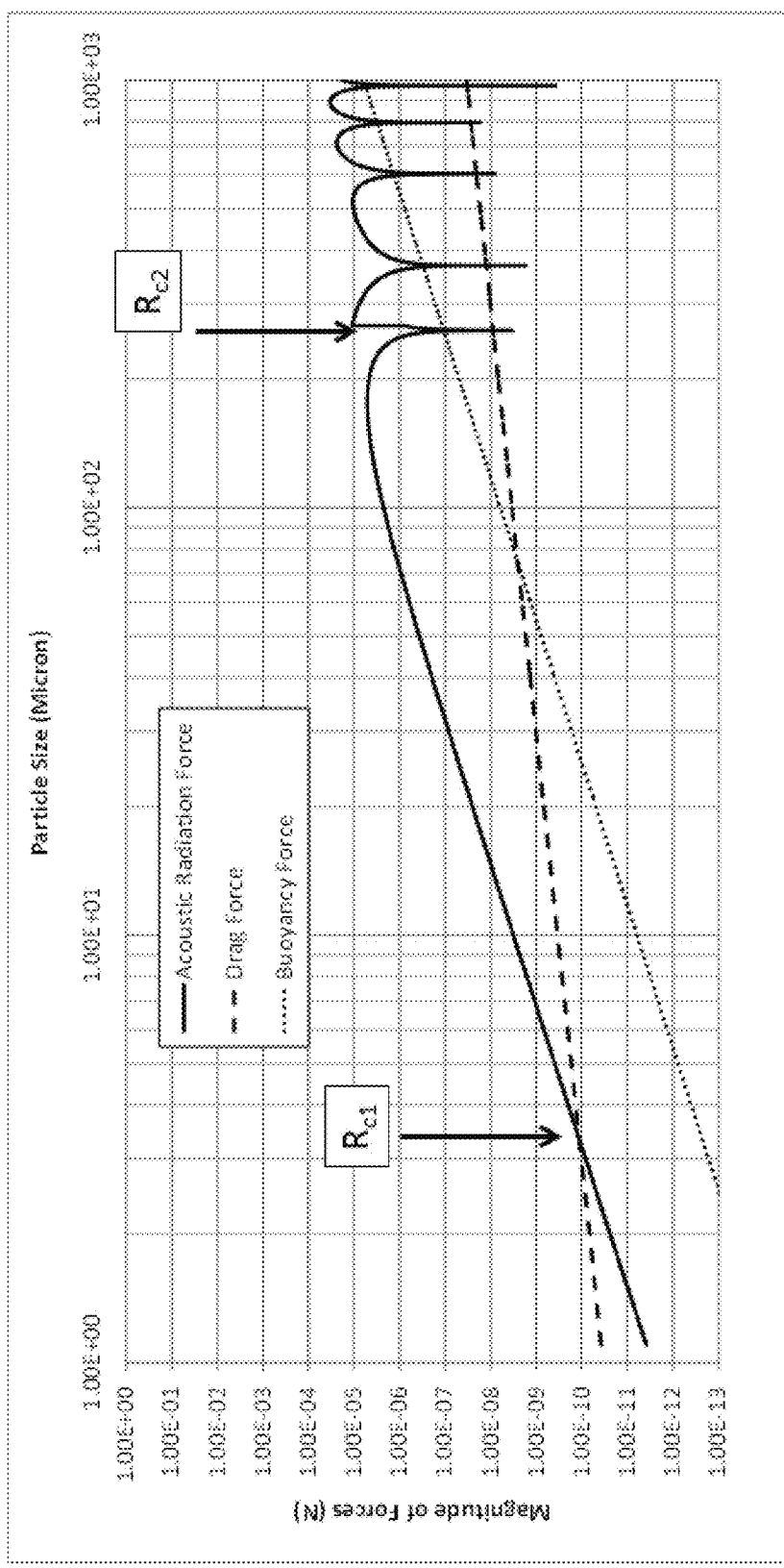
FIG. 35 is a graph showing the relationship of the acoustic radiation force, buoyancy force, and Stokes' drag force to particle size. The horizontal axis is in microns ($\mu m$) and the vertical axis is in Newtons (N).

Finally, FIG. 35 is a lin-log graph (linear y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling acts differently. When the particle size is small, the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 35 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size $R_{c2}$. Thus, FIG. 35 explains how small particles can be trapped continuously in a standing wave, grow into larger particles or clumps, and then eventually will rise or settle out because of increased buoyancy force.

The acoustophoretic devices of the present disclosure can be incorporated into acoustophoretic systems in which the devices are arranged in series to create a filter "train." The systems can therefore be considered multi-stage systems. The use of multiple stages of acoustic filtration reduces the burden on subsequent filtration stages and provides for (i) better clarification of the fluid and (ii) better separation of cells from the fluid. This permits recovery of the cells and/or the clarified fluid, as desired.

Figure 36:
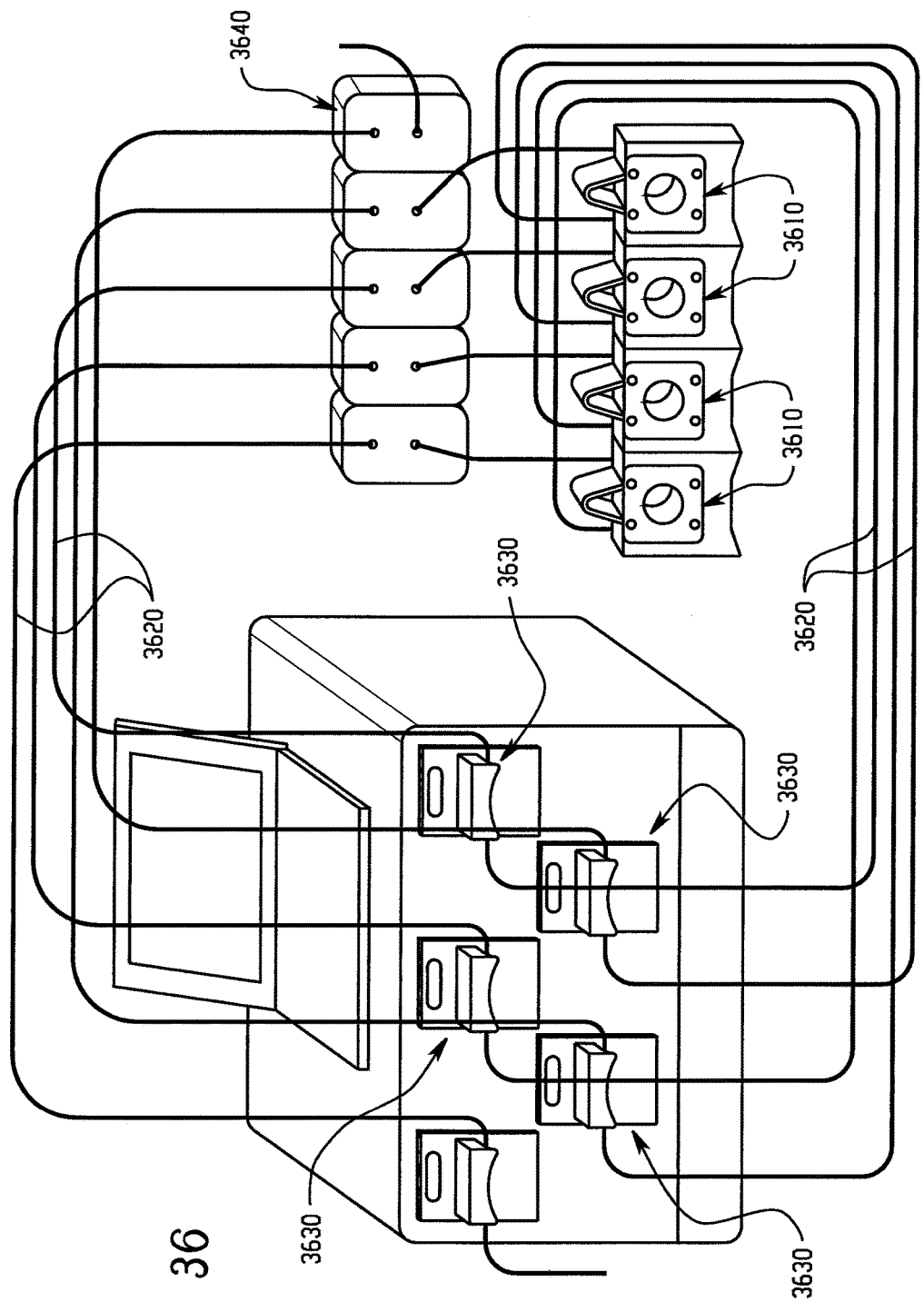
FIG. 36 illustrates an exemplary embodiment of a multi-stage acoustophoretic system according to the present disclosure. The acoustophoretic system includes a total of four stages fluidly connected to one another by tubing.

One embodiment of a multi-stage acoustophoretic system 3600 is shown in FIG. 36. The system 3600 is a four-stage system incorporating four acoustophoretic devices 3610. Each device 3610 can be considered a different clarification stage. Each acoustophoretic device 3610 can be constructed as described herein with a transducer-reflector pair(s) to create at least one multi-dimensional acoustic standing wave within each device. The acoustic chambers of each device can, in certain embodiments, be 1"×2". The nominal flow rate through the system can be about 4 L/hour.

In the system 3600 depicted in FIG. 36, the stages 3610 are connected to each other in series, with each device/stage 3610 being connected to adjacent stages by tubing 3620 running therebetween. Attaching adjacent stages to one another using tubing (as opposed to directly connecting the device of each stage to adjacent devices) provides for better separation of fluid and particular. A pump 3630 may be provided between each device, and additional pumps can be provided upstream of the first device and downstream of the last device. In this regard, it is noted that in the four-stage system 3600 of FIG. 36, five pumps 3630 would be used for the four devices/stages 3610. In addition, a flowmeter 3640 is present adjacent each pump 3630. As illustrated here, five flowmeters are present. Thus, fluid flow is through a feed pump, then a flowmeter, then the first clarification stage, then a pump, then a flowmeter, etc., ending with a final pump and a flowmeter.

As illustrated in FIG. 37A, the individual device stages 3610 are physically located side-by-side, and are physically connected to each other. This is not required—the stages can be separated from each other, and simply be fluidly connected by tubing. FIG. 37B is a rear view of a single stage 3610.

The multi-dimensional acoustic standing wave(s) created in each acoustophoretic device of the multi-stage acoustophoretic system can have a different frequency from the other stage(s), either higher or lower, which can be particularly useful for separating particles of different sizes or contrast factors or for otherwise selectively filtering certain particles. The frequencies of the multiple acoustic standing waves can be varied as desired to send different sizes and/or concentrations of materials to different stages of the system, thereby improving the efficiency of the process. The frequency of any stage can be equal to, or different from, each other stage as well. It is particularly contemplated that the frequencies of all of the stages are within one order of magnitude of each other.

FIG. 37C shows a cross-sectional diagram of one of the device/stages 3610. This device can be used to ameliorate some of the problems with a fluid at low particle Reynolds numbers, and create a more uniform flow through the device. The device 3610 has upward, vertical flow through the acoustic chamber. The acoustic chamber also has two opposing dump diffusers 3612 and a collector design which provides a vertical plane or line of flow symmetry. Generally, the cross-section of the device in the flow direction is circular or rectangular. The acoustic chamber is empty, i.e. there is nothing within the chamber, and fluid flows through the acoustic chamber. At least one permeate outlet 3614 is present at the upper end of the acoustic chamber. At least one solids outlet 3616 is present at the lower end of the acoustic chamber. A shallow wall 3618 is present at the lower end of the acoustic chamber, and leads to the solids outlet 3616. The shallow wall is angled relative to a horizontal plane, such as the bottom of the acoustic chamber. At least one ultrasonic transducer (not shown) is present on a sidewall of the acoustic chamber, and at least one reflector (not shown) is present on the sidewall opposite the ultrasonic transducer.

This device 3610 includes a symmetrical, dual dump diffuser, plenum inlet configuration. Here, two dump diffusers 3612 are placed on opposite sides of the device. Each dump diffuser has a plenum/chamber with an upper end 3620 and a lower end 3622. The plenum volume provides flow diffusion and dramatically reduces incoming flow non-uniformities. An inlet flow port 3624 is located above the lower end 3622, and at least one flow outlet 3626 is located at the lower end of the plenum. A solid wall 3628 is present at the upper end of the plenum. These dump diffuser flow outlets can be in the form of slots or a line of holes, and they are placed above the bottom of the acoustic chamber. The diffusers 3612 provide a flow direction normal to the axial direction of the acoustic standing waves generated by the ultrasonic transducer. The acoustic chamber inlets are also arranged so that they are in opposing locations, so that the horizontal velocity will decrease to zero in the center of the acoustic chamber.

The dump diffusers eliminate downward flow in the acoustic chamber. The mixture fills up the plenum in the dump diffuser and then flows horizontally into the acoustic chamber, where the mixture flows vertically upwards past the acoustic standing waves. The dump diffuser reduces/eliminates flow pulsations and flow non-uniformities that result from pumps, hosing and horizontal inlet flow where gravity effects dominate. The dump diffuser brings the heavier mixture into the acoustic chamber below the ultrasonic transducer and the nodal clusters that form in the ultrasonic standing waves. This minimizes any disturbances of the clusters set up by inflowing material.

The vertical plane or line of symmetry is aligned with gravity forces. Also shown are flow streamlines which are desirably symmetrical, since this minimizes non-uniformities, eddy disturbances, circulation, and disturbance of clusters falling through the solids outlet 3616 to be collected. Symmetry also maximizes gravity forces in the inlet flow distribution and particle collection process. Because it is heavier than the permeate exiting at the top of the device, the (relatively) heavy incoming mixture comes in near the bottom of the acoustic chamber, spreads out across the bottom of the chamber due to gravity forces, and provides near uniform velocity profiles from bottom to top. The horizontal velocity of the mixture will decrease to zero as it approaches the center of the acoustic chamber due to the dual opposing inlet flows. This assures minimum interference between the chamber flow and dropping particle clusters. A uniform velocity provides the best separation and collection results because the lateral acoustic forces have to overcome particle drag for the clusters to grow and continuously drop out of the acoustic chamber. This also eliminates the need for an inlet flow distributor.

As the particle clusters drop out, the axial acoustic forces associated with the standing wave will keep the clusters intact. This assures rapid dropping of the clusters with high terminal velocities, on the order of 1 cm/sec. This is extremely fast compared to the chamber flow velocities, which are on the order of 0.1 cm/sec to 0.3 cm/sec. The shallow wall angle means the cylindrical particle clusters have to drop only a very short distance before they exit the acoustic chamber, so that little dispersion of the clusters occurs. Ideally, the system operates with 3 to 12 crystal vibration nodes per square inch of transducer. The symmetry, minimum flow disturbance in the central collection region, and shallow collector walls provide good collection without the need for baffles/laminar plates.

The present disclosure will further be illustrated in the following non-limiting working examples, it being understood that these examples are intended to be illustrative only and that the disclosure is not intended to be limited to the modules, devices, conditions, process parameters and the like recited herein.

EXAMPLES

Various mixtures of CHO cells in cell culture media were filtered.

Example 1

The acoustophoretic separation process was compared to depth flow filtration (DFF). First, a baseline of DFF capacity was obtained by performing two rounds of clarification, a primary clarification and a secondary clarification. The setup for this baseline is illustrated in FIG. 38.

The pressure drop was measured during the two rounds. The separation apparatus was operated at 145 LMH (liters/m²/hour). The pressure was measured at three different locations P1, P2, and P3. Located between each set of sensors was a filter. The filter used during the primary clarification was a D0HC filter, and the filter used in the secondary clarification was a X0HC filter, both available from Millipore.

A mixture of CHO cells and culture media were flowed through the filters, and the permeate was then collected in a tank. The CHO cells were removed by the filters. The feed had a total cell density (TCD) of $6.34 \times 10^6$ cells/mL and a turbidity of 815 NTU. The final permeate in the third tank had a turbidity of 1.75 NTU.

Figure 38:
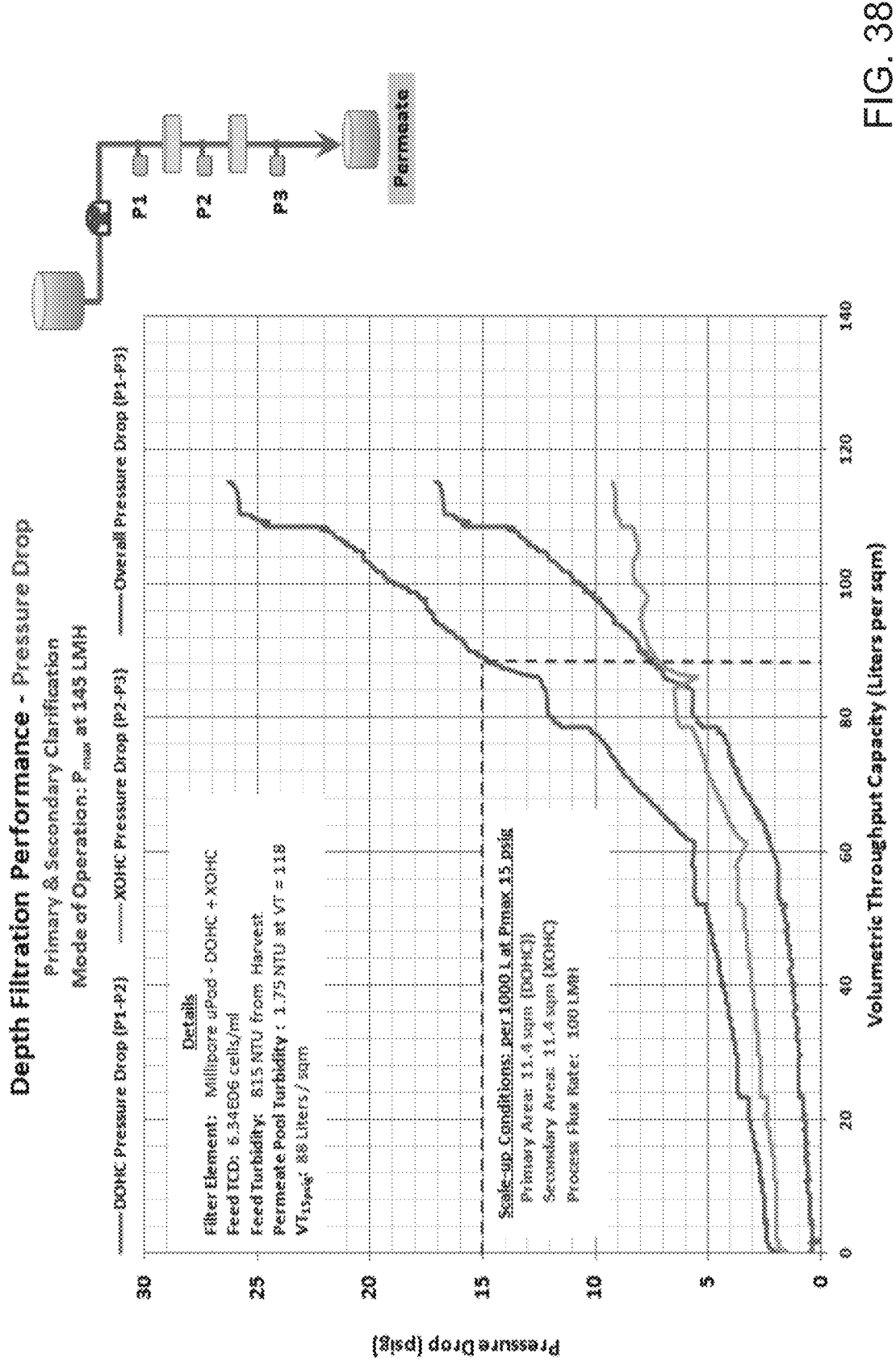
FIG. 38 is a performance chart showing the pressure drop for a system of the present disclosure having three acoustophoretic devices in series in a first experiment. The y-axis is pressure drop in psig, and runs from 0 to 30 in intervals of 5. The x-axis is volumetric throughput capacity in liters per square meter, and runs from 0 to 140 in intervals of 20.

FIG. 38 is a performance graph showing the pressure drop versus volumetric throughput capacity. The pressure drop in the primary filter was lowest at low throughput, then became greater than the pressure drop in the secondary filter above approximately 88 L/m² capacity. The total pressure drop is the top line in the graph. A pressure drop of 15 psig would be attained at a volumetric throughput of 88 L/m² (indicated by dashed lines). This indicates that if scaled up with a maximum pressure drop of 15 psig (Pmax=15 psig), then the area of the filter for the primary clarification and for the secondary clarification would each need to be 11.4 m².

Example 2

Next, the two-step DFF described in Example 1 was compared to a two-step clarification process in which the primary clarification was performed by acoustic wave separation (AWS) and the secondary clarification was performed by DFF. This is described in FIG. 39.

As indicated there, in the two-step DFF, each filter had an area of 11 m². Each filter was operated with a pressure drop of 7.5 psig. The volumetric throughput (VT) at 7.5 psig ($VT_{7.5}$) was 84 L/m² for each filter.

The acoustophoretic system used to perform the AWS was made up of three acoustophoretic devices as illustrated in FIG. 8 and linked in series, such as those depicted in FIG. 36. The transducer in each device was 1 inch by 1 inch. The system had a total acoustic volume of 49 cm³. The AWS system was paired with a DFF filter having a total area of 6 m². Because there is no pressure drop in the AWS system, the DFF filter could be operated at a pressure drop of 15 psig, resulting in a $VT_{15}$ of 160 L/m².

The feed had a total cell density (TCD) of $6.7 \times 10^6$ cells/mL and a turbidity of 835 NTU, and 77% cell viability. The feed rate to the acoustophoretic system was 4 kg at 2.5 liters per hour (LPH).

The results for the primary clarification using the AWS system are shown in FIG. 39. The acoustophoretic system achieved 91% TCD reduction, 90% turbidity reduction, and 91.2% recovery of protein. The graph at the bottom left is percent reduction versus time, and shows that the AWS system operated consistently during the test.

Example 3

The same experiment as described in Example 2 was performed again, but with a higher cell density. The feed had a higher TCD of $15.6 \times 10^6$ cells/mL and a turbidity of 3608 NTU, and 68% cell viability. This is described in FIG. 40.

The two-step DFF process used filters of 38 m² and 17 m², respectively. As indicated, the $VT_{75}$ was 26 L/m² for the primary clarification and 58 L/m² for the secondary clarification. In the AWS-DFF process, the AWS system had only two acoustophoretic devices in series (not three as in Example 2), with a total acoustic volume of 33 cm³. The DFF filter had a total area of 11 m², and a $VT_{15}$ of 85 L/m². The feed rate to the acoustophoretic system was 8 kg at 2.5 liters per hour (LPH).

The results for the primary clarification using the AWS system are shown in FIG. 38. The acoustophoretic system achieved 94% TCD reduction, 91% turbidity reduction, and 92% recovery of protein. The graph at the bottom left is percent reduction versus time, and shows that the system operated consistently during the test. Higher cell densities were more difficult for the DFF device, as indicated by the lower VT. However, the acoustophoretic device was able to handle the higher density with a much lower reduction in VT.

Example 4

The feed had a TCD of $7.5 \times 10^6$ cells/mL and a turbidity of 819 NTU, and 88% cell viability. Clarification was performed using a three-stage acoustophoretic system as in Example 1.

The first stage reduced the cell density by 62%. The second stage reduced the remaining cell density by 87% (cumulative 95%). The third stage reduced the remaining cell density by 63% (cumulative 98%). Only two stages were needed to attain greater than 90% cell density reduction.

The first stage reduced the turbidity by 68% from 819 NTU to 260 NTU. The second stage reduced the remaining turbidity down to 54 NTU (cumulative 94%). The third stage reduced the remaining turbidity to 42 NTU (cumulative 95%). Only two stages were needed to attain greater than 90% turbidity reduction. This is important for secondary filtration processes further downstream.

The percent reduction for both cell density reduction and turbidity reduction was consistent over the entire time, meaning the device operated well on a continuous basis. Again, these are both important for secondary filtration processes further downstream, and for ultimately the chromatographic separation of monoclonal antibodies or recombinant proteins from the clarified fluid.

Example 5

Five different lots were tested through the three-stage system of Example 1. Each lot had its own cell size and density characteristics. The feeds had a TCD of 7 to $8.5 \times 10^6$ cells/mL, a turbidity of 780 to 900 NTU, and 82% to 93% cell viability. This example tested the consistency of performance of the system across different batches.

Over the five different lots, the turbidity of the permeate was reduced 84% to 86%, with a standard deviation of 1% after three passes. The cell density of the permeate was reduced 93% to 97%, with a standard deviation of 2% after three passes.

In other experiments not described here, it was found that the acoustic wave separation processes using a multi-dimensional acoustic standing wave did not affect the physical or chemical characteristics of protein or monoclonal antibodies recovered from the permeate.

Example 6

Next, the effect of voltage input on clarification performance was observed in a three-stage or a four-stage acoustophoretic device such as in FIG. 36.

A mixture of CHO cells and culture media were flowed through the stages of the device, and the permeate was then collected in a tank. The CHO cells were removed by the filters. The feed had a total cell density (TCD) of $25 \times 10^6$ cells/mL, a turbidity of 2048 NTU, and a cell viability of 72%. The feed flow rate was 30 mL/min and the solids draws were 2.34 mL/min for stage one, 1.41 mL/min for stage two, 0.94 mL/min for stage three, and 0 mL/min for stage four.

Figure 41:
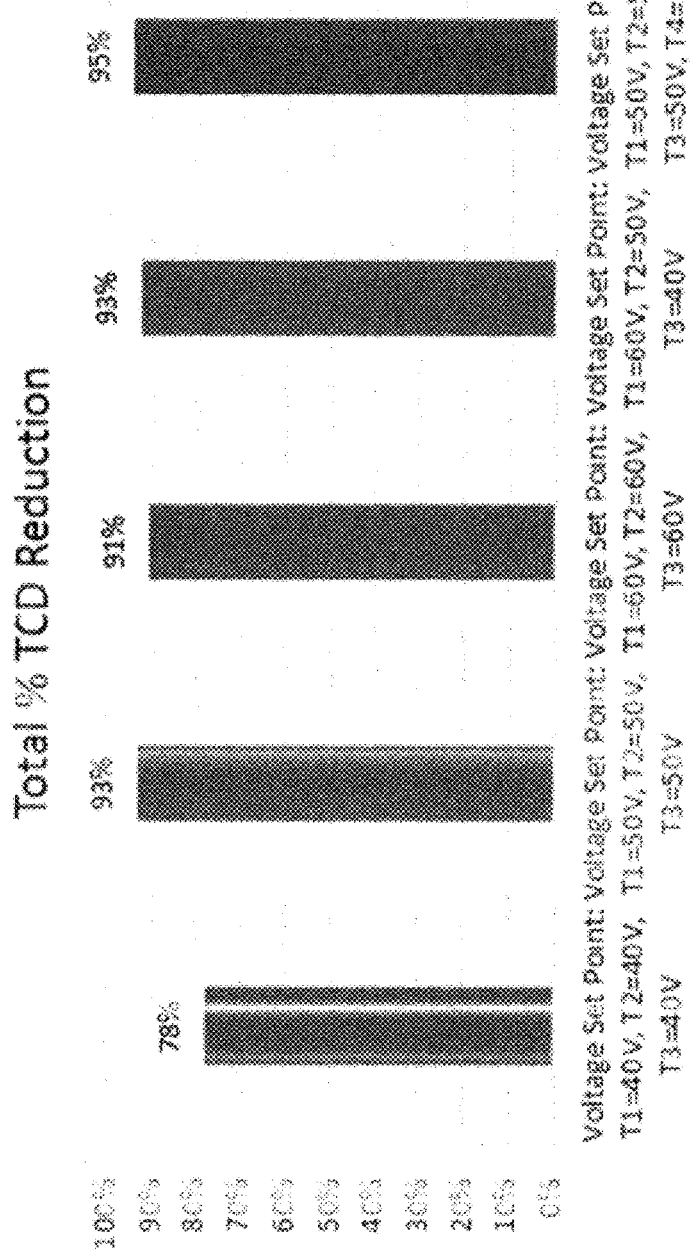
FIG. 41 is a graph showing the performance of multiple experimental test systems. The y-axis is total cell density (TCD) reduction percentage in increments of 10% from 0% to 100%. Along the x-axis are five distinct tests. The first bar represents a three-stage system with all three stages operated at 40V (test 1). The second bar represents a three-stage system with all three stages operated at 50V (test 2). The third bar represents a three-stage system with all three stages operated at 60V (test 3). The fourth bar represents a three-stage system with the first stage operated at 60V, the second stage operated at 50V, and the third stage operated at 40V (test 4). The fifth bar represents a four-stage system with all four stages operated at 50V (test 5).
Figure 42:
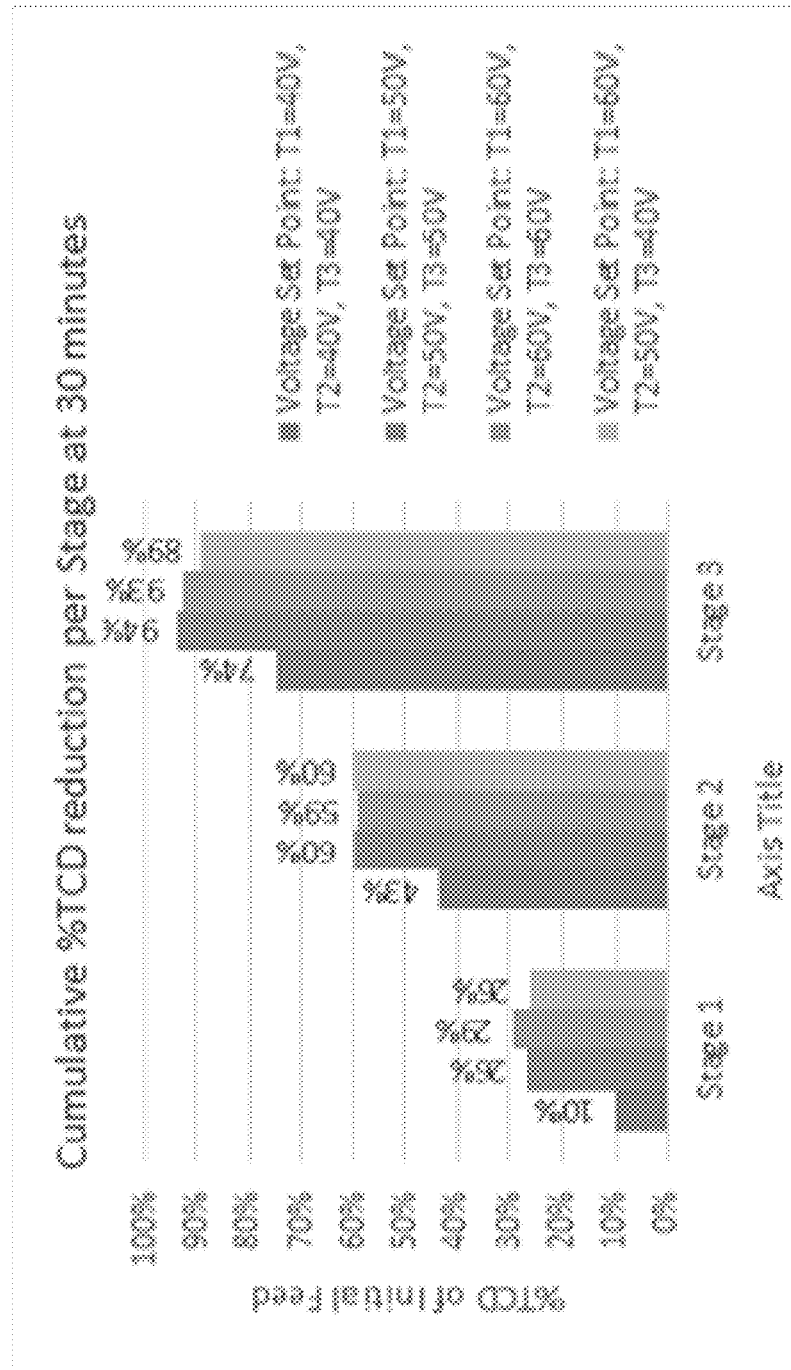
FIG. 42 is another graph showing the performance of each stage of FIG. 41. The y-axis is cumulative TCD reduction percentage per stage at 30 minutes in increments of 10% from 0% to 100%. Along the x-axis are the three stages of each system. The first series of bars represents the cumulative % reduction after the first stage of each system. The second series of bars represents the cumulative % reduction after the second stage of each system. The third series of bars represents the cumulative % reduction after the third stage of each system. Within each series of bars, the leftmost bar is test 1, the second bar from the left is test 2, and the second bar from the right is test 3, and the rightmost bar is test 4.
Figure 43:
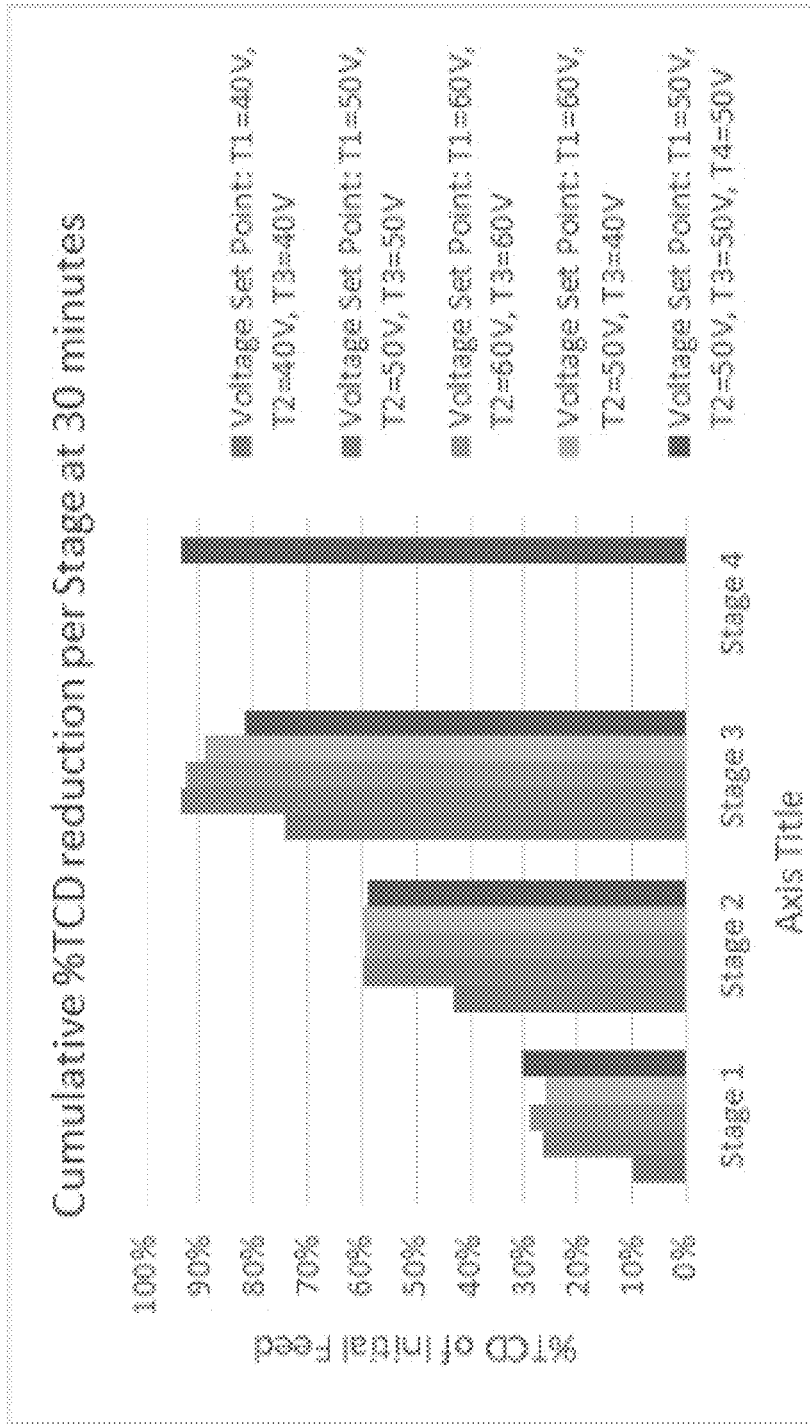
FIG. 43 is another graph showing the performance of each stage of the test systems of FIG. 41. The y-axis is cumulative TCD reduction percentage per stage at 30 minutes in increments of 10% from 0% to 100%. Along the x-axis are the three stages of each system. The first series of bars represents the cumulative % reduction after the first stage of each system. The second series of bars represents the cumulative % reduction after the second stage of each system. The third series of bars represents the cumulative % reduction after the third stage of each system. Within each series of bars, the leftmost bar is test 1, the second bar from the left is test 2, the middle bar is test 3, the second bar from the right is test 4, and the rightmost bar is test 5. For stage 4, the only bar shown is for test 5.

The TCD reduction after three and four stages of filtering are shown in FIG. 41. In this Figure T1 refers to the voltage in the first stage, T2 to the voltage in the second stage, T3 to the voltage in the third stage, and T4 to the voltage in the fourth stage. Five different test runs using different voltages in different stages are shown. For all voltage conditions of 50V and 60V, the system achieved a greater than 90% cell density reduction. The addition of the fourth stage yielded a high 95% reduction, lowering the TCD from $2.9 \times 10^6$ cells/mL after three stages to $1.3 \times 10^6$ cells/mL after four stages. As can be seen in FIG. 42, voltages of 50V and 60V yielded the best performances through each stage. As can be seen in FIG. 43, adding a fourth stage at 50V increased the TCD reduction by 10% aggregate. Generally, a voltage of 50V to 60V should be used in the first and/or second stages to obtain high TCD reduction.

Figure 44:
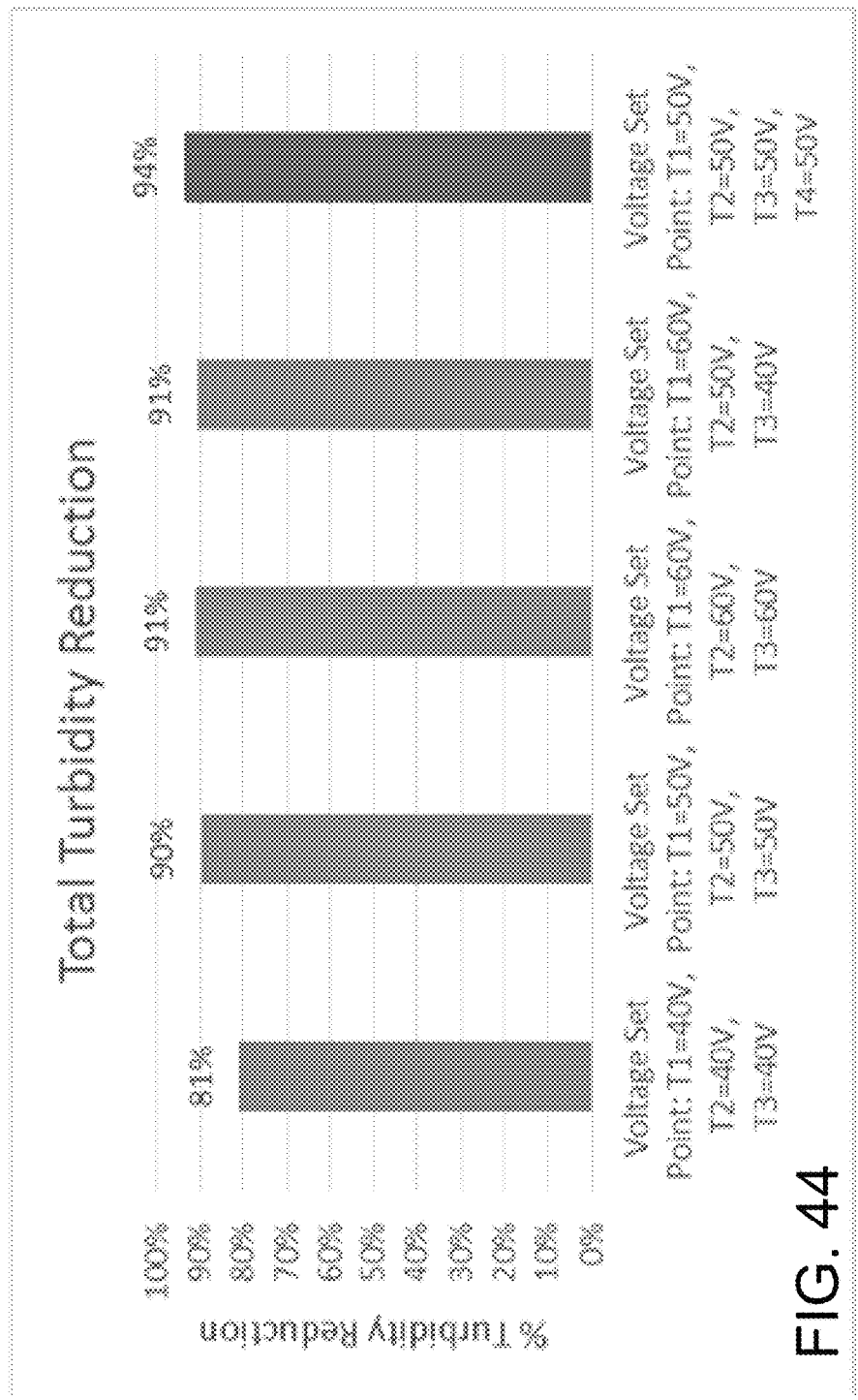
FIG. 44 is another graph showing the performance of the five test systems of FIG. 41. The y-axis is total turbidity reduction percentage in increments of 10% from 0% to 100%. Along the x-axis are five distinct tests. The first bar represents a three-stage system with all three stages operated at 40V (test 1). The second bar represents a three-stage system with all three stages operated at 50V (test 2). The third bar represents a three-stage system with all three stages operated at 60V (test 3). The fourth bar represents a three-stage system with the first stage operated at 60V, the second stage operated at 50V, and the third stage operated at 40V (test 4). The fifth bar represents a four-stage system with all four stages operated at 50V (test 5).

The total turbidity reduction after three and four stages of filtering are shown in FIG. 44. For all voltage conditions of 50V and 60V, the system achieved a greater than 90% turbidity reduction. The addition of the fourth state yielded a 94% reduction, lowering permeate from 390 NTU after three stages to 177 NTU after four stages.

In summary, the 50V and 60V operating conditions yielded higher and near-equivalent clarification over the 40V operating condition, and use of the 40V operating condition in the third stage after 50V/60V in the first and second stages lowered the clarification efficiency.

Example 7

Next, similar to Example 1, the acoustophoretic separation process was compared to depth flow filtration (DFF) to determine the effect of DFF performance on acoustic wave separation (AWS) performance.

A mixture of CHO cells and culture media were flowed through two filters, a D1HC filter and a X0HC filter, both available from Millipore, and the permeate was then collected in a tank. The CHO cells were removed by the filters. The feed had a total cell density (TCD) of $24.7 \times 10^6$ cells/mL and a turbidity of 2850 NTU. The final permeate in the tank had a turbidity of 4.9 NTU.

Figure 45:
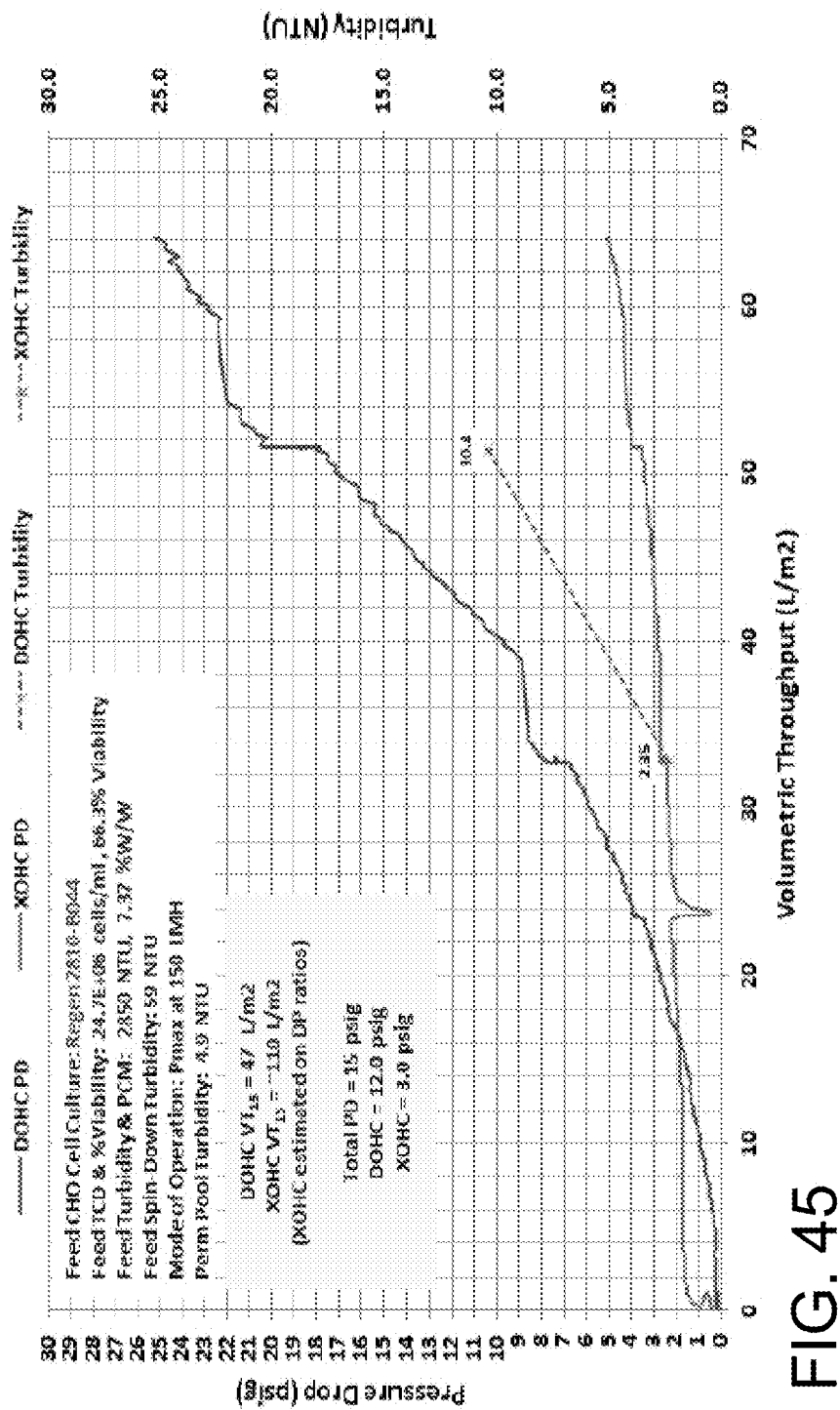
FIG. 45 is a graph showing the performance or a volume throughput (VT) of a fifth experimental system. The top line along the right side of the graph represents the DOHC filter pressure drop. The dotted line extending from the DOHC pressure drop line represents the DOHC filter turbidity. The bottom line along the right side of the graph represents the XOHC filter pressure drop. The dotted line extending from the XOHC pressure drop line represents the XOHC filter turbidity.

FIG. 45 is a performance graph showing the pressure drop versus volumetric throughput capacity. The profiles in FIG. 45 were plotted per stage based on the total filter area in each stage. The volumetric throughput capacity was calculated at 23 cm². The pressure drop in the D0HC filter was lowest at low throughput, then became greater than the pressure drop in the X0HC filter above approximately 16 L/m² capacity. A pressure drop of 15 psig would be attained at a volumetric throughput of 47 L/m² for the D0HC filter and approximately 110 L/m² for the D0HC filter (estimated based on pressure-drop ratios—the D0HC filter accounting for 12.0 psig of the total 15.0 psig pressure drop and the X0HC filter accounting for the remaining 3.0 psig).

Figure 46:
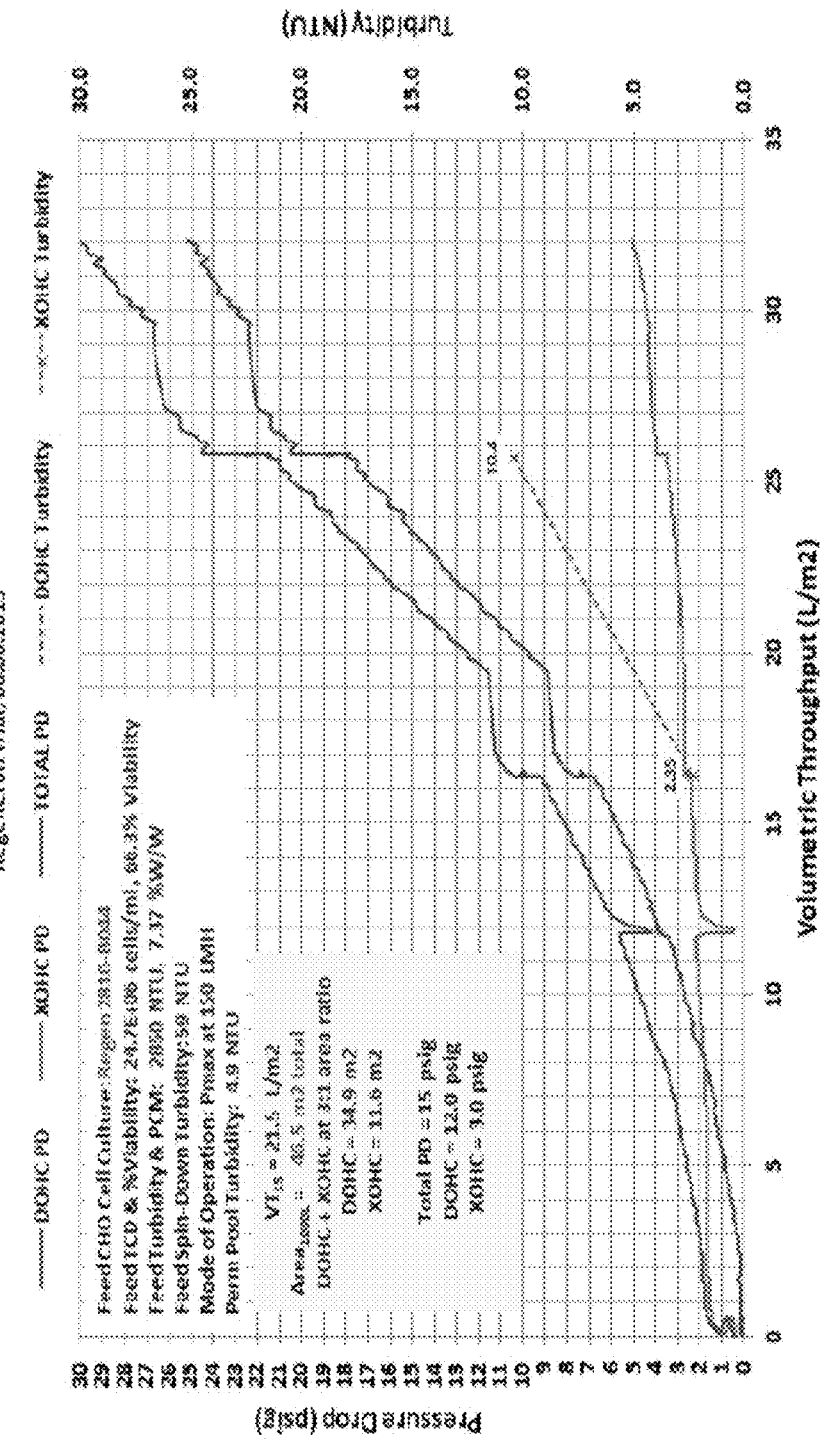
FIG. 46 is another graph showing the performance or volume throughput (VT) of the fifth experimental system.

FIG. 46 is a performance graph showing the pressure drop versus volumetric throughput capacity. The profiles in FIG. 46 were plotted for the total filter area in series (i.e., across all stages). The volumetric throughput capacity was calculated at 46 cm². The pressure drop in the D0HC filter was lowest at low throughput, then became greater than the pressure drop in the X0HC filter above approximately 8 L/m² capacity. The total pressure drop is the top line in the graph. A pressure drop of 15 psig would be attained at a volumetric throughput of 21.5 L/m². This indicates that if scaled up with a maximum pressure drop of 15 psig (Pmax=15 psig), then the area of the filter for the primary clarification and secondary clarifications would need to be 46.5 m² total with a D0HC:X0HC filter size ratio of 3:1 (i.e., the D0HC filter would have an area of 34.9 m² and the X0HC filter would have an area of 11.6 m².

Example 8

Figure 47:
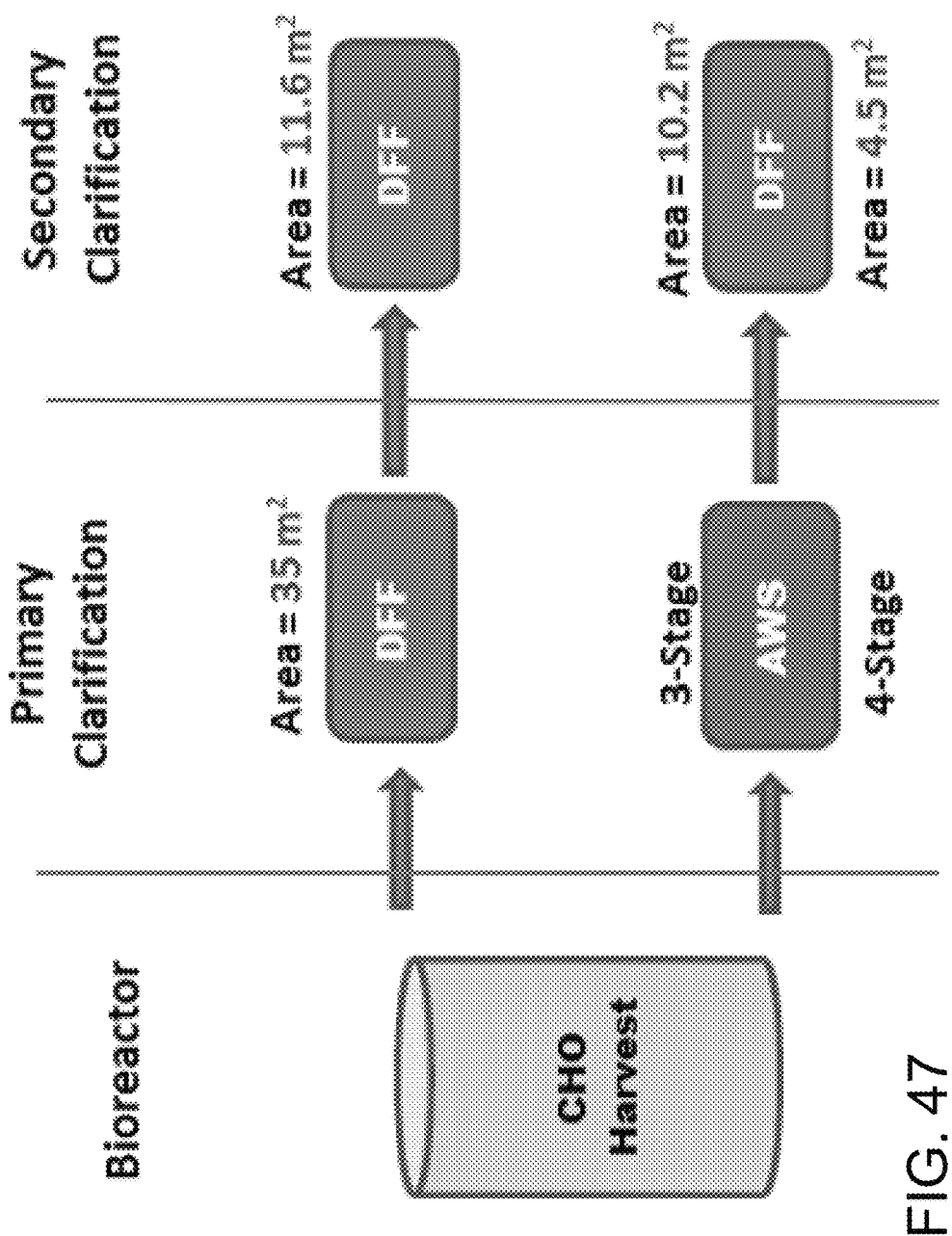
FIG. 47 is a graph showing the performance of a sixth experimental system.

Next, the two-step DFF described in Examples 6 and 7 were compared to a two-step clarification process in which the primary clarification was performed by acoustic wave separation (AWS) and the secondary clarification was performed by DFF. This is described in FIG. 47.

As indicated there, in the two-step DFF, the D0HC filter had an area of 34.9 m² and the X0HC filter had an area of 11.6 m², for a total area of 46.5 m². Each filter was operated with a pressure drop of 15 psig. The volumetric throughput (VT) at 15 psig ($VT_{15}$) was 47 L/m² for the D0HC filter and 110 L/m² for the X0HC filter. The turbidity of the permeate was 4.9 NTU.

Figure 37:
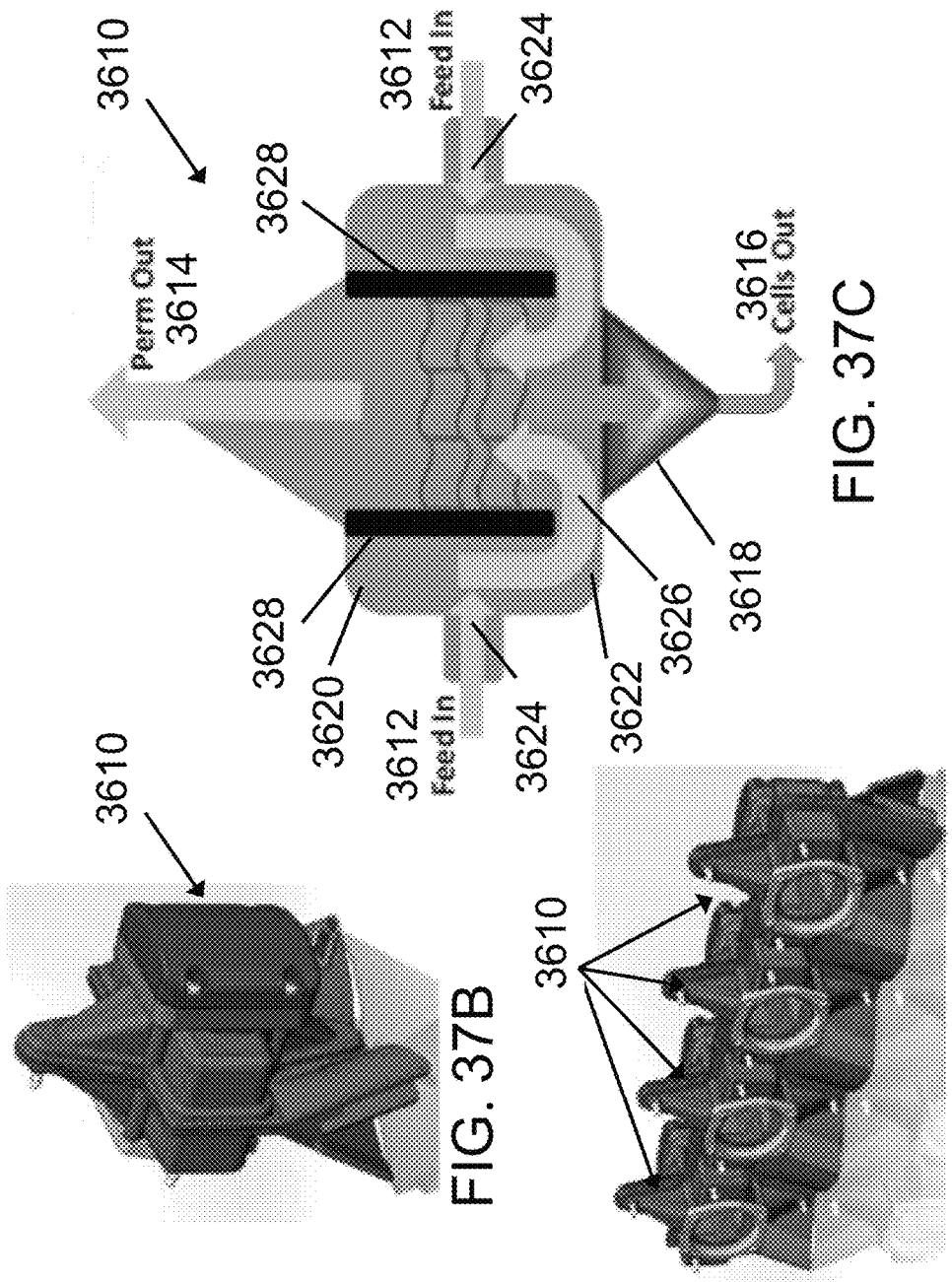
FIG. 37A illustrates an exemplary embodiment of four acoustophoretic devices/stages physically connected to one another for use in a multi-stage acoustophoretic system according to the present disclosure.
FIG. 37B illustrates an isolated view of one of the acoustophoretic devices/stages of FIG. 37A.
FIG. 37C is a cross-sectional diagram of one of the acoustophoretic devices/stages of FIG. 37A. The device includes opposing flow dump diffuser inlets generating flow symmetry and more uniform velocities.

Two different acoustophoretic systems were used to perform the AWS. The first acoustophoretic system was a three-stage system (i.e., made up of three acoustophoretic devices) as illustrated in FIG. 8 and linked in series, such as is depicted in FIG. 36 or FIG. 37. The second acoustophoretic system was a four-stage system (i.e., made up of four acoustophoretic devices) as illustrated in FIG. 36 or FIG. 37 and linked in series. The transducers used in each device of each system were 1 inch by 1 inch.

The first AWS system was paired with a DFF filter having a total area of 10.2 m². The area by stage was 7.6 m² (3×) and 2.6 m² (1×). Because there is no pressure drop in the AWS system, the DFF filter could be operated at a pressure drop of 15 psig, resulting in a $VT_{15}$ of 214 L/m². The feed had a total cell density (TCD) of 2.9×10⁶ cells/mL and a turbidity of 380 NTU. The turbidity of the permeate was 8.8 NTU.

The second AWS system was paired with a DFF filter having a total area of 4.5 m². The area by stage was 3.4 m² (3×) and 1.1 m² (1×). Again, because there is no pressure drop in the AWS system, the DFF filter could be operated at a pressure drop of 15 psig, resulting in a $VT_{15}$ of 490 L/m². The feed had a total cell density (TCD) of 1.3×10⁶ cells/mL and a turbidity of 176 NTU. The turbidity of the permeate was 11.4 NTU.

The first AWS system (the three-stage system) reduced the overall filter area by 78%, with a decrease of 12% in secondary clarification as compared to DFF for primary clarification (centrifuge is the current unit operation).

The second AWS system (the four-stage system) reduced the overall filter area by 90%, with a decrease of 60% in secondary clarification as compared to DFF-DFF. The acoustophoretic system achieved 91% TCD reduction, 90% turbidity reduction, and 91.2% recovery of protein. The graph at the bottom left is percent reduction versus time, and shows that the AWS system operated consistently during the test.

Figure 48:
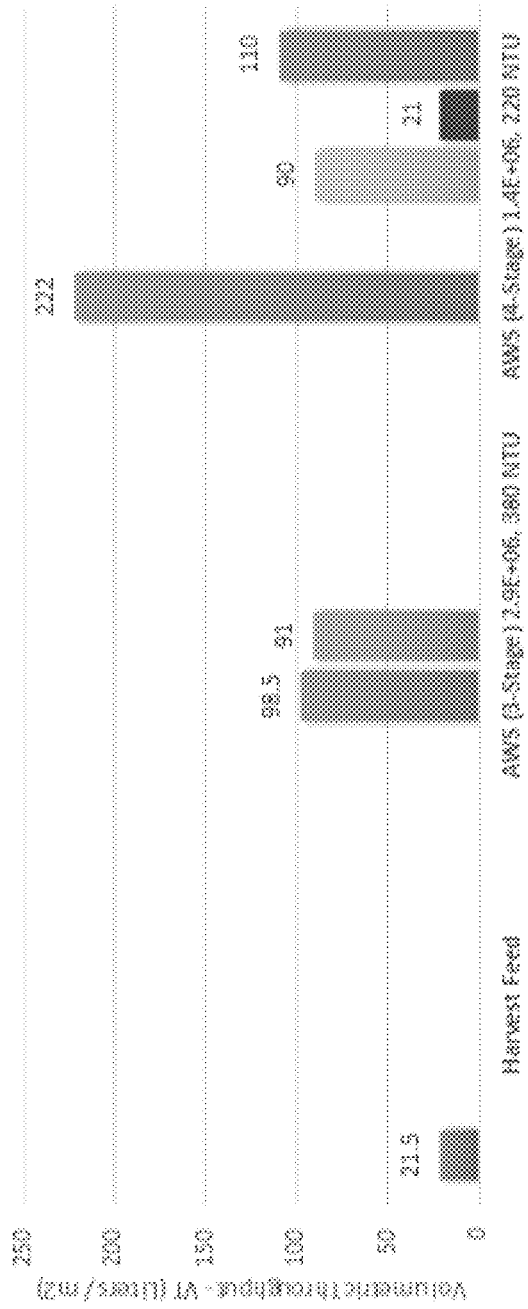
FIG. 48 is another graph showing the performance of the sixth experimental system utilizing depth flow filtration (DFF) and volume throughput (VT) as a performance indicator. The y-axis is volumetric throughput in L/m$^2$, and runs from 0 to 250 in intervals of 50. The bar labeled "harvest feed" is the throughput through a two-stage depth filter. The bars labeled "AWS (3-stage)" are the throughput through filters obtained from two different manufacturers after filtration through a 3-stage system. The bars labeled "AWS (4-stage)" are the throughput through filters obtained from four different manufacturers after filtration through a 4-stage system.

FIG. 48 shows a summary of the DFF filter performance. Harvest to DFF to DFF (primary and secondary) produced a very low volumetric throughput, so low that to process 1000 L would require almost 50 m² of filter area. The volumetric throughput of the DFF step after the third stage was increased by 100% with the addition of a fourth stage. TCD was decreased from 2.9×10⁶ cells/mL to 1.4×10⁶ cells/mL (~50% reduction). Turbidity was decreased from 338 NTU to 220 NTU (42% reduction). Centrate from the centrifuge was measured to have a TCD of 0.07×10⁶, a turbidity of 450 NTU, and a viable cell density (VCD) of 6%. High shear forces caused cell disruption, thereby increasing turbidity and lowering the VCD of remaining cells. Single-stage DFF results after four-stage AWS performed 50-90% below dual stage (C0HC+X0HC).

Example 9

Figure 49:
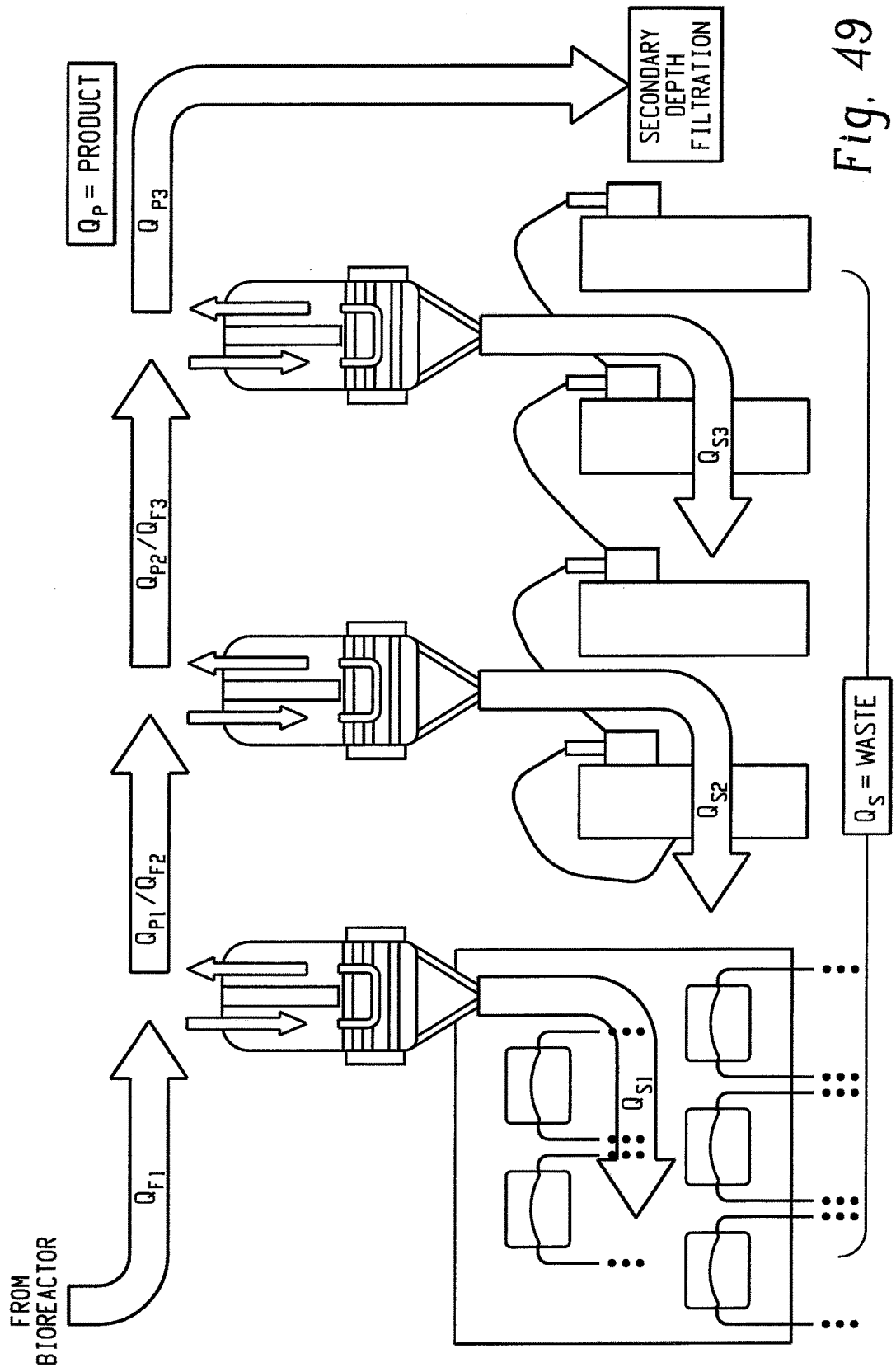
FIG. 49 illustrates an exemplary setup of a three-stage acoustophoretic system used as the experimental system for some performance testing of the present disclosure.

Next, the effect of feed flow rates ($Q_F$), total flow ratios ($Q_S/Q_F$), and solids flow ratios ($Q_{S\#}/Q_{S\#}$) on clarification performance was observed in a multi-stage acoustophoretic system. This is described in FIG. 49. As seen here, the $Q_{F\#}$ indicates the feed flow rate into a given acoustophoretic stage, the $Q_{P\#}$ indicates the permeate flow rate from the given acoustophoretic stage, and the $Q_{S\#}$ indicates the solids flow rate from the given acoustophoretic stage. The permeate flow rate of an upstream device is the feed flow rate into the subsequent acoustophoretic stage (e.g., $Q_{P1}=Q_{F2}$).

Using ten different cell lines, 135 individual runs were performed using a mixture of CHO cells and culture media having 27-98% cell viabilities, 2.8×10⁶ to 56×10⁶ cells/mL cell densities, 1.4 to 16.5% packed cell mass (PCM), and 30 to 9000 NTU feed turbidity.

Figure 50:
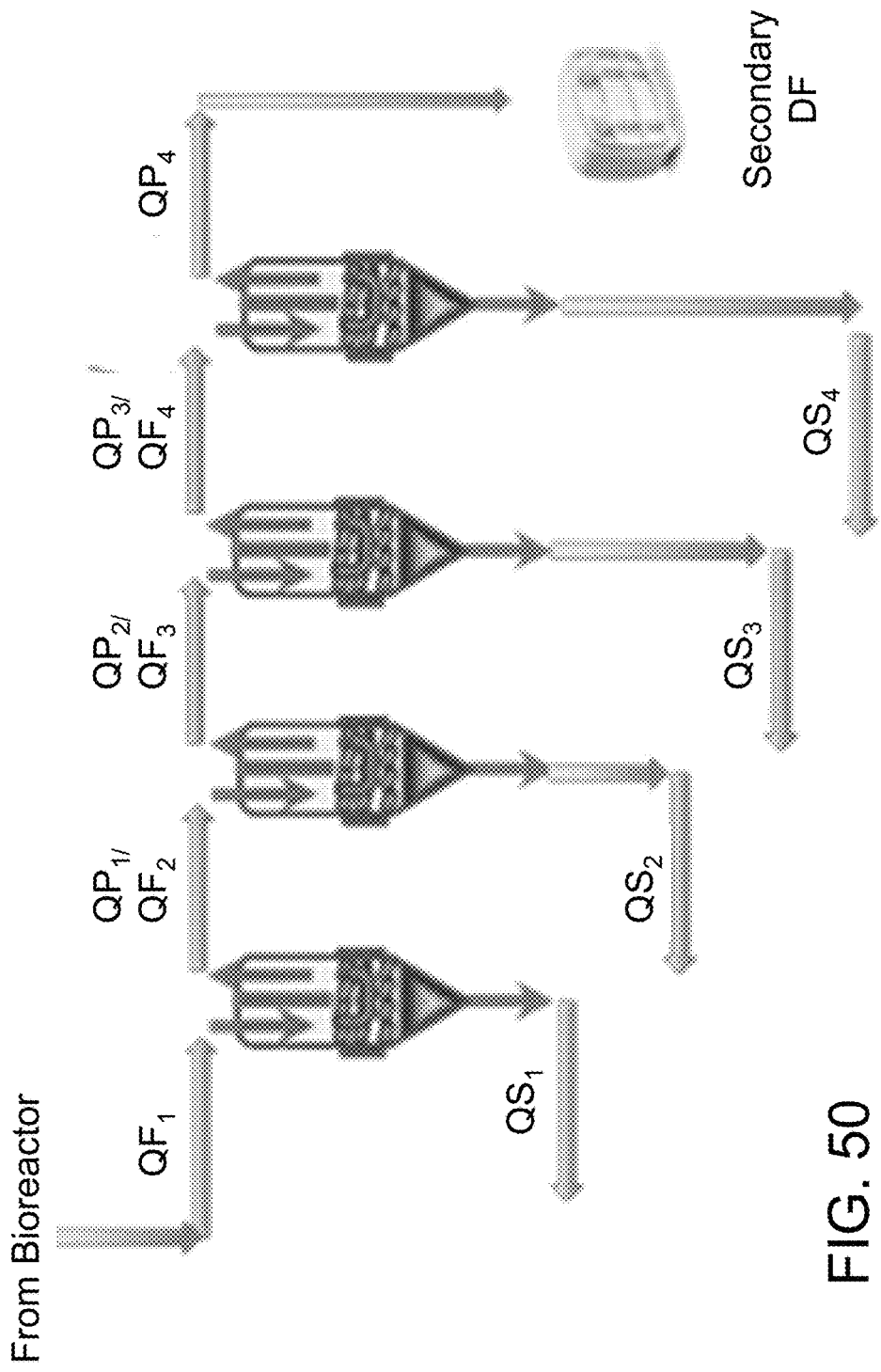
FIG. 50 illustrates an exemplary setup of a four-stage acoustophoretic system used as the experimental system for much of the performance testing of the present disclosure.
Figure 51:
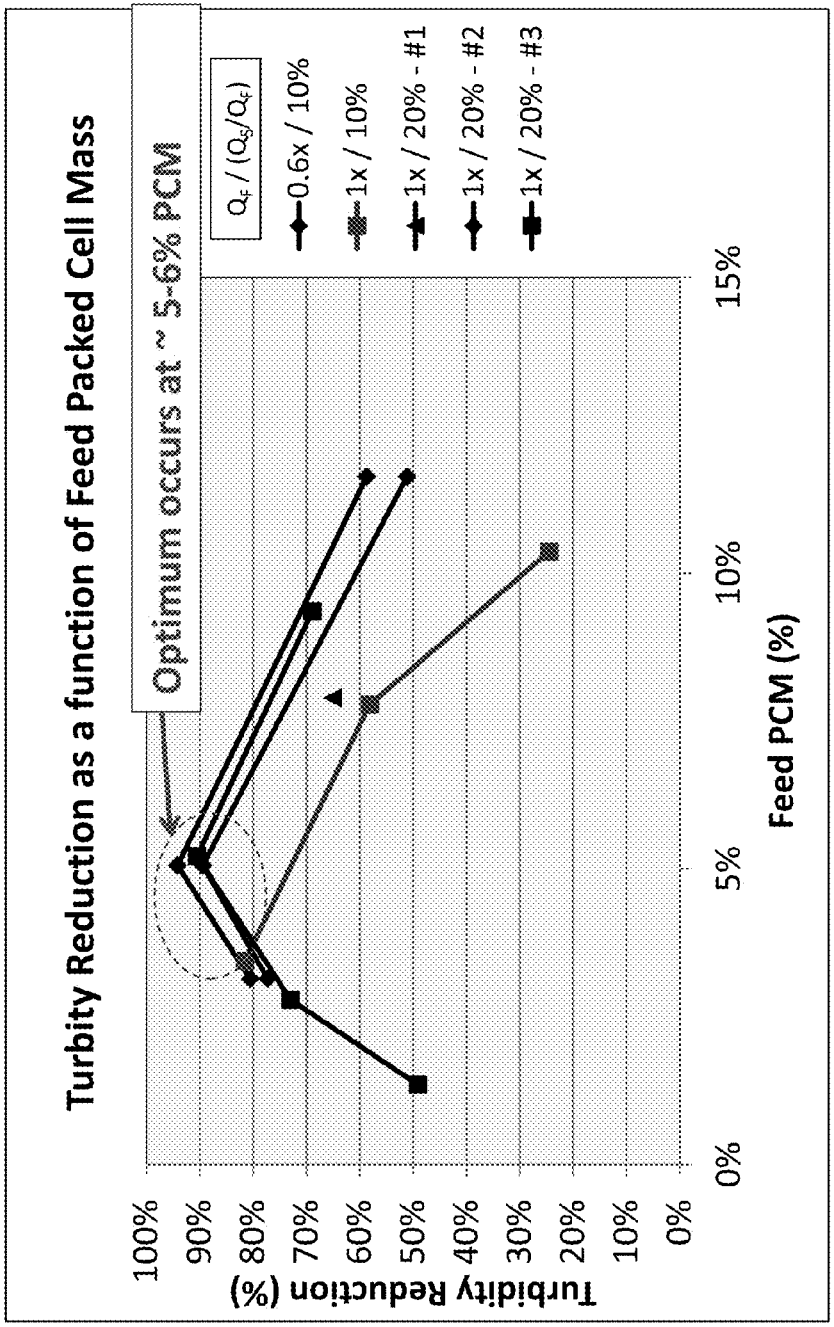
FIG. 51 is a graph showing turbidity reduction vs feed PCM for the system of FIG. 50.
Figure 52:
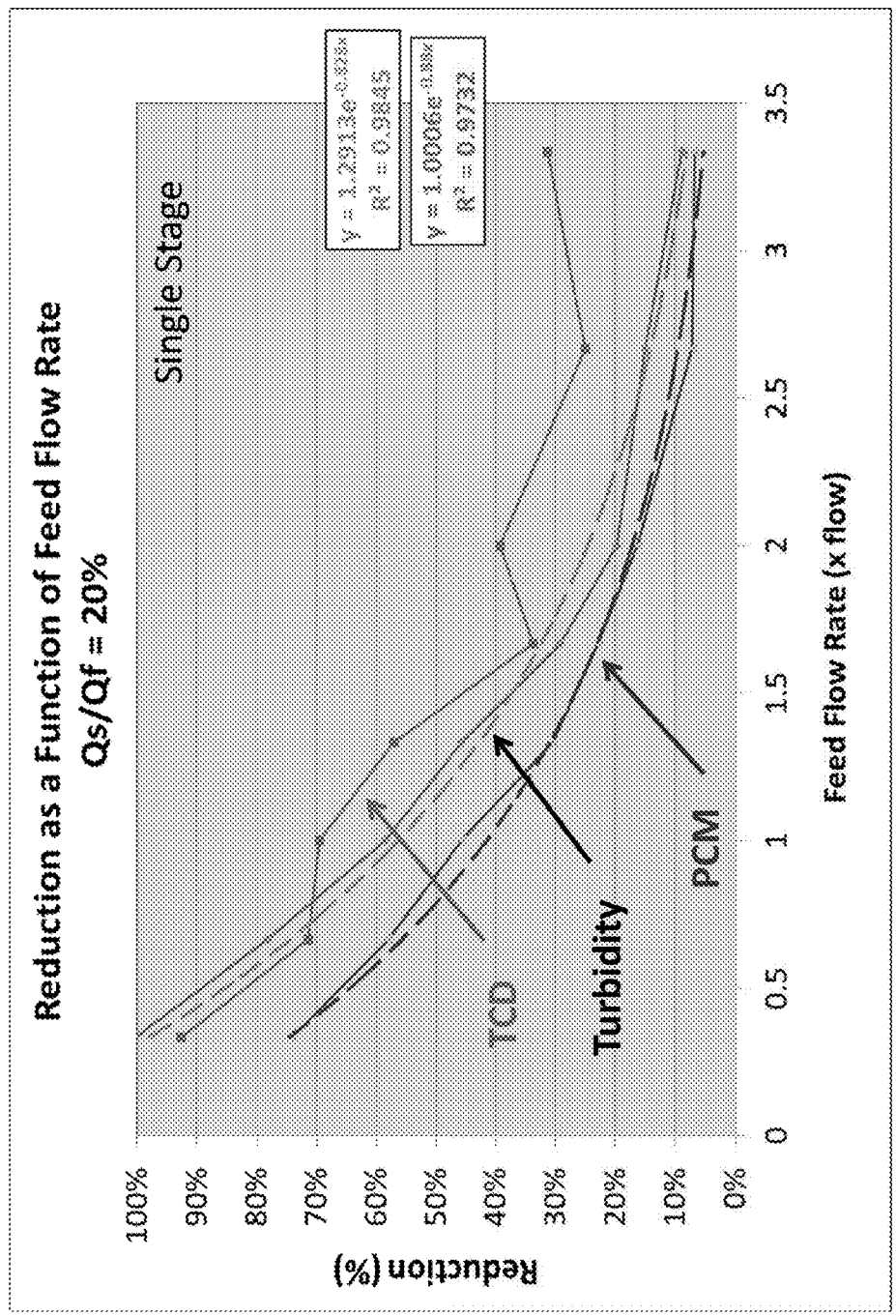
FIG. 52 is a graph showing percent reduction vs feed flow rate for three different factors (TCD, turbidity, PCM) for the system of FIG. 50.
Figure 53:
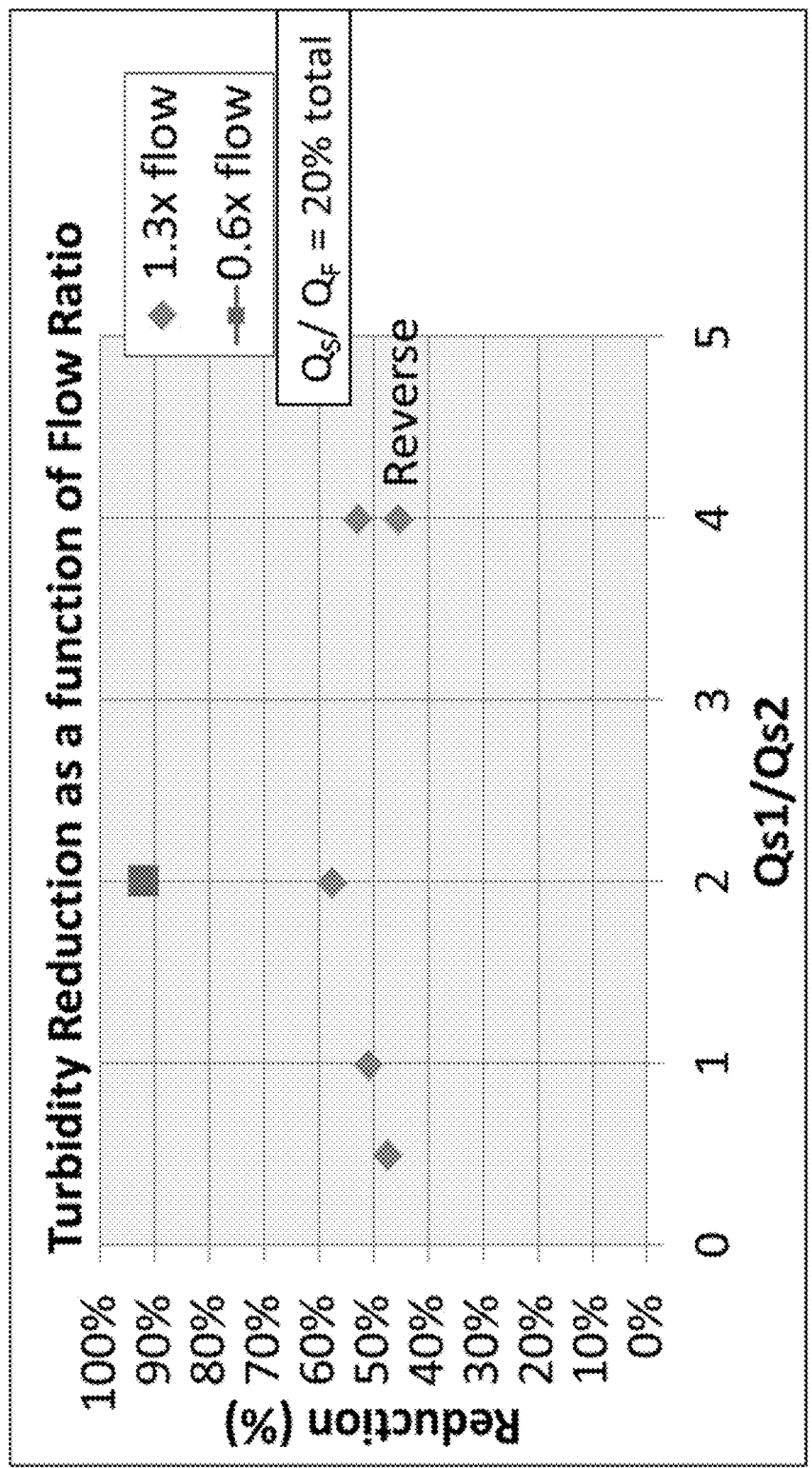
FIG. 53 is a graph showing turbidity reduction vs flow ratio for the system of FIG. 50.
Figure 54:
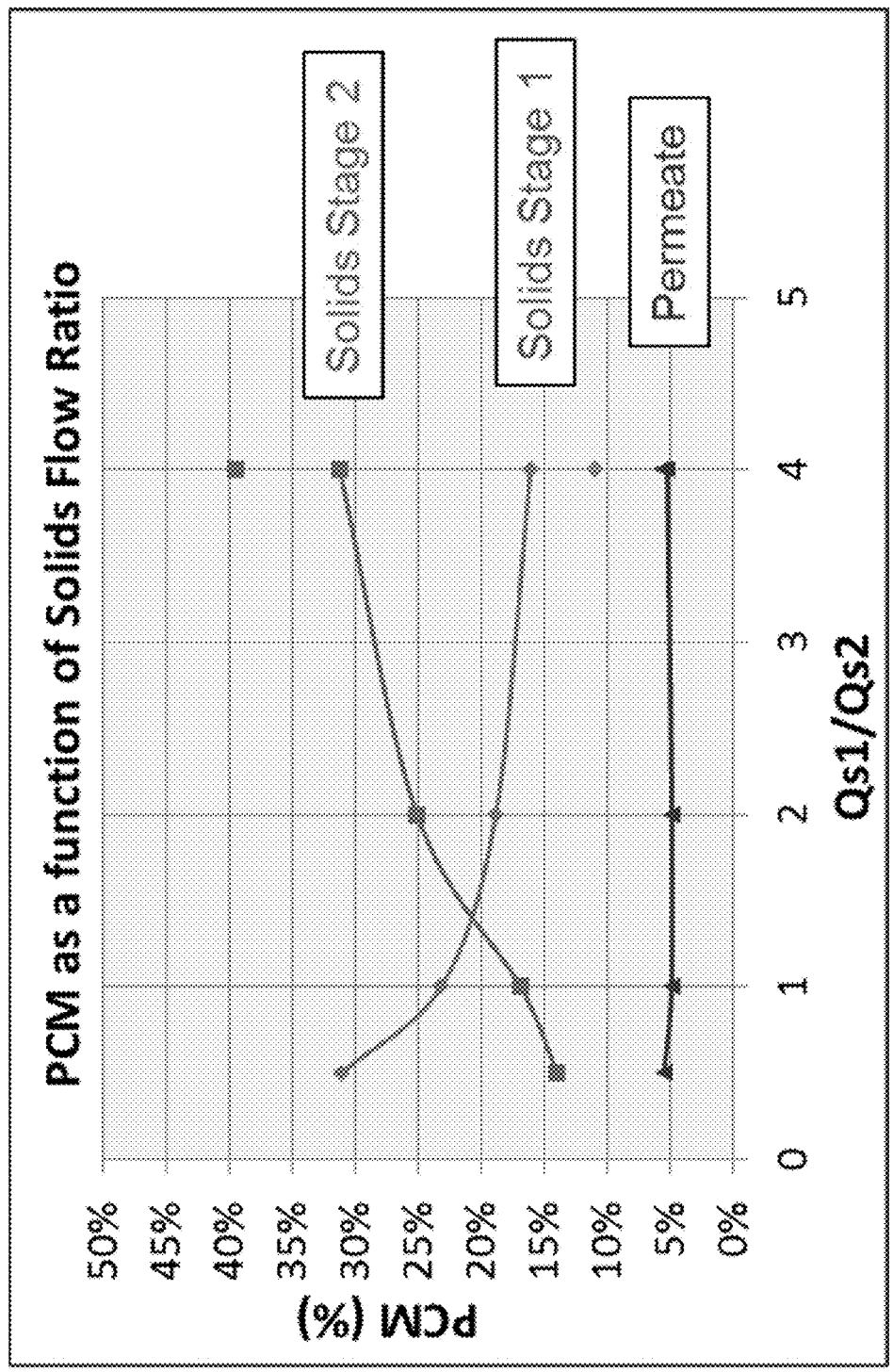
FIG. 54 is a graph showing PCM vs solids flow ratio for the system of FIG. 50.
Figure 55:
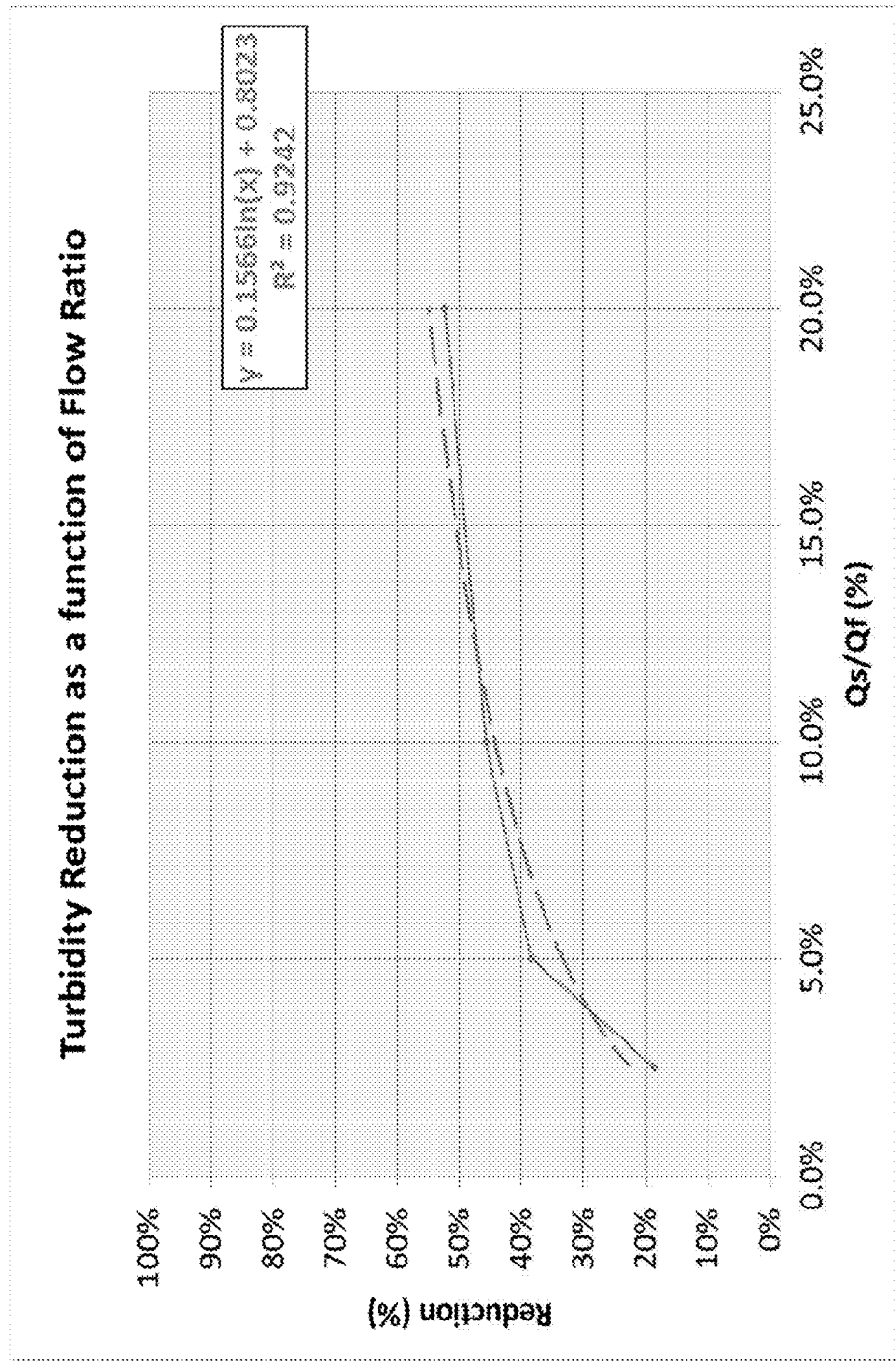
FIG. 55 is a graph showing turbidity reduction vs flow ratio for the system of FIG. 50.
Figure 56:
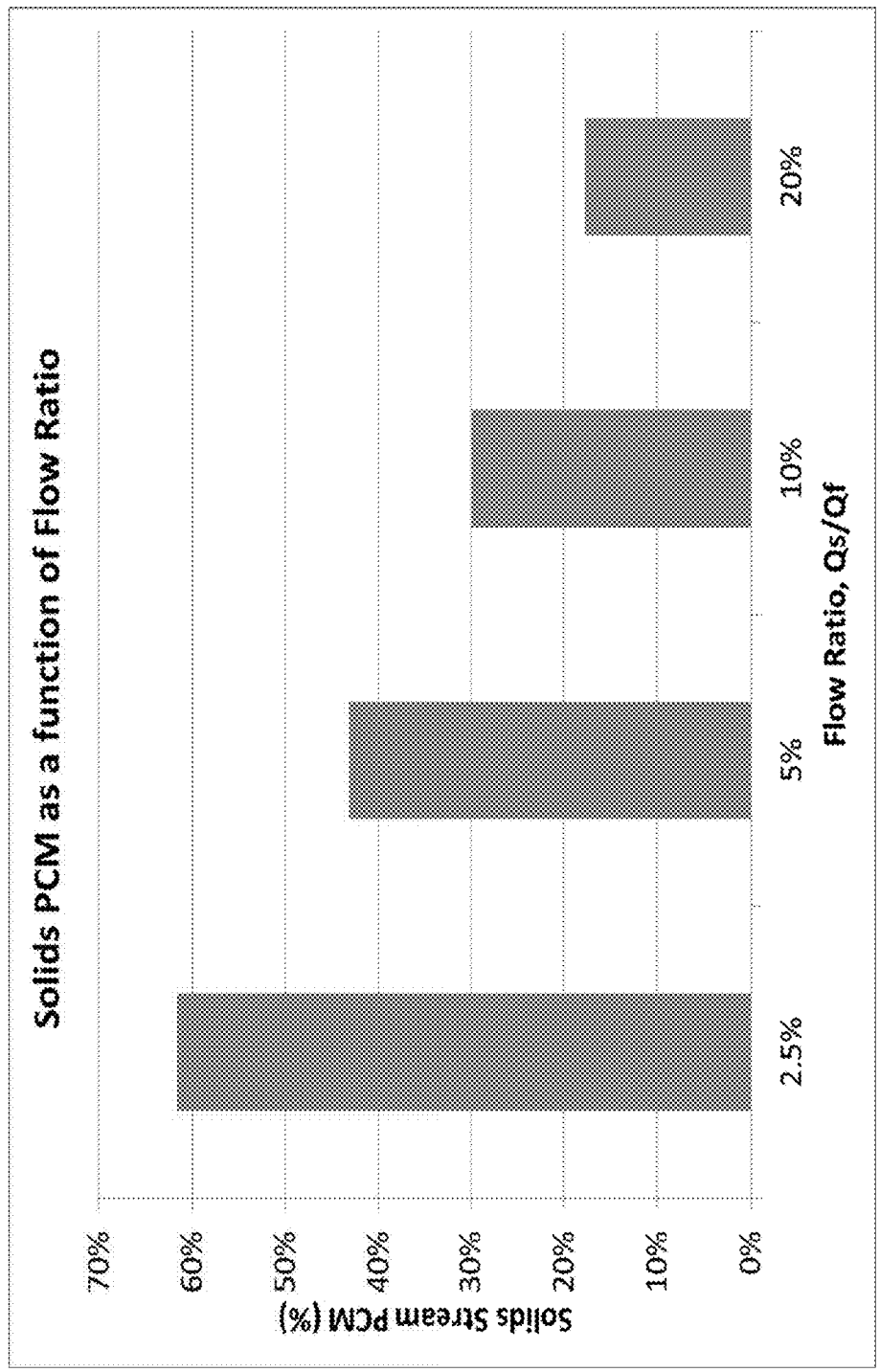
FIG. 56 is a bar graph showing solids PCM vs flow ratio for the system of FIG. 50.

FIG. 50 illustrates an exemplary four-stage setup. FIG. 51 shows the turbidity reduction as a function of the feed PCM. FIG. 52 shows the turbidity reduction as a function of the feed flow rate for a total flow ratio of 20%. FIG. 53 shows the turbidity reduction as a function of the solids flow ratio for a total flow ratio of 20%. FIG. 54 shows the PCM as a function of the solids flow ratio. FIG. 55 shows the turbidity reduction as a function of the solids flow ratio. FIG. 56 shows the solids PCM as a function of the solids flow ratio. The feed flow rate was found to greatly impact clarification. The total flow ratio was found to primarily impact yield, while impacting clarification somewhat. The optimized ratio was found to be (feed PCM/50% PCM solids stream). Decreasing the total flow ratio was found to improve yield and increase solids packing. The solids flow ratio was found to not have an impact on overall clarification, but was found to allow control over solids distribution between stages. The feed PCM was found to impact clarification and stage efficiency. The optimum feed PCM was found to be 5-6%, single stage, and higher % PCM is not an issue with multi-stage systems.

Example 10

Next, the effect of feed flow rates ($Q_F$) on clarification performance was observed in three- and four-stage acoustophoretic systems.

A mixture of CHO cells and culture media were flowed through both systems as a AWS "train" that was then processed using a DFF filter. The CHO cells were removed by the filters. The feed had a total cell density (TCD) of 35.8×10⁶ cells/mL, a turbidity of 4457 NTU, a PCM of 9.1%, and a viability of 91.9%.

Figure 57:
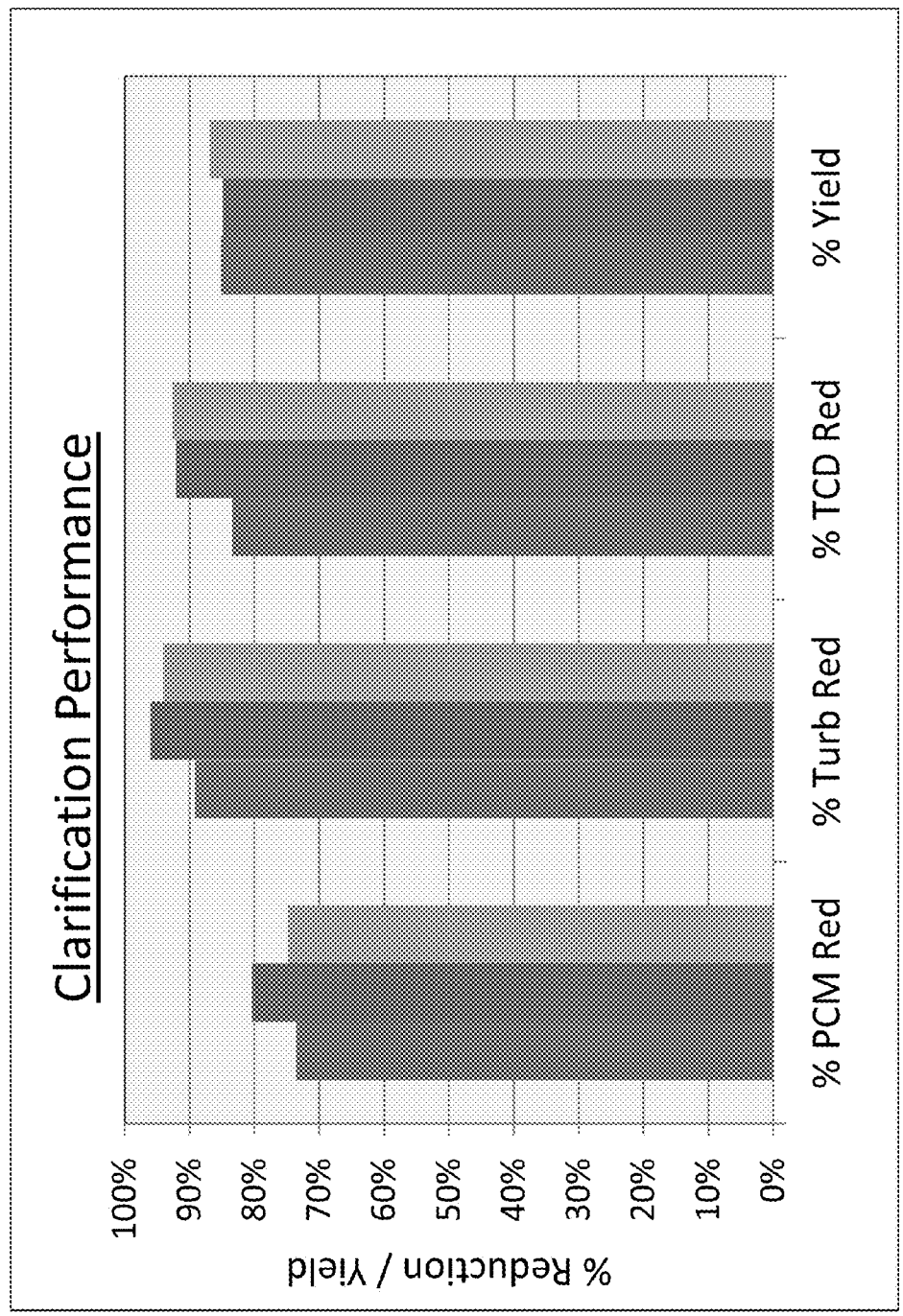
FIG. 57 is another graph showing the clarification performance for the system of FIG. 50. For each set of bars, the leftmost bar is $Q_F$=1.0×, 3-stage; the middle bar $Q_F$=0.6×, 3-stage; and the right bar is $Q_F$=1.0×, 4-stage.

The three-stage system used two runs with feed flow rates ($Q_F$) of 1.0× and 0.66×. The four-stage system used a single run with a feed flow rate ($Q_F$) of 1.0×. FIG. 57 shows the % PCM reductions, turbidity reductions, TCD reductions, and yield percentages. In each series, the leftmost bar represents the 1.0× three-stage system, the middlemost bar represents the 0.6× three-stage system, and the rightmost bar represents the 1.0× four-stage system The 0.6× three-stage system performed comparably to the 1.0× four-stage system, though all runs achieved >85% yield and >~90% turbidity reduction. Each permeate has a separate filtration chain. The full data recorded is provided below.

|  |  | AWS-Clarified Permeates | | |
|---|---|---|---|---|
|  | Feed | Run #1 | Run #2 | Run #3 |
| $Q_F$ |  | 1.0× | 0.6× | 1.0× |
| Stages |  | 3 | 3 | 4 |
| TCD (×10⁶ cells/mL) | 35.8 | 5.92 | 2.72 | 2.52 |
| Viability (μm) | 91.9% | 91.4% | 90.6% | 90% |
| Diameter | 17.5 | 18.1 | 17.7 | 17.8 |
| PCM | 9.1% | 2.4% | 1.8% | 2.3% |
| Turbidity | 4457 | 560 | 235 | 319 |

Again, the AWS performed much better than DFF to DFF and achieved a ~4× increase in volumetric throughput. The overall filtration is summarized below.

|  |  | Run #1 | Run #2 | Run #3 | Platform Direct Harvest |
|---|---|---|---|---|---|
| D0-X0 Results | D0HC (L/m²) | 256 (15 ΔP) |  | 369 (15 ΔP) | 62.5 (15 ΔP) |
|  | X0HC (L/m²) | 241 (3 ΔP) |  | 352 (5.9 ΔP) | 150.6 (4.1 ΔP) |
| C0-X0 Results | C0HC (L/m²) | 203 (15 ΔP) | 226 (at ~4.8 ΔP) | 225 (15 ΔP) |  |
|  | X0HC (L/m²) | 186 (1.02 ΔP) | 200 (at ~3.1 ΔP) | 209 (2 ΔP) |  |

Example 11

Next, 11 individual runs were performed on a four-stage acoustophoretic system.

A mixture of CHO cells and culture media were flowed through the four stages of the system in series in five different CHO cell lines. The feed had a total cell density (TCD) of $9.78 \times 10^6$ to $34.3 \times 10^6$ cells/mL, a turbidity of 920 to 4670 NTU, a PCM of 6.5 to 11%, and a viability of 31-91%.

Figure 58:
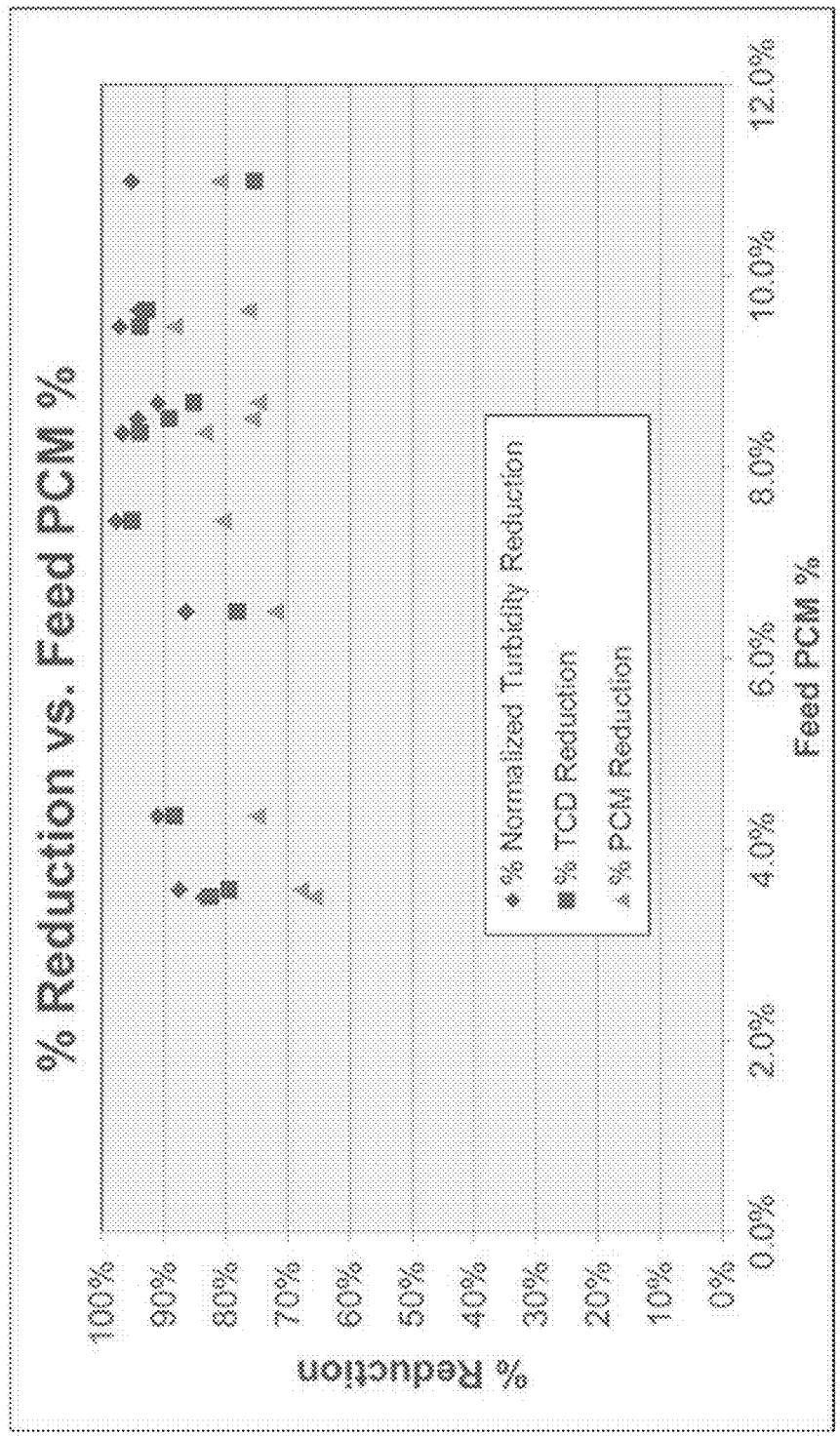
FIG. 58 is a graph showing % reduction vs feed PCM for the system of FIG. 50.
Figure 59:
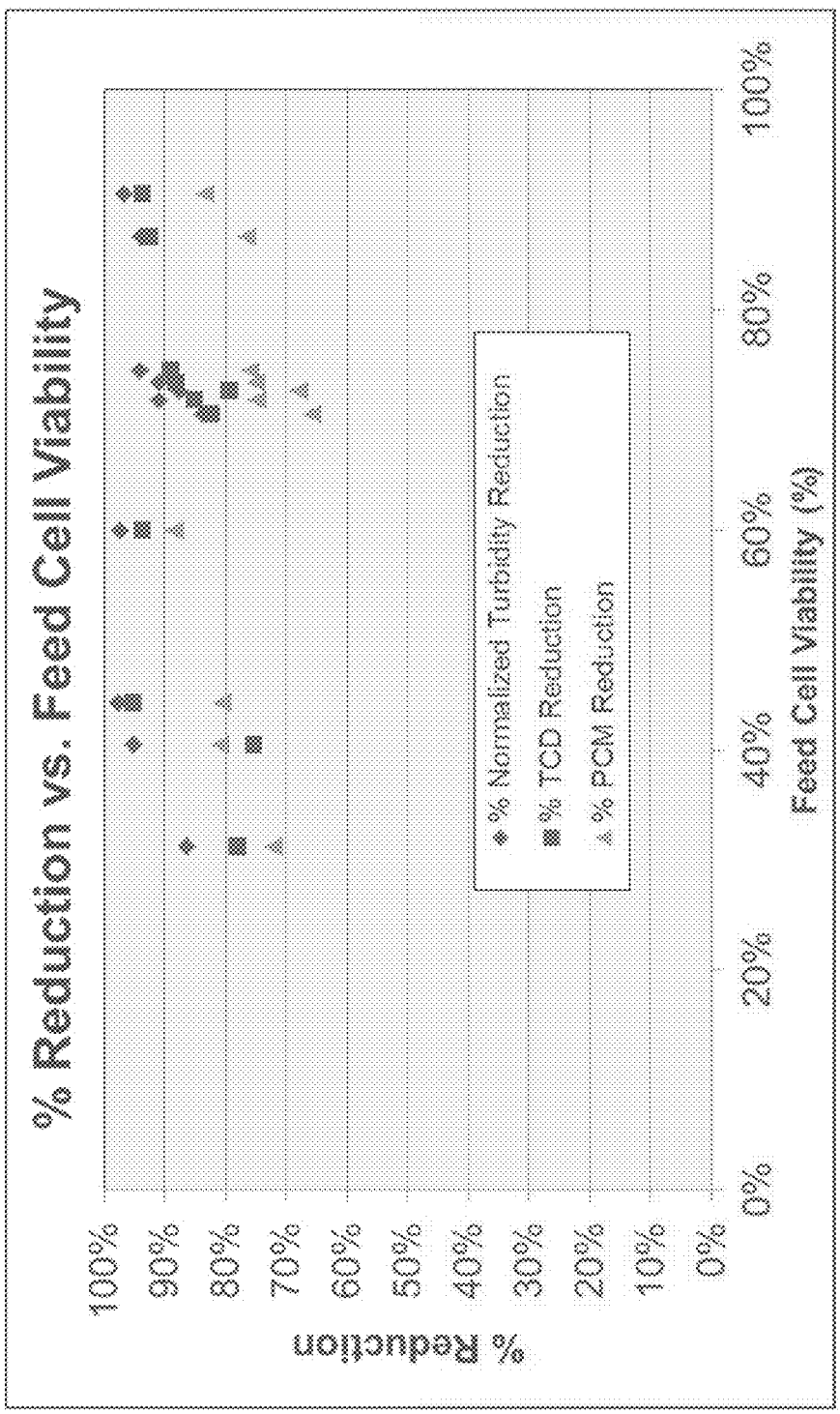
FIG. 59 is a graph showing % reduction vs feed cell viability for the system of FIG. 50.

The AWS permeate had a TCD of $0.8 \times 10^6$ to $5.2 \times 10^6$ cells/mL (average=$2.9 \times 10^6$ cells/mL), a turbidity of 121 to 453 NTU ((average=236 NTU), and a PCM of 1.1 to 2.3% (average=1.6%). The reduction performance was a TCD reduction of 76% to 95% (average=88%), a turbidity reduction of 86% to 97% (average=94%), and a PCM reduction of 72% to 88% (average=79%). The yield was 84% to 89% (average=86%). FIG. 58 shows the reduction performance as a function of the feed PCM, and FIG. 59 shows the reduction performance as a function of the feed cell viability.

Example 12

Figure 60:
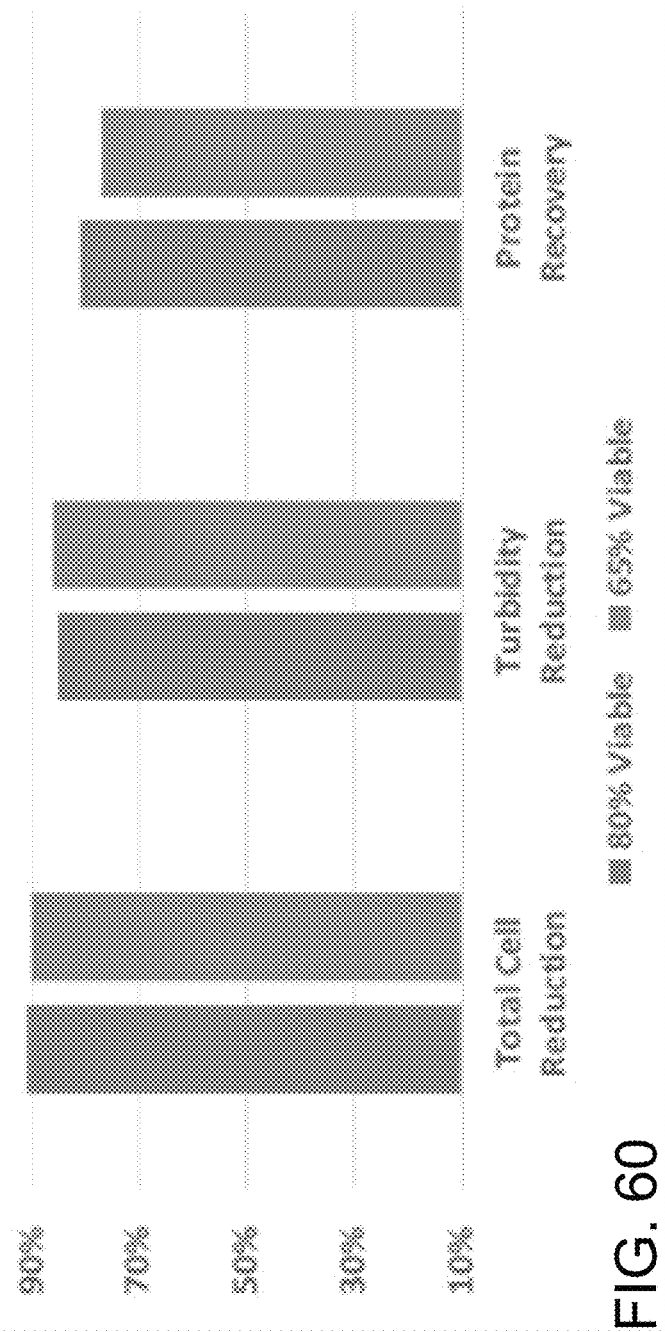
FIG. 60 is a graph showing the performance of a seventh experimental system.

Two CHO cell lines with a multi-specific antibody (MM-131) was flowed through a three-stage acoustophoretic system with stages having a 1 inch by 1 inch ultrasonic transducer. The feed had a total cell density (TCD) of $20 \times 10^6$ to $24 \times 10^6$ cells/mL. The first feed line had a 80% cell viability and is depicted as the leftmost bar in each series. The second feed line had a 65% cell viability and is depicted as the rightmost bar in each series. FIG. 60 shows the total cell reduction, turbidity reduction, and protein recovery.

Example 13

Figure 61:
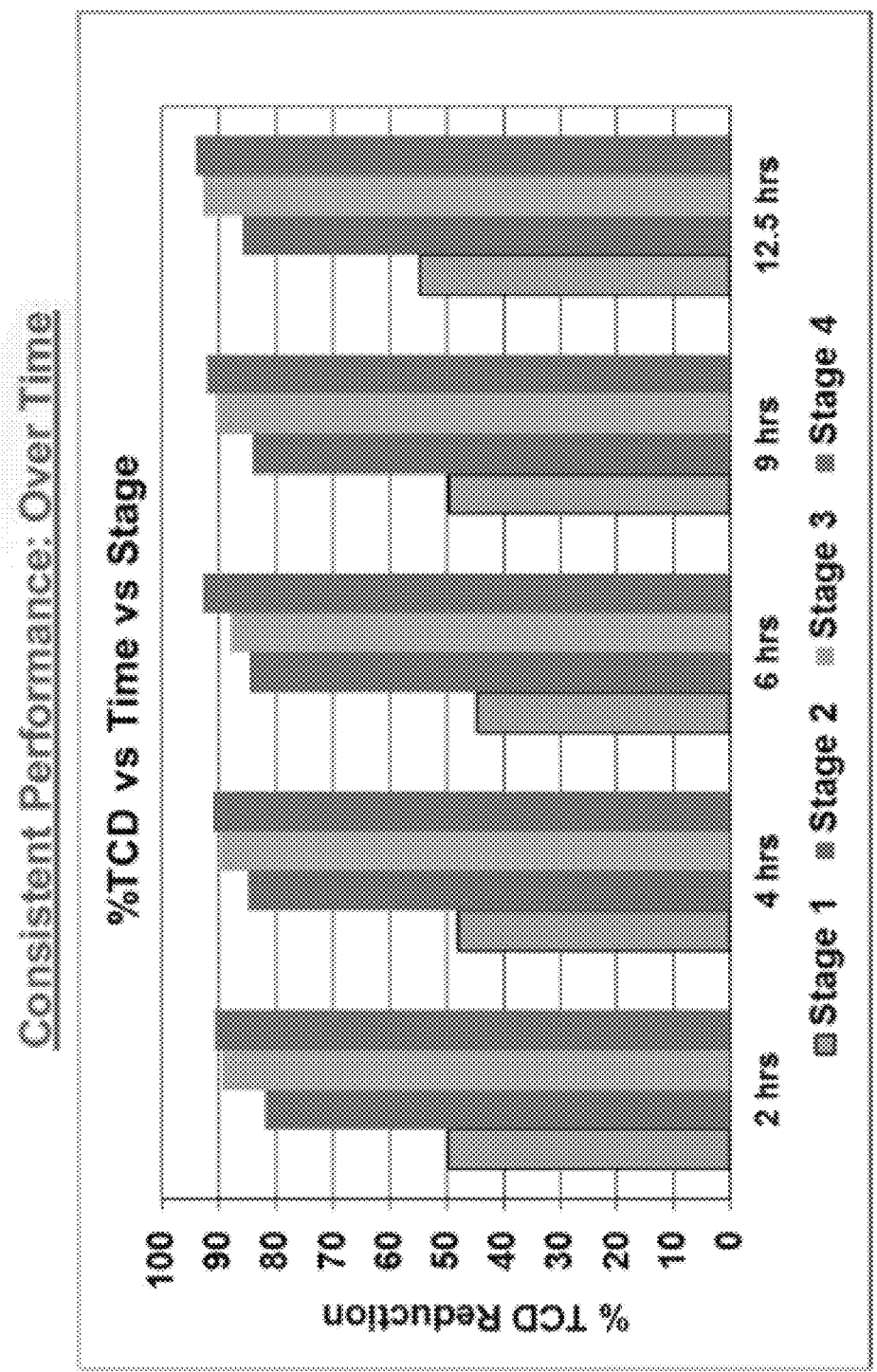
FIG. 61 is another graph showing the performance of the seventh experimental system. The performance of each stage is shown over time, and shows that the performance does not deteriorate.

In a four-stage system, the system performance was also measured over time for each stage. FIG. 61 shows the TCD reduction at each stage and at intervals of 2 hours, 4 hours, 6 hours, 9 hours, and 12.5 hours. The leftmost bar in each series represents the first stage, the second bar from the left in each series represents the second stage, the second bar from the right in each series represents the third stage, and the rightmost bar in each series represents the fourth stage. Addition of the fourth stage showed an increased TCD reduction at each time interval. This graph shows that each acoustophoretic stage maintains its performance and its separation ability does not decrease over time, as a physical filter would.

Example 14

Figure 62:
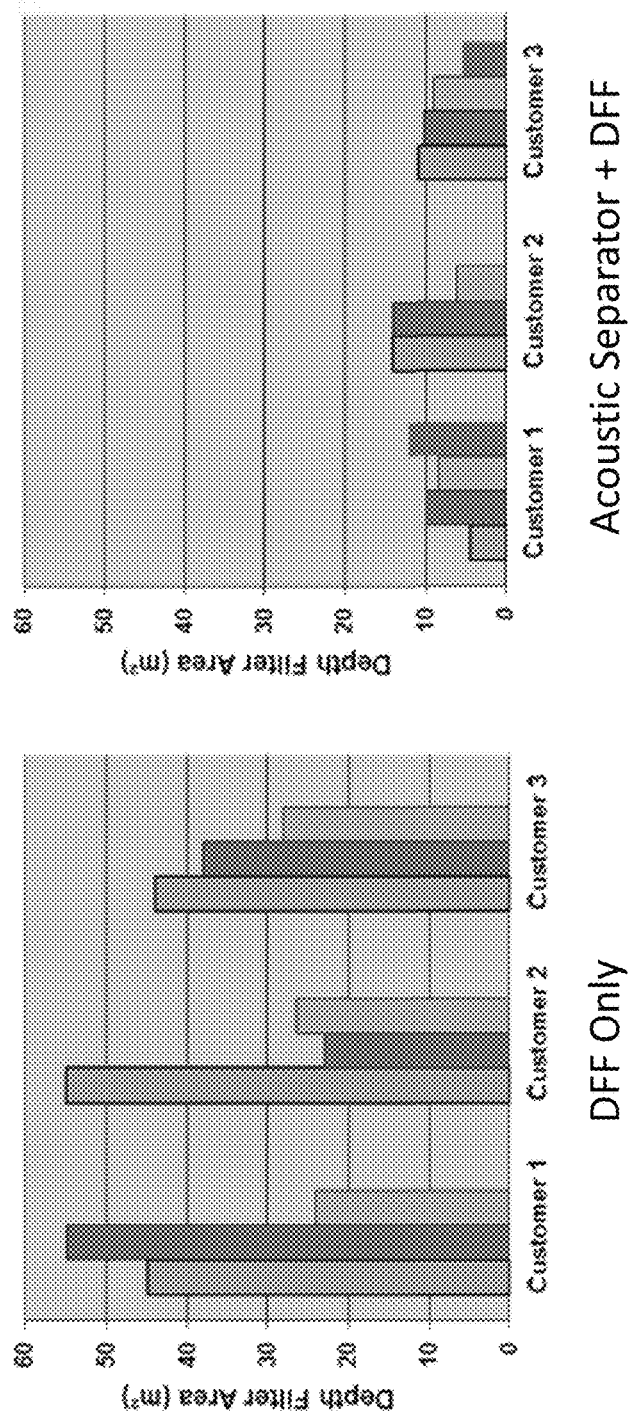
FIG. 62 is another graph showing the performance of the seventh experimental system. This compares the depth filter area needed for a depth filter versus the equivalent area for an acoustophoretic filter of the same capacity.

For three discrete customers, the reduction in depth filter area was compared between DFF only and a four-stage AWS system fed into a DFF filter. FIG. 62 shows that use of a four-stage AWS system reduced the depth filter area required between 3- and 10-fold.

Example 14

Figure 63:
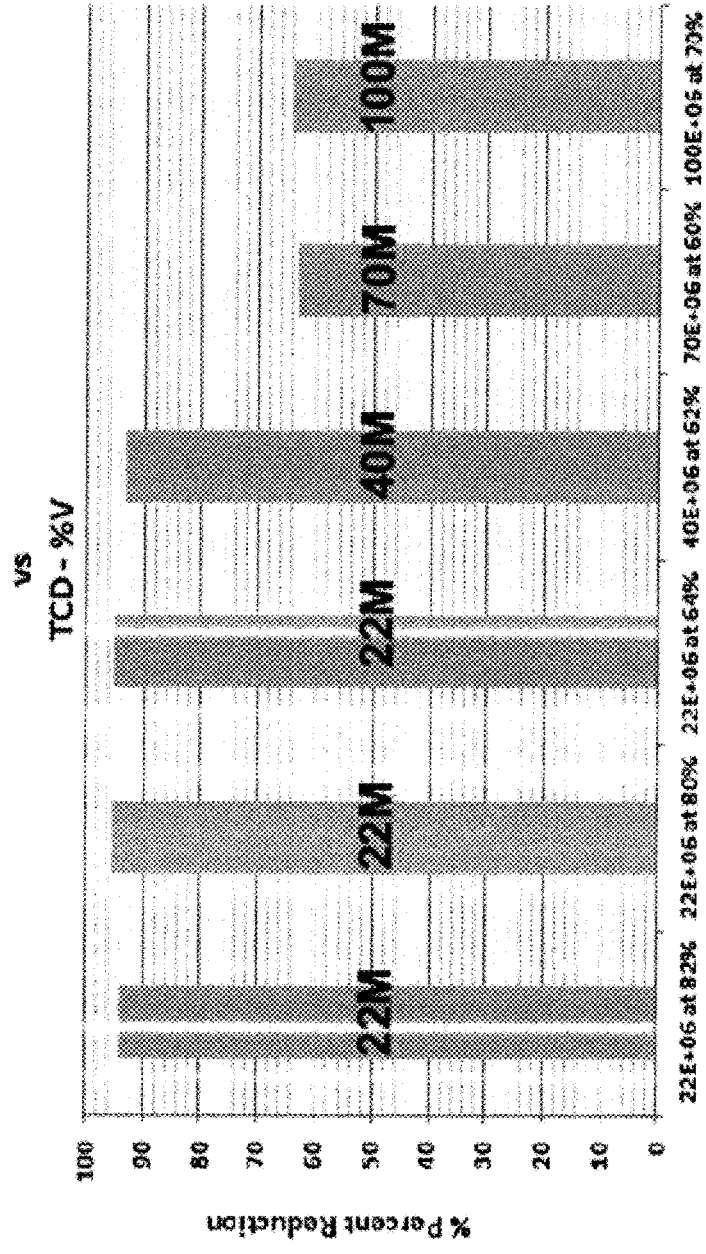
FIG. 63 is another graph showing the performance of the seventh experimental system.

FIG. 63 is a graph showing the cell density reduction for five different runs through a three-stage system having transducers of size 1 inch by 1 inch. The bottom of each bar indicates the total cell density (cells/mL) and the cell viability. The y-axis is the percent reduction of cells from the feed to the permeate, and a higher value is better. These results show good separation even for high total cell density.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A multi-stage acoustophoretic system, comprising:
   three or more acoustophoretic devices fluidly connected to one another in series, each acoustophoretic device comprising:
      a flow chamber having at least one dump diffuser acting as an inlet and at least one outlet;
      at least one ultrasonic transducer coupled to the flow chamber, the transducer including a piezoelectric material configured to be driven by a signal to create a multi-dimensional acoustic standing wave in the flow chamber; and
      a reflector opposite from the at least one ultrasonic transducer.

2. The multi-stage acoustophoretic system of claim 1, wherein the three or more acoustophoretic devices are fluidly connected to one another by tubing.

3. The multi-stage acoustophoretic system of claim 1, comprising a total of four acoustophoretic devices.

4. The multi-stage acoustophoretic system of claim 1, further comprising a feed pump and a pump downstream of each acoustophoretic device.

5. The multi-stage acoustophoretic system of claim 1, further comprising a flowmeter upstream of the first acoustophoretic device and a flowmeter downstream of each acoustophoretic device.

6. A method for continuously separating a second fluid or a particulate from a host fluid, the method comprising:
   flowing a mixture of the host fluid and the second fluid or particulate through a multi-stage acoustophoretic system, the multi-stage acoustophoretic system comprising three or more acoustophoretic devices fluidly connected to one another, each acoustophoretic device comprising:
      a flow chamber having at least one dump diffuser acting as an inlet and at least one outlet;
      at least one ultrasonic transducer couple to the flow chamber, the transducer including a piezoelectric material driven by a signal to create a multi-dimensional acoustic standing wave in the flow chamber; and
      a reflector on the opposite side of the flow chamber from the at least one ultrasonic transducer; and
   driving the at least one ultrasonic transducer of a first one of the three or more acoustophoretic devices to create a first multi-dimensional acoustic standing wave therein, such that at least a portion of the second fluid or particulate is continuously trapped in the first standing wave, with the residual host fluid continuing into a second one of the three or more acoustophoretic devices;

driving the at least one ultrasonic transducer of the second one of the three or more acoustophoretic devices to create a second multi-dimensional acoustic standing wave therein, such that at least a portion of the second fluid or particulate is continuously trapped in the second standing wave, with the residual host fluid continuing into a third one of the three or more acoustophoretic devices; and driving the at least one ultrasonic transducer of the third one of the three or more acoustophoretic devices to create a third multi-dimensional acoustic standing wave therein, such that at least a portion of the second fluid or particulate is continuously trapped in the third standing wave.

7. The method of claim 6, wherein the first, second, and third acoustic standing waves all have different frequencies from each other.

8. The method of claim 6, wherein the first, second, and third acoustic standing waves all have frequencies within one order of magnitude of each other.

9. The method of claim 6, wherein the second fluid or particulate is Chinese hamster ovary (CHO) cells, NS0 hybridoma cells, baby hamster kidney (BHK) cells, or human cells; T cells, B cells, or NK cells; peripheral blood mononuclear cells (PBMCs); algae; plant cells, bacteria, viruses, or microcarriers.

10. The method of claim 6, wherein the three or more acoustophoretic devices are fluidly connected to one another by tubing.

11. The method of claim 6, wherein the multi-stage acoustophoretic system comprises a total of four acoustophoretic devices.

12. The method of claim 6, further comprising driving at least one of the ultrasonic transducers with a voltage signal of at least 50V.

13. The method of claim 6, further comprising driving each of the ultrasonic transducers with a voltage signal of from about 50V to about 60V.

14. The method of claim 6, further comprising driving the furthest downstream of the ultrasonic transducers with a voltage signal of from about 40V to about 60V.

15. The method of claim 6, wherein the at least one outlet of each acoustophoretic device includes a permeate outlet at an upper end of the flow chamber and a solids outlet at a lower end of the flow chamber opposite the upper end.

16. The multi-stage acoustophoretic system of claim 1, wherein the at least one outlet of each acoustophoretic device includes a permeate outlet at an upper end of the flow chamber and a solids outlet at a lower end of the flow chamber opposite the upper end.

17. A multi-stage acoustophoretic system, comprising:
at least a first acoustophoretic device, a second acoustophoretic device, and a third acoustophoretic device fluidly connected sequentially in series, each acoustophoretic device comprising:
a flow chamber including at least one inlet, a solids outlet, and a permeate outlet;
at least one ultrasonic transducer coupled to the flow chamber and including a piezoelectric material and configured to be driven to create an acoustic standing wave in the flow chamber; and
a reflector opposite from the at least one ultrasonic transducer.

18. The multi-stage acoustophoretic system of claim 17, wherein the permeate outlet of the first acoustophoretic device is fluidly connected to the at least one inlet of the second acoustophoretic device, and the permeate outlet of the second acoustophoretic device is fluidly connected to the at least one inlet of the third acoustophoretic device.

19. The multi-stage acoustophoretic system of claim 17, further comprising a fourth acoustophoretic device downstream of the third acoustophoretic device and fluidly connected thereto in series.

20. The multi-stage acoustophoretic system of claim 17, wherein each acoustic standing wave results in an acoustic radiation force with an axial force component and a lateral force component that are of the same order of magnitude.

* * * * *